United States Patent
Lu et al.

(10) Patent No.: US 10,155,756 B2
(45) Date of Patent: Dec. 18, 2018

(54) PYRAZOLO[1,5-A]PYRIDINE COMPOUNDS AND USE THEREOF

(71) Applicant: GUANGZHOU INSTITUTES OF BIOMEDICINE AND HEALTH, CHINESE ACADEMY OF SCIENCES, Guangdong (CN)

(72) Inventors: Xiaoyun Lu, Guangzhou (CN); Jian Tang, Guangzhou (CN); Ke Ding, Guangzhou (CN); Tianyu Zhang, Guangzhou (CN); Xiantao Zhang, Guangzhou (CN); Zhengchao Tu, Guangzhou (CN); Tian Wu, Guangzhou (CN); Junting Wan, Guangzhou (CN); Yuanyuan Cao, Guangzhou (CN); Shengjiang He, Guangzhou (CN)

(73) Assignee: Guangzhou Eggbio Co., Ltd., Guangzhou (CN)

( * ) Notice: Subject to any disclaimer, the term of this patent is extended or adjusted under 35 U.S.C. 154(b) by 0 days.

(21) Appl. No.: 15/520,765

(22) PCT Filed: Aug. 13, 2015

(86) PCT No.: PCT/CN2015/086852
§ 371 (c)(1),
(2) Date: Apr. 20, 2017

(87) PCT Pub. No.: WO2016/062151
PCT Pub. Date: Apr. 28, 2016

(65) Prior Publication Data
US 2017/0313697 A1 Nov. 2, 2017

(30) Foreign Application Priority Data

Oct. 21, 2014 (CN) .......................... 2014 1 0562805
Jul. 29, 2015 (CN) .......................... 2015 1 0460751

(51) Int. Cl.
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC ................. C07D 471/04 (2013.01)

(58) Field of Classification Search
CPC .. C07D 401/02; C07D 401/10; A61K 31/437; A61K 31/4353
USPC ........................................ 546/121; 514/300
See application file for complete search history.

(56) References Cited

U.S. PATENT DOCUMENTS

| 7,501,405 B2 * | 3/2009 | Kampen ............... A61K 31/519 514/211.01 |
| 7,795,273 B2 * | 9/2010 | Imbach ................ C07D 471/04 514/300 |
| 8,642,660 B2 * | 2/2014 | Goldfarb ............. A61K 31/122 514/18.9 |
| 8,927,545 B2 * | 1/2015 | Qiao .................... A61K 31/437 514/234.2 |
| 2006/0094699 A1* | 5/2006 | Kampen ............... A61K 31/519 514/171 |
| 2006/0111366 A1* | 5/2006 | Andersen ............. A61K 31/16 514/253.01 |
| 2013/0331397 A1 | 12/2013 | Molteni et al. |
| 2015/0025059 A1 | 1/2015 | Bruce et al. |

FOREIGN PATENT DOCUMENTS

| CN | 103492384 A | 1/2014 |
| CN | 104024252 A | 9/2014 |
| WO | 2009/015208 A1 | 1/2009 |
| WO | 2011050245 | * 4/2011 |

OTHER PUBLICATIONS

Qiao et al., Bioorganic & Medicinal Chemistry Letters (2009), 19(21), 6122-6126.*
Chinese First Office Action, dated Jan. 23, 2017, on for Chinese Application No. 201510460751.6, 10 pages. (with English Translation).
Chinese Second Office Action, dated Aug. 3, 2017, for Chinese Application No. 201510460751.6, 7 pages. (with English Translation).

(Continued)

*Primary Examiner* — Niloofar Rahmani
(74) *Attorney, Agent, or Firm* — Seed IP Law Group LLP

(57) ABSTRACT

Disclosed in the disclosure are a pyrazolo [1,5-a] pyrideine compound with structural features as shown in formula (I) or a pharmaceutically acceptable salt, stereoisomer or prodrug molecule thereof and a use thereof. Such compounds have a good in vitro antituberculosis activity, and the minimal inhibitory concentration (MIC) of the compounds is lower than 0.1 μg/mL and partially achieves 0.01 μg/mL, and have a very strong inhibiting effect on clinically selected multi-drug resistant tuberculosis (MDR-TB) strains. In an in vivo experiment, the pyrazolo[1,5-a] pyrideine compounds of the present disclosure can effectively scavenge the infectious dose of H37Ra in a mouse body at 20 mg/kg/d does, thereby being a new type of antituberculosis compound.

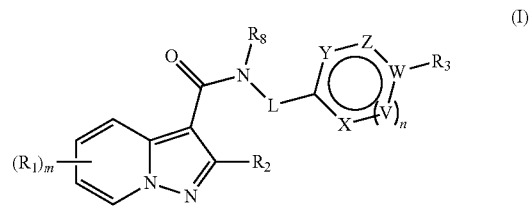

11 Claims, 2 Drawing Sheets

(56) References Cited

OTHER PUBLICATIONS

Chinese Search Report, dated Jan. 13, 2017, for Chinese Application No. 201510460751.6, 2 pages.
Chinese Supplementary Search Report, dated Jul. 11, 2017, for Chinese Application No. 201510460751.6, 1 page.
International Search Report, dated Nov. 17, 2015, for International Application No. PCT/CN2015/086852, 2 pages.
Written Opinion of the International Searching Authority, dated Nov. 17, 2015, for International Application No. PCT/CN2015/086852, 5 pages.

* cited by examiner

PYRAZOLO[1,5-A]PYRIDINE COMPOUNDS AND USE THEREOF

TECHNICAL FIELD

The present disclosure relates to the chemical medicine field, particularly relates to pyrazolo[1,5-a]pyridine compounds and the use thereof.

BACKGROUND

Tuberculosis (TB) is caused by *Mycobacterium tuberculosis* (Mtb) infection, being one of the most prevalent diseases in the world. In human tuberculosis, the most common one is pulmonary tuberculosis, accounting for 80-90% of the total number of organ tuberculosis. Due to the emergence of drug-resistant tuberculosis and AIDS co-infection, the existing clinical drug treatment effect is greatly reduced.

According to the 18th WHO Global Tuberculosis Report, there are about 8.6 million new tuberculosis patients worldwide in 2012, with a death toll of 1.3 million. In China, the incidence of tuberculosis accounts for 12% of the world's incidence (1 million people) ranking second in the world, and the death toll of 44,000 ranking fifth in the world. Multi-drug resistant tuberculosis further widely spreads in this world, and there are about 450,000 new cases of resistance in 2012. And China is one of the 27 countries with severe multi-drug resistant tuberculosis epidemic in the world, and about 1.6 million people are reported as multi-drug resistant tuberculosis.

The current treatment is a combination therapy of the first-line drugs isoniazid, rifampicin, pyrazinamide and ethambutol etc. with the second-line drugs, with a treatment time of 6-9 months, which does not have good treatment effect on drug resistant *mycobacterium tuberculosis* and persister bacteria and brings great distress and economic bureden to patients. Resistance mechanisms of first-line anti-TB drugs currently used have been relatively clear, that is mainly due to improper use of drugs, mutation of the corresponding target gene or drug activation related enzyme gene or related regulatory gene occur, resulting in drug failure. As a result, at the launch of the Global Alliance for TB Drug Development, people have begun to re-focus on the development of anti-TB drugs. The new drug should have the following characteristics: (1) developing a new drug that can shorten the treatment cycle; (2) developing a drug that is effective against drug-resistant *mycobacterium tuberculosis*; (3) developing a new drug that can effectively treat latent bacterial infections.

There are three main aspects of research and development of anti-tuberculosis drugs: natural selection, design and synthesis of a new structure type compound, and re-modification of an antibacterial drug. In recent years, some new synthetic anti-TB drugs at home and abroad are quinoline, nitroimidazopyrans, oxazolidinones, pyrrole, imidazopyridines and so on. At the end of 2012, the bis-arylquinoline drug bedaquiline was accelerated approved by the FDA for approval as one of the components of the adult MDR-TB treatment program, and this is the first new anti-tuberculosis drug since the introduction of rifampicin in 1970. But the follow-up clinical trials show that bedaquiline also showed a certain side effects, and security risks still exist. Therefore, it is of great significance to further develop a safe and effective anti-tuberculosis drug to overcome the risk of clinically drug-resistant tuberculosis.

SUMMARY

Based on the above, a purpose of the present disclosure is to provide a pyrazolo[1,5-a]pyridine compound and the use thereof.

In order to achieve the purpose, the present disclosure adopts the following technical solution:

A pyrazolo[1,5-a]pyridine compound having a structure of formula (I) or a pharmaceutically acceptable salt thereof or a stereoisomer thereof or a prodrug molecule thereof:

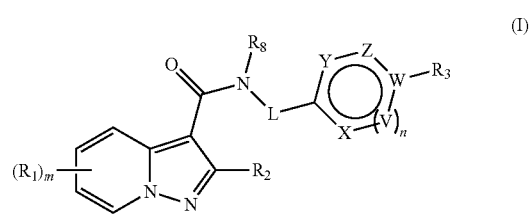

m is 0, 1, 2, 3 or 4; n is 0 or 1; V is CH or N; W is CH or N; X is optionally selected from the group consisting of CH, O, N and S; Y is optionally selected from the group consisting of CH, O, N and S; Z is optionally selected from the group consisting of CH, O, N and S; L is optionally selected from: $C_0$-$C_5$ straight or branched alkanes; $R_8$ is H or methyl;

$R_1$ is optionally selected from the group consisting of 1) H; 2) halogen; 3) $O_a C_1$-$C_5$ alkyl; 4) $C_3$-$C_6$ cycloalkyl; 5) aryl; 6) amino, hydroxy, cyano, nitro; and 7) heteroaryl; wherein the alkyl, the aryl, the cycloalkyl and the heteroaryl are optionally substituted with 0, 1, 2 or 3 substituents selected from $R_6$, respectively;

$R_2$ is optionally selected from the group consisting of: 1) H; 2) $O_a C_1$-$C_5$ alkyl; 3) $C_3$-$C_6$ cycloalkyl; 4) aryl; and 5) heteroaryl;

wherein the alkyl, the aryl, the cycloalkyl and the heteroaryl are optionally substituted with 0, 1, 2 or 3 substituents selected from $R_6$, respectively.

$R_3$ is optionally selected from the group consisting of 1) H; 2) halogen; 3) $O_a C_1$~$C_5$ alkyl; 4) $C_3$~$C_6$ cycloalkyl; 5)

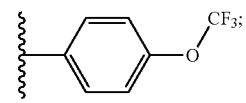

6)

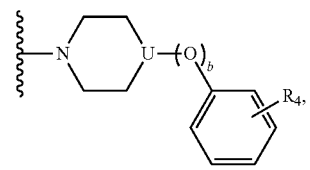

wherein b is 0 or 1, U is CH or N; $R_4$ is optionally selected from the group consisting of H; F, Cl, Br; $C_1$~$C_3$ alkyl; $C_1$~$C_3$ alkoxy; and phenoxy; 7)

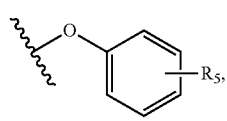

wherein R₅ is optionally selected from the group consisting of H; F, Cl, Br; and $O_aC_1$~$C_3$ alkyl; 8)

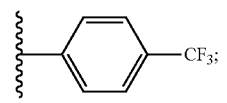 [SMILES: *c1ccc(C(F)(F)F)cc1]

9) (C=O) $_cO_dR_7$, wherein c is 0 or 1; d is 0 or 1; R₇ is optionally selected from the group consisting of a) CF₃; and b) $C_1$~$C_5$ alkyl; 10) —N(CH₃)₂; 11)

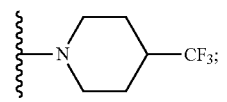

and 12)

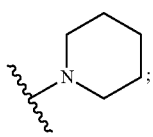

The alkyl, the aryl, the cycloalkyl, the heterocycloalkyl and the heteroaryl are optionally substituted with 0, 1, 2 or 3 substituents selected from R₆, wherein a is 0 or 1; R₆ is optionally selected from the group consisting of 1) H; 2) $C_3$~$C_6$ cycloalkyl; 3) heterocyclyl; 4) $C_1$-$C_3$ alkyl; 5) $C_1$-$C_3$ fluoroalkyl; 6) $C_0$~$C_3$ alkylene-heterocyclyl; and 7) halogen.

In one embodiment, R₁ is optionally selected from the group consisting of 1) H; 2) F, Cl, Br, I; 3) OH, OCH₃, OEt, OCF₃; 4) methyl, ethyl, isopropyl, t-butyl; 5) cyclopropyl; 6) CF₃; and 7) phenyl;

R₂ is optionally selected from the group consisting of 1) H; 2) methyl, ethyl, propyl, isopropyl, t-butyl; 3) cyclopropyl; and 4) phenyl;

R₃ is optionally selected from the group consisting of
1)

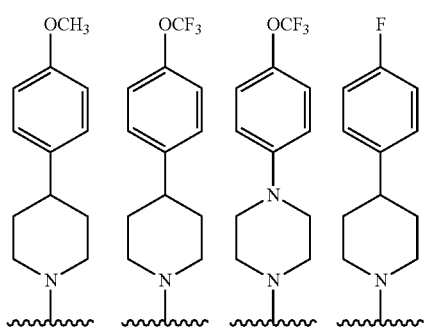

2)

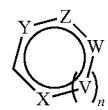

3)

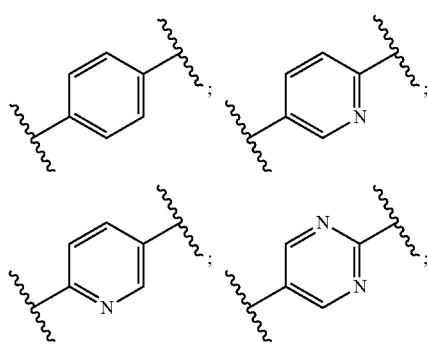

5) CF₃; 6) (C=O) $_cO_dR_7$, wherein c is 0 or 1; d is 0 or 1; R₇ is optionally selected from the group consisting of a) CF₃; b) $C_1$-$C_5$ alkyl; 7) H; and 8) halogen.

In one embodiment, the is selected from the group consisting of

-continued

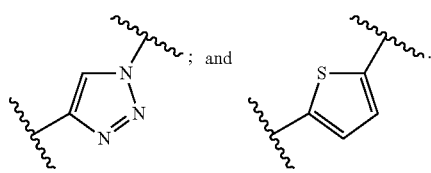

In one embodiment, the pyrazolo[1,5-a]pyridine compound has a structure of formula (II):

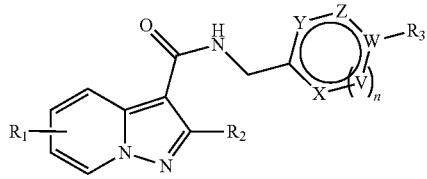

Wherein the $R_1$ is methyl; $R_2$ is methyl; $R_3$ is optionally selected from the group consisting of 1) —N(CH$_3$)$_2$; 2)

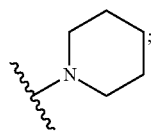 [SMILES: *N1CCCCC1]

3) —C(CH$_3$)$_3$; 4)

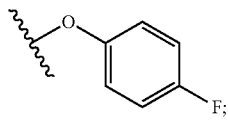 [SMILES: *Oc1ccc(F)cc1]

5)

6)

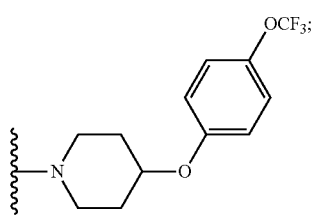 [SMILES: *N1CCC(Oc2ccc(OC(F)(F)F)cc2)CC1]

n=1.

In one embodiment, the pyrazolo[1,5-a]pyridine compound has the structure of formula (II):

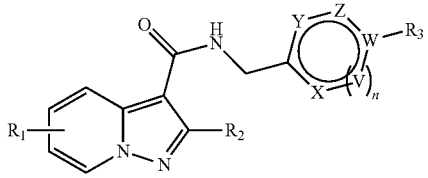

$R_1$ is optionally selected from the group consisting of 1) H; 2) F, Cl, Br, I; 3) OH, OCH$_3$, OEt, OCF$_3$; 4) methyl, ethyl, isopropyl, t-butyl; 5) cyclopropyl; 6) CF$_3$; and 7) phenyl;

$R_2$ is optionally selected from the group consisting of H; methyl, ethyl, propyl, isopropyl; cyclopropyl; and phenyl;

$R_3$ is optionally selected from the group consisting of 1)

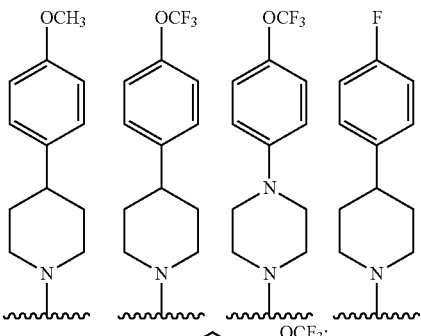

2)

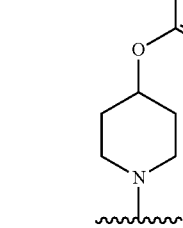

3)

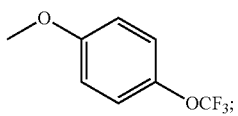

4)

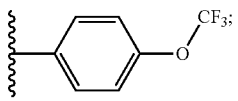

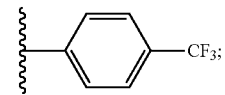

5) CF₃; 6) (C=O) OMe; 7) H; and 8) halogen;

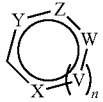

is selected from the group consisting of

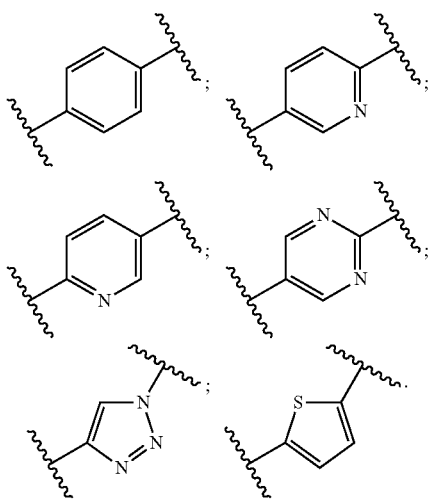

In one embodiment, the pyrazolo[1,5-a]pyridine compound has a structure of formula (III):

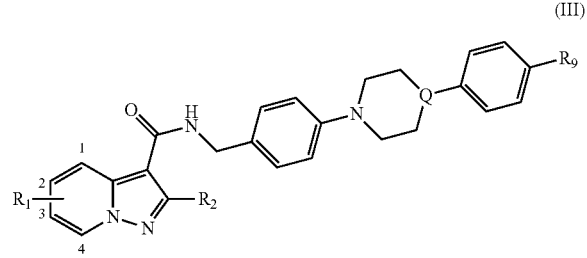

(III)

R₁ is optionally selected from the group consisting of 1) H; 2) F, Cl, Br; 3) OH, OCH₃, OEt; 4) methyl, ethyl, isopropyl, t-butyl; 5) CF₃; and 6) phenyl;
R₂ is optionally selected from the group consisting of 1) H; 2) methyl, ethyl, propyl; 3) cyclopropyl; and 4) phenyl;
R₉ is optionally selected from the group consisting of 1) F, Cl, Br; and 2) OCH₃, OCF₃;
Q is optionally selected from CH and N.
In one embodiment,
R₁ is optionally selected from the group consisting of 1) 2-Cl, 2-Br; 2) 2-OCH₃, 2-OEt; 3) 2-methyl, 2-ethyl, 3-methyl, 3-ethyl; and 4) H;
R₂ is optionally selected from the group consisting of 1) methyl, ethyl, propyl; and 2) cyclopropyl;
R₉ is optionally selected from the group consisting of 1) F, Cl; and 2) OCH₃, OCF₃;
Q is optionally selected from CH and N.
In one embodiment, the pyrazolo[1,5-a]pyridine compound has a structure of formula (IV):

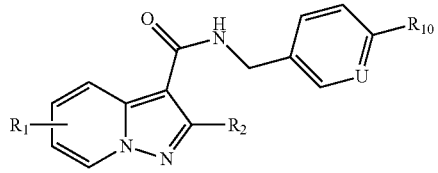

(IV)

R₁ is optionally selected from the group consisting of 1) H; 2) F, Cl, Br; 3) OH, OCH₃, OEt; 4) methyl, ethyl, isopropyl, t-butyl; 5) CF₃; and 6) phenyl;
R₂ is optionally selected from the group consisting of 1) H; 2) methyl, ethyl, propyl; 3) cyclopropyl; and 4) phenyl;
R₁₀ is optionally selected from the group consisting of 1) H; 2) F, Cl, Br; 3) CF₃; and 4)

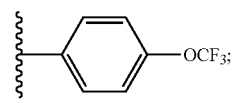 [SMILES: *c1ccc(OC(F)(F)F)cc1]

U is optionally selected from CH and N.
In one embodiment, the pyrazolo[1,5-a]pyridine compound has the structure of formula (II):

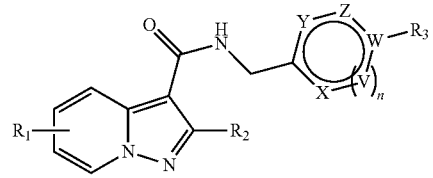

(II)

R1 is methyl; R2 is methyl;
R3 is optionally selected from 1)

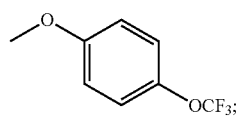

and
2)

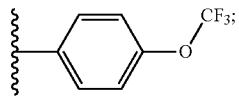

In one embodiment, the compound is selected from the group consisting of:
5-chloro-2-ethyl-N-(4-(4-(4-(trifluoromethoxy) phenyl) piperidine-1-yl) benzyl) pyrazolo [1,5-a] pyridine-3-carboxamide; 5-chloro-2-ethyl-N-(4-(trifluoromethoxy) phenyl) pyrazolo [1,5-a] pyridine-3-carboxamide; 5-chloro-N-(4-(4-(4-(trifluoromethoxy) phenyl) piperidine-1-yl) benzyl) pyrazolo [1,5-a] pyridine-3-carboxamide; 5-chloro-2-methyl-N-(4-(4-(4-(trifluoromethoxy) phenyl) piperidine-1-yl) benzyl)

pyrazolo [1,5-a] pyridine-3-carboxamide; 5-chloro-2-cyclopropyl-N-(4-(4-(4-(trifluoromethoxy) phenyl) piperidine-1-yl) benzyl) pyrazolo [1,5-a] pyridine-3-carboxamide; 2-methyl-N-(4-(4-(4-(trifluoromethoxy) phenyl) piperidine-1-yl) benzyl) pyrazolo [1,5-a] pyridine-3-carboxamide; 2,5-dimethyl-N-(4-(4-(4-(trifluoromethoxy) phenyl) piperidine-1-yl) benzyl) pyrazolo [1,5-a] pyridine-3-carboxamide; 5-chloro-2-phenyl-N-(4-(4-(4-(trifluoromethoxy) phenyl) piperidine-1-yl benzyl) pyrazolo [1,5-a] pyridine-3-carboxamide; 4-((5-chloro-2-ethylpyrazolo [1,5-a] pyridine-3-carboxamide) methyl) methyl benzoate; 5-chloro-2-ethyl-N-(4-(4-(4-(trifluoromethoxy) phenyl) piperidine-1-yl) phenyl) pyrazolo [1,5-a] pyridine-3-carboxamide; 2,7-dimethyl-N-(4-(4-(4-(trifluoromethoxy) phenyl) piperidine-1-yl) benzyl) pyrazolo [1,5-a] pyridine-3-carboxamide; 2,6-dimethyl-N-(4-(4-(4-(trifluoromethoxy) phenyl) piperidine-1-yl) benzyl) pyrazolo [1,5-a] pyridine-3-carboxamide; 2,4-dimethyl-N-(4-(4-(4-(trifluoromethoxy) phenyl) piperidine-1-yl) benzyl) pyrazolo [1,5-a] pyridine-3-carboxamide; 5-methoxy-2-ethyl-N-(4-(4-(4-(trifluoromethoxy) phenyl) piperidine-1-yl) benzyl) pyrazolo [1,5-a] pyridine-3-carboxamide; 5-chloro-2-ethyl-N-((1-(4-(trifluoromethoxy) phenyl)-1H-1,2,3-triazole-4-yl) methyl) pyrazolo [1,5-a] pyridine-3-carboxamide; 5-chloro-2-ethyl-N-methyl-N-(4-(4-(4-(trifluoromethoxy) phenyl) piperidine-1-yl) phenyl) pyrazolo [1,5-a] pyridine-3-carboxamide; 5-chloro-2-ethyl-N-(2-(4-(4-(4-(trifluoromethoxy) phenyl) piperidine-1-yl) phenyl) propane-2-yl) pyrazolo [1,5-a] pyridine-3-carboxamide; 5-trifluoromethyl-2-methyl-N-(4-(4-(4-(trifluoromethoxy) phenyl) piperidine-1-yl) benzyl) pyrazolo [1,5-a] pyridine-3-carboxamide; 2,5-dimethyl-N-((1-(4-(trifluoromethoxy) phenyl)-1H-1,2,3-triazole-4-yl) methyl) pyrazolo [1,5-a] pyridine-3-carboxamide; 5-bromo-2-methyl-N-(4-(4-(4-(trifluoromethoxy) phenyl) piperidine-1-yl) benzyl) pyrazolo [1,5-a] pyridine-3-carboxamide; 5-phenyl-2-methyl-(4-(4-(4-(trifluoromethoxy) phenyl) piperidine-1-yl) benzyl) pyrazolo [1,5-a] pyridine-3-carboxamide; 5-chloro-2-ethyl-N-((6-(4-(trifluoromethoxy) phenyl) pyridine-3-yl) methyl) pyrazolo [1,5-a] pyridine-3-carboxamide; 2,5-dimethyl-N-((6-(4-(trifluoromethoxy) phenyl) pyridine-3-yl) methyl) pyrazolo [1,5-a] pyridine-3-carboxamide; 5-methoxy-2-methyl-N-(4-(4-(4-(trifluoromethoxy) phenyl) piperidine-1-yl) benzyl) pyrazolo [1,5-a] pyridine-3-carboxamide; 2-methyl-N-(4-(trifluoromethoxy) benzyl) pyrazolo [1,5-a] pyridine-3-carboxamide; 5-chloro-2-ethyl-N-(1-(4-(4-(4-(trifluoromethoxy) phenyl) piperidine-1-yl) phenyl) ethanol) pyrazolo [1,5-a] pyridine-3-carboxamide; 2,5-dimethyl-N-(4-(trifluoromethoxy) benzyl) pyrazolo [1,5-a] pyridine-3-carboxamide; 5-isopropyl-2-methyl-N-(4-(4-(4-(trifluoromethoxy) phenyl) piperidine-1-yl) benzyl) pyrazolo [1,5-a] pyridine-3-carboxamide; 5-tert-butyl-2-methyl-N-(4-(4-(4-(trifluoromethoxy) phenyl) piperidine-1-yl) benzyl) pyrazolo [1,5-a] pyridine-3-carboxamide; 5-ethyl-2-methyl-N-(4-(4-(4-(trifluoromethoxy) phenyl) piperidine-1-yl) benzyl) pyrazolo [1,5-a] pyridine-3-carboxamide; 5-methyl-2-ethyl-N-(4-(4-(4-(trifluoromethoxy) phenyl) piperidine-1-yl) benzyl) pyrazolo [1,5-a] pyridine-3-carboxamide; 5-methyl-2-ethoxy-N-(4-(4-(4-(trifluoromethoxy) phenyl) piperidine-1-yl) benzyl) pyrazolo [1,5-a] pyridine-3-carboxamide; 5-chloro-2-ethyl-N-(4-(4-(4-(trifluoromethoxy) phenyl) piperidine-1-yl) phenethyl) pyrazolo [1,5-a] pyridine-3-carboxamide; 2,5-dimethyl-N-(5-(4-(trifluoromethoxy) phenyl) thiophene-2-yl) methyl) pyrazolo [1,5-a] pyridine-3-carboxamide; 2,5-dimethyl-N-(5-(4-(trifluoromethoxy) phenyl) pyridine-2-yl) methyl) pyrazolo [1,5-a] pyridine-3-carboxamide; 2,5-dimethyl-N-(5-(4-(trifluoromethoxy) phenyl) pyridine-2-yl) methyl) pyrazolo [1,5-a] pyridine-3-carboxamide; N-(4-(tert-butyl) benzyl)-2,5-dimethylpyrazolo [1,5-a] pyridine-3-carboxamide; N-(4-(dimethylamino) benzyl)-2,5-dimethylpyrazolo [1,5-a] pyridine-3-carboxamide; N-(4-(4-(4-methoxyphenyl) piperidine-1-yl) benzyl)-2,5-dimethyl-pyrazolo [1,5-a] pyridine-3-carboxamide; N-(4-(4-fluorophenyl) piperidine-1-yl) benzyl)-2,5-dimethyl-pyrazolo [1,5-a] pyridine-3-carboxamide; 2,5-dimethyl-N-(4-(piperidin-1-yl) benzyl) pyrazolo [1,5-a] pyridine-3-carboxamide; N-(4-(4-fluorophenoxy) benzyl)-2,5-dimethylpyrazolo [1,5-a] pyridine-3-carboxamide; 2,5-dimethyl-N-(4-(4-(trifluoromethyl) piperidine-1-yl) benzyl) pyrazolo [1,5-a] pyridine-3-carboxamide; 2,5-dimethyl-N-((2-(4-(trifluoromethoxy) phenyl) pyrimidine-5-yl) methyl) pyrazolo [1,5-a] pyridine-3-carboxamide; 2,5-dimethyl-N-((4'-(trifluoromethoxy)-[1,1'-biphenyl]-4-yl) methyl) pyrazolo [1,5-a] pyridine-3-carboxamide; N-(4-(4-(4-fluorophenyl) piperazine-1-yl) benzyl)-2,5-dimethyl-pyrazolo [1,5-a] pyridine-3-carboxamide; 2,5-dimethyl-N-(4-(4-(trifluoromethoxy) phenyl) benzyl) pyrazolo [1,5-a] pyridine-3-carboxamide; 2,5-dimethyl-N-(4-(4-(4-(trifluoromethoxy) phenoxy) piperidine-1-yl) benzyl) pyrazolo [1,5-a] pyridine-3-carboxamide; 5-chloro-2-ethyl-N-(4-fluorobenzyl) pyrazolo [1,5-a] pyridine-3-carboxamide; N-(4-fluorobenzyl)-2,5-dimethylpyrazolo [1,5-a] pyridine-3-carboxamide.

The present disclosure also provides the use of the pyrazolo [1,5-a] pyridine compound or a pharmaceutically acceptable salt thereof or a stereoisomer thereof or a prodrug molecule thereof in the preparation of a medicine with anti-tuberculosis effect.

The present disclosure also provides an anti-tuberculosis pharmaceutical composition comprising an active ingredient comprising the pyrazolo [1,5-a] pyridine compound or a pharmaceutically acceptable salt thereof or a stereoisomer thereof or a prodrug molecular thereof.

The compound of the present disclosure, when any variable (e.g., $R_3$, $R_4$, $R_5$, $R_6$, $R_7$, etc.) appears more than once in any component, the definition of each occurrence is independent of the other occurrence of each occurrence. Likewise, a combination of substituents and variables is allowed as long as the combination stabilizes the compound. The lines from the substituents into the ring system indicate that the indicated bond can be attached to any of the substitutable ring atoms. If the ring system is a polycyclic, it means that the bond is only attached to any suitable carbon atom adjacent to the ring. It is to be understood that a person skilled in the art can select the substituents and substitution types of the compound of the present disclosure to provide a compound that is chemically stable and readily synthesizable from readily available raw materials by techniques in the art and the method set forth below. If the substituents themselves are substituted by more than one group, it is to be understood that these groups may be on the same carbon atom or on different carbon atoms as long as the structure is stable.

The $C_0$ alkane in the "$C_0$ to $C_5$ straight or branched alkanes" of the present disclosure is H.

The term "optionally substituted with one or more substituents" in the present disclosure is considered to be equivalent to the term "optionally substituted with at least one substituent", and in this case the preferred embodiment will have 0-3 substituents.

The "alkoxy" of the present disclosure represents a cyclic or non-cyclic alkyl of a specified number of carbon atoms attached through an oxygen bridge. Thus "alkoxy" includes the definition of the alkyl and cycloalkyl.

The "aryl" of the present disclosure refers to any stable monocyclic carbocyclic ring with up to 7 atoms in the ring or bicyclic carbocyclic ring with up to 7 atoms in each ring, at least one of which is an aromatic ring. Examples of such "aryl" include, but are not limited to, phenyl, naphthyl, tetrahydronaphthyl, indanyl, and biphenyl. In the example where the "aryl" substituent is bicyclic and one ring is non-aromatic, it is to be understood that the aromatic ring is attached.

The "heteroaryl" of the present disclosure represents a stable monocyclic carbocyclic ring with up to 7 atoms in the ring or bicyclic carbocyclic ring with up to 7 atoms in each ring, at least one of which is an aromatic ring and contains 1-4 heteroatoms selected from O, N and S. Examples of such "heteroaryl" include, but not limited to, acridinyl, carbazolyl, cinnolinyl, quinoxalinyl, pyrrazolyl, indolyl, benzotriazolyl, furyl, thienyl, benzothienyl, benzofuryl, quinolyl, isoquinolyl, oxazolyl, isoxazolyl, indolyl, pyrazinyl, pyridazinyl, pyridyl, pyrimidinyl, pyrrolyl, and tetrahydroquinoline. The "heteroaryl" is also understood to include any N-oxide derivative of a heteroaryl containing nitrogen. In the example where the "heteroaryl" substituent is bicyclic and contains a ring that is non-aromatic or does not contain heteroatoms, it is to be understood that each is linked via an aromatic ring or via a heteroatom-containing ring.

The term "heterocycle" or "heterocyclyl" of the present disclosure means a 5-10-membered aromatic or non-aromatic heterocyclic ring containing 1 to 4 heteroatoms selected from O, N and S, and includes bicyclic groups. Thus, "heterocyclyl" includes the "heteroaryl", and also includes a dihydrogenated and tetrahydric analogue thereof Examples of such "heterocyclyl" include, but not limited to, benzimidazolyl, benzofuranyl, benzopyranyl, benzopyrazole, benzotriazolyl, benzothienyl, benzo oxazolyl, carbazolyl, carbolinyl, cinnolinyl, furyl, imidazolyl, indolinyl, indolyl, indolazinyl, indazolyl, isobenzopyranyl, isoindolyl, isoquinolyl, isothiazolyl, isoxazolyl, neviopyridyl, oxadiazolyl, oxazolyl, oxazoline, isoxazoline, oxetanyl, pyranyl, pyrazinyl, pyrazolyl, pyridazinyl, pyrido pyridyl, pyridazinyl, pyridyl, pyrimidyl, pyrazinyl, quinazolinyl, quinolinyl, quinoxalinyl, tetrahydropyranyl, tetrazolyl, tetrazolopyridyl, thiadiazolyl, thiazolyl, thienyl, triazolyl, azetidinyl, 1, 4-dioxanyl, hexallydroazepinyl, piperazinyl, piperidinyl, pyridine-2-keto, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolizinyl, dihydroisoxazolyl, dihydroisothiazolyl, dihydrooxadiazoly, dihydrooxazolyl, dihydropyrazinyl, dihydropyrazolyl, dihydropyridyl, dihydropyrimidinyl, dihydropyrrolidinyl, dihydroquinolyl, dihydrotetrazolyl, dihydrothiadiazolyl, dihydrothiazolyl, dihydrothienyl, dihydrotrizolyl, dihydro-azetidinyl, methylenedioxybenzoyl, tetrahydrofuryl and tetrahydrothienyl, and N-oxides thereof. The linkage of a "heterocyclyl" substituent may be achieved by a carbon atom or a heteroatom.

As a preferred embodiment, the "heterocyclyl" of the present disclosure is 2-azaprocone, benzimidazolyl, 2-diazeprazone, imidazolyl, 2-imidazolidinone, indolyl, isoquinolyl, morpholinyl, piperidinyl, piperazinyl, pyridyl, pyrrolidinyl, 2-piperidone, 2-pyrimidone, 2-pyrrolidone, quinolinyl, tetrahydrofuryl, tetrahydroisoquinolyl or thienyl.

The term "halogen" of the present disclosure means chlorine, fluorine, bromine and iodine.

Unless otherwise defined, the alkyl, alkenyl, alkynyl, cycloalkyl, aryl, heteroaryl and heterocyclyl substituents of the present disclosure may be unsubstituted or substituted. For example, a $C_3$-$C_6$ alkyl may be substituted with one, two or three substituents selected from OH, oxo, halogen, alkoxy, dialkylamino or heterocyclyl (e.g., morpholinyl or piperidinyl). In this case, if one substituent is oxo and the other is OH, the definition includes the following examples: —(C=O) $CH_2$ CH (OH) $CH_3$, —(C=O) OH, —$CH_2$ OH) $CH_2$CH (O) and the like.

The present disclosure includes the free form of the compound of formula (I), as well as its pharmaceutically acceptable salt or stereoisomer or prodrug molecule. Some of the specific exemplary compounds of the present disclosure are protonated salts of amine compounds. The term "free form" refers to an amine compound in a non-salt form. The pharmaceutically acceptable salt includes not only exemplary salt of the particular compound described herein but also typical pharmaceutically acceptable salts of all compounds of formula (I) in free form. The free form of specific salt of the compound can be isolated using techniques known in the art. For example, the free form may be regenerated by treating the salt with a suitable dilute aqueous solution of a base, such as dilute aqueous dilution of NaOH, dilute aqueous solution of potassium carbonate, dilute aqueous ammonia and dilute aqueous solution of sodium hydrogencarbonate. In certain physical properties, the free form is somewhat different from its salt form, such as solubility in a polar solvent, but the acid salt and base salt for the purposes of the present disclosure are comparable in other pharmaceutical form to its free form.

The pharmaceutically acceptable salt of the present disclosure can be synthesized from the compound of the present disclosure containing a basic or acidic moiety by conventional chemical processes. Typically, a salt of the basic compound is prepared by ion exchange chromatography or by reaction of a free base and a stoichiometric or excess amount of an inorganic or organic acid in the form of a salt in a suitable solvent or combination of a plurality of solvents. Similarly, a salt of acidic compound is formed by reaction with an appropriate inorganic or organic base.

Thus, the pharmaceutically acceptable salt of the compound of the present disclosure includes a conventional non-toxic salt of the compound of the present disclosure formed by the reaction of a basic compound of the disclosure with an inorganic or organic acid. For example, a conventional non-toxic salt includes a salt prepared from an inorganic acid such as hydrochloric acid, hydrobromic acid, sulfuric acid, sulfamic acid, phosphoric acid, nitric acid and the like, as well as a salt prepared from an organic acid such as acetic acid, propionic acid, succinic acid, glycolic acid, stearic acid, lactic acid, malic acid, tartaric acid, citric acid, ascorbic acid, picric acid, maleic acid, hydroxymaleic acid, phenylacetic acid, glutamic acid, benzoic acid, salicylic acid, p-aminobenzenesulfonic acid, 2-acetoxy-benzoic acid, fumaric acid, toluenesulfonic acid, methanesulfonic acid, ethane disulfonic acid, oxalic acid, isethionic acid, trifluoroacetic acid and the like.

If the compound of the present disclosure is acidic, the suitable "pharmaceutically acceptable salt" refers to a salt prepared by a pharmaceutically acceptable non-toxic base, including an inorganic and organic base. For example, a conventional non-toxic salt includes a salt derived from an inorganic base including aluminum salt, ammonium salt, calcium salt, copper salt, iron salt, ferrous salt, lithium salt, magnesium salt, manganese salt, manganous salt, potassium salts, sodium salt, zinc salt and the like. Particularly preferred are ammonium salt, calcium salt, magnesium salt, potassium salt and sodium salt. The conventional non-toxic salt includes a salt derived from a pharmaceutically acceptable organic non-toxic base which includes a salt of primary, secondary and tertiary amine, substituted amines including naturally occurring substituted amines, cyclic amines and basic ion exchange resins such as, Arginine, betaine, caffeine, choline, N, N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, aminoglucose, histidine, hydroxypropylamine, isopropylamine, lysine, methylglucosamine, morpholine, piperazine, piperidine, guanza, polyamine resin, procaine, purine, theobromine, triethylamine, trimethylamine, tripropylamine, tromethamine and the like.

Compared with the prior art, the present disclosure has the following beneficial effects:

(1) The pyrazolo [1,5-a] pyridine compound of the present disclosure has good in vitro antituberculosis activity, and the minimum inhibitory concentration (MIC) of the compound is lower than 0.1 μg/mL and partially achieves 0.01 μg/mL, and has a strong inhibitory effect on the clinically selected multi-drug resistant tuberculosis (MDR-TB) strain. In an in vivo experiment, the pyrazolo[1,5-a] pyrideine compound of the present disclosure can effectively scavenge the infectious dose of H37Ra in a mouse body at 20 mg/kg/d does, thereby being a new type of antituberculosis compound.

(2) The pyrazolo [1,5-a] pyridine compound of the present disclosure has good pharmacokinetic properties and very low side effects, has good pharmacological properties, is effective in vivo, and has a good development prospects.

DETAILED DESCRIPTION

Figure 1:
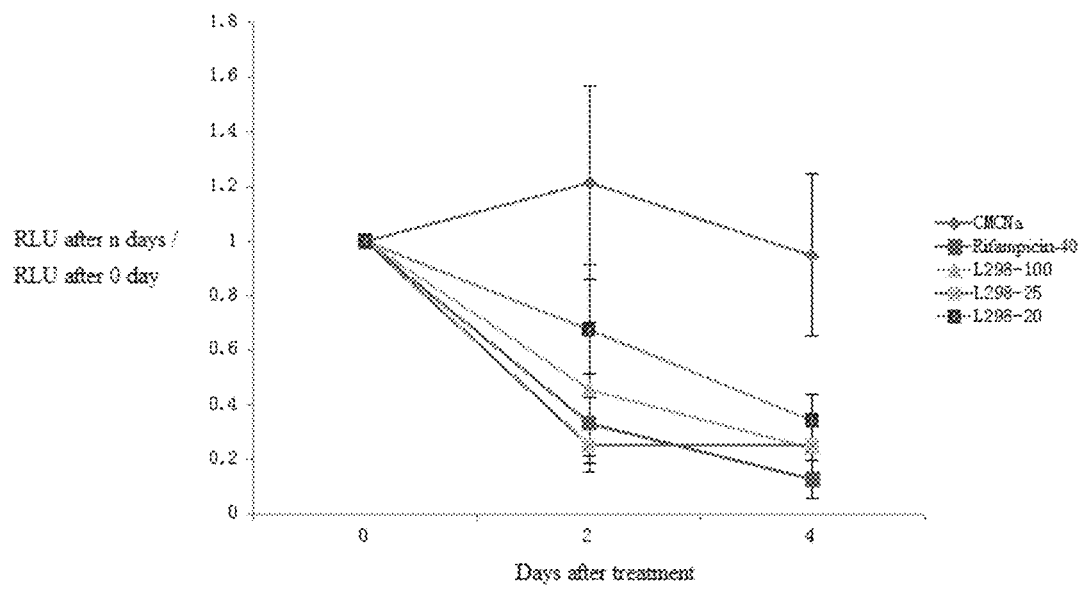
FIG. 1 shows the results of the real-time in vivo anti-tuberculosis activity assay of the compound L298.

According to standard pharmaceutical techniques, the compound of the present disclosure may be administered to a mammal, preferably a human, either alone or in combination with a pharmaceutically acceptable carrier in a pharmaceutical composition. The compound can be administered orally, subcutaneously, intramuscularly, intraperitoneally, intravenously, rectally, locally.

Formulations for oral administration may be such as tablets, lozenges, pastilles, water or oil suspensions, dispersible powders or granules, emulsions, hard capsules or soft capsules, or syrups or elixirs, and the like. Formulations for subcutaneous, intramuscular, intraperitoneal, and intravenous adminatration may be prepared as sterile injectable aqueous solutions. Formulations for rectal administration may be prepared as suppository forms. Formulations for local administration may be prepares as creams, ointments, gelling agents, solutionsor suspensions and the like.

The pharmaceutically acceptable carrier may for example be inert diluents such as calcium carbonate, sodium carbonate, lactose, calcium phosphate or sodium phosphate; granulating and disintegrating agents such as microcrystalline cellulose, sodium crosscarmellose, corn starch or alginic acid; binders such as starch, gelatin, polyvinylpyrrolidone or acacia; and lubricants such as magnesium stearate, stearic acid or talcum powder. The tablets may not be coated or coated by known techniques to mask the undesirable taste of the drug or to prolong the disintegration and absorption in the gastrointestinal tract and thus to provide a prolonged drug effect. For example, a water-soluble raw material for masking taste such as hydroxypropyl-methylcellulose or hydroxypropylcellulose may be used, or a delayed raw material such as ethylcellulose, cellulose acetate butyrate may be used.

The pyrazolo [1,5-a] pyridine compound of the present disclosure and the use thereof are further described below with reference to the accompanying drawings and specific examples.

Example 1: 5-chloro-2-ethyl-N-(4-(4-(4-(trifluoromethoxy) phenyl) piperidine-1-yl) benzyl) pyrazolo [1,5-a]pyridine-3-carboxamide (TJ170298)

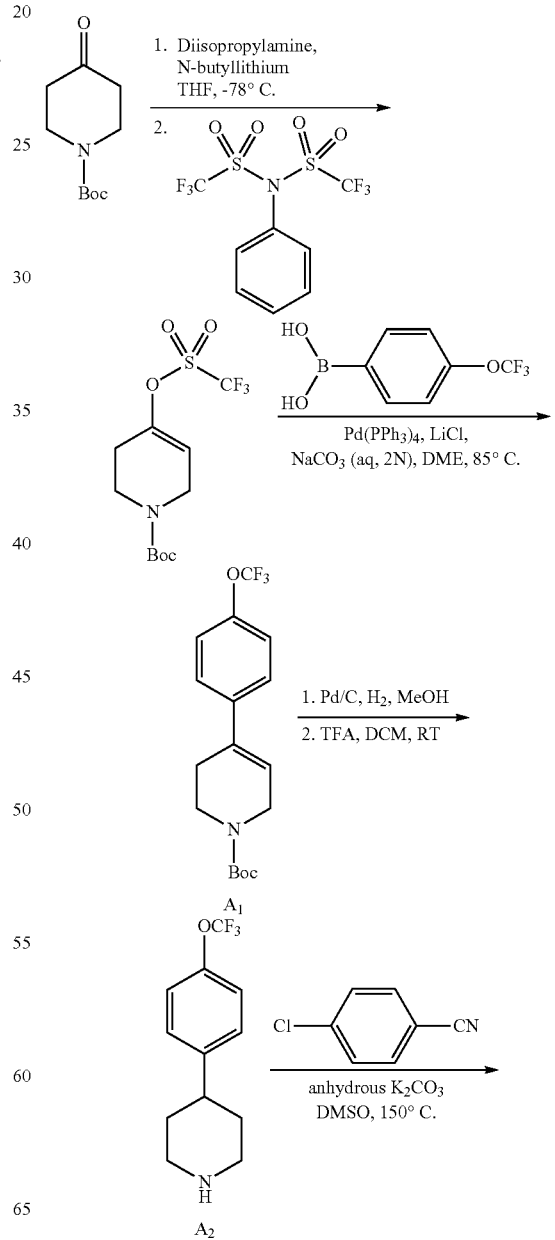

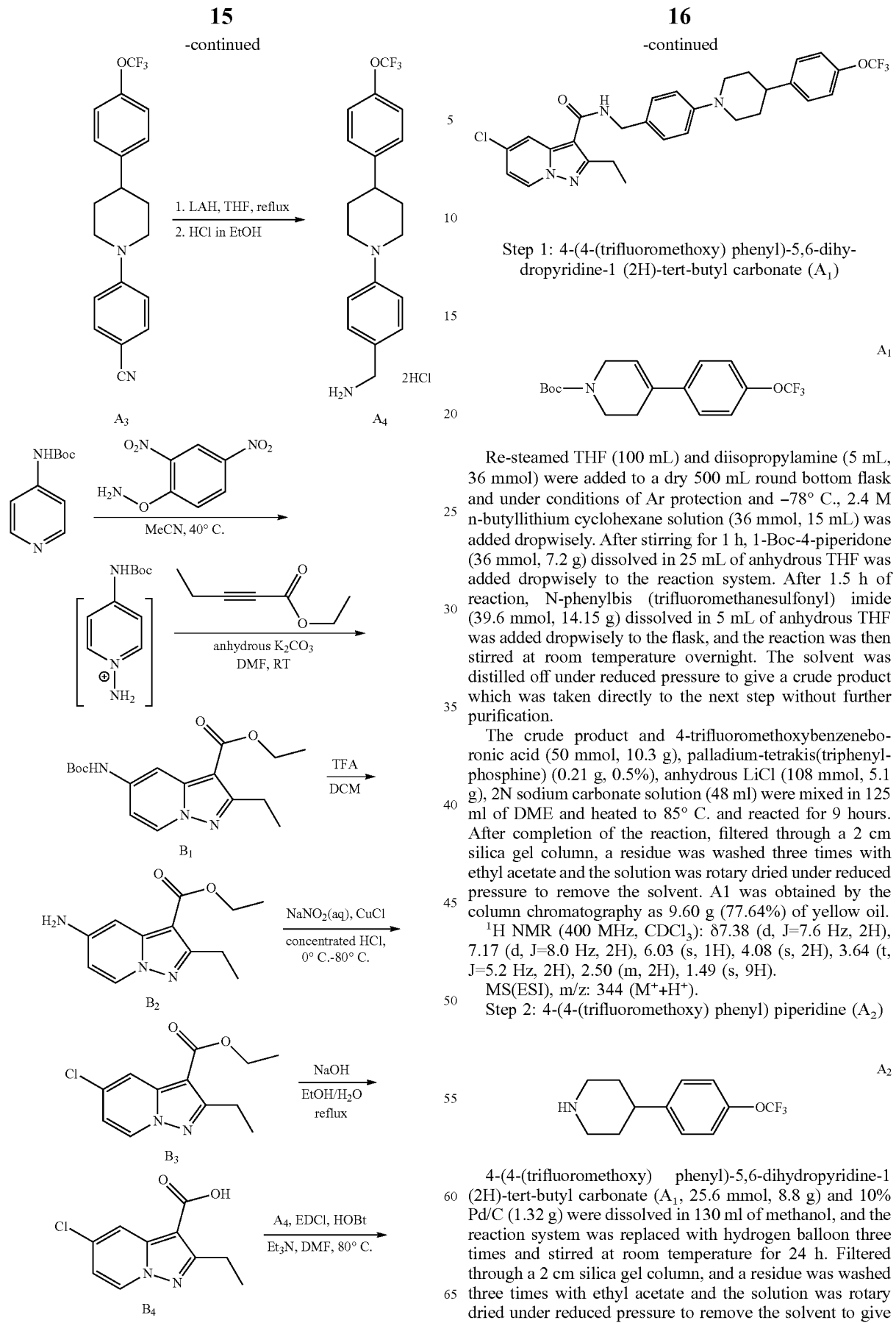

Step 1: 4-(4-(trifluoromethoxy) phenyl)-5,6-dihydropyridine-1 (2H)-tert-butyl carbonate (A₁)

Re-steamed THF (100 mL) and diisopropylamine (5 mL, 36 mmol) were added to a dry 500 mL round bottom flask and under conditions of Ar protection and −78° C., 2.4 M n-butyllithium cyclohexane solution (36 mmol, 15 mL) was added dropwisely. After stirring for 1 h, 1-Boc-4-piperidone (36 mmol, 7.2 g) dissolved in 25 mL of anhydrous THF was added dropwisely to the reaction system. After 1.5 h of reaction, N-phenylbis (trifluoromethanesulfonyl) imide (39.6 mmol, 14.15 g) dissolved in 5 mL of anhydrous THF was added dropwisely to the flask, and the reaction was then stirred at room temperature overnight. The solvent was distilled off under reduced pressure to give a crude product which was taken directly to the next step without further purification.

The crude product and 4-trifluoromethoxybenzeneboronic acid (50 mmol, 10.3 g), palladium-tetrakis(triphenylphosphine) (0.21 g, 0.5%), anhydrous LiCl (108 mmol, 5.1 g), 2N sodium carbonate solution (48 ml) were mixed in 125 ml of DME and heated to 85° C. and reacted for 9 hours. After completion of the reaction, filtered through a 2 cm silica gel column, a residue was washed three times with ethyl acetate and the solution was rotary dried under reduced pressure to remove the solvent. A1 was obtained by the column chromatography as 9.60 g (77.64%) of yellow oil.

$^1$H NMR (400 MHz, CDCl₃): δ7.38 (d, J=7.6 Hz, 2H), 7.17 (d, J=8.0 Hz, 2H), 6.03 (s, 1H), 4.08 (s, 2H), 3.64 (t, J=5.2 Hz, 2H), 2.50 (m, 2H), 1.49 (s, 9H).

MS(ESI), m/z: 344 (M⁺+H⁺).

Step 2: 4-(4-(trifluoromethoxy) phenyl) piperidine (A₂)

4-(4-(trifluoromethoxy) phenyl)-5,6-dihydropyridine-1 (2H)-tert-butyl carbonate (A₁, 25.6 mmol, 8.8 g) and 10% Pd/C (1.32 g) were dissolved in 130 ml of methanol, and the reaction system was replaced with hydrogen balloon three times and stirred at room temperature for 24 h. Filtered through a 2 cm silica gel column, and a residue was washed three times with ethyl acetate and the solution was rotary dried under reduced pressure to remove the solvent to give yellow oil. The oil was further dissolved in anhydrous DCM (150 mL), TFA (70 mL) was slowly added under ice bath, and stirred at room temperature overnight. The solution was rotary dried under reduced pressure to remove the solvent, and the solute left behind was dissolved in ethyl acetate, and then saturated solution of sodium bicarbonate was added until pH of the aqueous phase was equal to 8.0. The organic phase was separated and the aqueous phase was extracted three times with ethyl acetate. The organic phases were combined and the solution was rotary dried under reduced pressure to remove the solvent to give $A_2$, 6.3 g (100%) of a brown viscous solid.

MS(ESI), m/z: 246 (M$^+$+H$^+$).

Step 3: 4-(4-(4-(trifluoromethoxy) phenyl) piperidine-1-yl) benzonitrile ($A_3$)

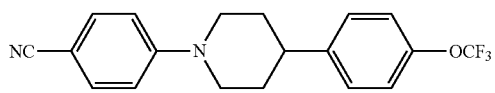

4-(4-(trifluoromethoxy) phenyl) piperidine ($A_2$, 6.56 mmol, 1.61 g), 4-chlorobenzonitrile (32.8 mmol, 4.5 g) and anhydrous potassium carbonate (13.12 mmol, 1.8 G) were dissolved in 40 mLDMSO and heated to 150° C. overnight. The mixture was cooled to room temperature and a large amount of water was added. The precipitated solid was filtered without a funnel. The residue was washed three times with water and then dissolved in ethyl acetate and dried over anhydrous sodium sulfate. $A_3$ was obtained by as the column chromatography as 1.70 g (74.6%) of a white solid.

MS(ESI), m/z: 347 (M$^+$+H$^+$).

Step 4: (4-(4-(4-(trifluoromethoxy) phenyl) piperidine-1-yl) phenyl) methanamine hydrochloride $A_4$

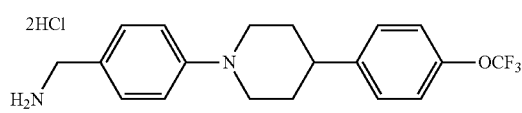

4-(4-(trifluoromethoxy) phenyl) piperidine-1-yl) benzonitrile ($A_3$, 4.9 mmol, 1.7 g) was dissolved in anhydrous THF (110 mL), under ice bath, LAH (15.2 mmol, 0.58 g) was added and stirred for half an hour and heated to reflux overnight. The reaction was cooled, under ice bath conditions a lot of water was slowly added to quench the reaction. Filtered through a 2 cm silica gel column, the residue was washed three times with ethyl acetate and the solution was rotary dried under reduced pressure to remove the solvent. An excess of hydrogen chloride ethanol solution was added to make it salt, and the solvent was rotary dried to obtain $A_4$ as 2.02 g (97.2%) of a solid.

MS(ESI), m/z: 351 (M$^+$).

Step 5: 2-ethyl-5-((tert-butoxycarbonyl) amine)-pyrazolo [1,5-a] pyridine-3-ethyl carbonate $B_1$

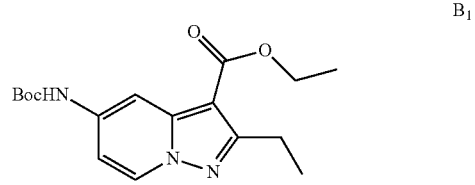 [SMILES: CCOC(=O)c1c(CC)nn2ccc(NC(=O)OC(C)(C)C)cc12]

4-(tert-butoxycarbonylamino) pyridine (1.2 g, 6.2 mmol) and 2,4-dinitrohydroxylamine (DNPH, 1.23 g, 6.2 mmol) were dissolved in 28 mL of acetonitrile, and the temperature was increased to 40° C. After 18 h of the reaction, the solution was rotary dried to remove the solvent. Anhydrous DMF (15 mL), ethyl 2-pentynoate (0.78 g, 6.2 mmol) and anhydrous $K_2CO_3$ (1.71 g, 12.4 mmol) were added to the reaction system. The reaction system was stirred overnight at room temperature, and the reaction was completed as detected by TLC. A large amount of water was added and extracted three times with ethyl acetate. The organic phase was collected and then washed three times with brine and separated by column chromatography to give a product $B_1$, 0.71 g (34.2%).

MS(ESI), m/z: 334 (M$^+$+H$^+$).

Step 6: 2-ethyl-5-amino-pyrazolo [1,5-a] pyridine-3-ethyl carbonate $B_2$

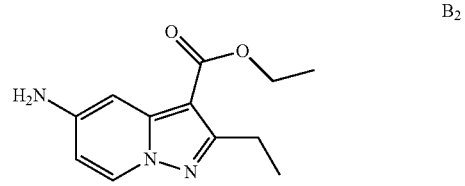 [SMILES: CCOC(=O)c1c(CC)nn2ccc(N)cc12]

2-ethyl-5-((tert-butoxycarbonyl) amine)-pyrazolo [1,5-a] pyridine-3-ethyl carbonate ($B_1$, 0.69 g, 2.07 mmol) was dissolved in 28 mL of anhydrous DCM, and 1.8 mL of TFA was added dropwisely. Stirred overnight at room temperature, rotary dried, and NaHCO$_3$ saturated solution was added until pH=7-8. After extraction three times with ethyl acetate, the organic phase was dried with anhydrous sodium sulfate, collected and rotary dried to give a product $B_2$, 0.36 g (75%).

MS(ESI), m/z: 234 (M$^+$+H$^+$).

Step 7: 2-ethyl-5-chloro-pyrazolo [1,5-a] pyridine-3-ethyl carbonate $B_3$

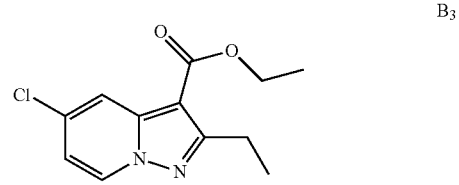 [SMILES: CCOC(=O)c1c(CC)nn2ccc(Cl)cc12]

2-ethyl-5-amino-pyrazolo [1,5-a] pyridine-3-ethyl carbonate (B₂, 0.1 g, 0.43 mmol) and CuCl (0.11 g, 1.1 mmol) were dissolved in concentrated hydrochloric acid (1.5 mL). 0.4 M NaNO₂ solution (0.038 g, 0.56 mmol) was slowly added dropwisely under ice bath conditions. After half an hour, the reaction system was heated to 80° C. and the reaction was completed after 15 min of reaction as detected by TLC. The reaction was cooled, 1 M NaOH solution was added until pH was equal to 10. Filtered through a 2 cm silica gel column, the residue was washed three times with ethyl acetate and the solution was rotary dried under reduced pressure. A product B₃ 0.08 g (73.8%) was isolated by the column chromatography.

MS(ESI), m/z: 253 (M⁺+H⁺).

Step 8: 2-ethyl-5-chloro-pyrazolo [1,5-a] pyridine-3-carboxylic acid B₄

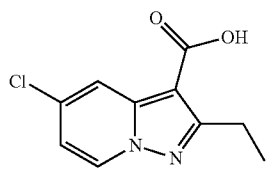

2-ethyl-5-chloro-pyrazolo [1,5-a] pyridine-3-ethyl carbonate (B₃, 0.27 g, 1.07 mmol) was dissolved in a mixed solvent of 9 mL of ethanol and 3 mL of water, NaOH (0.13 g, 3.2 mmol) was added and heated to reflux overnight. The reaction was cooled, the solution was rotary dried to remove the solvent, 1N HCl was added to make pH of the system be equal to 4.0, and the precipitated solid was filtered by suction and dried in vacuum to give B₄ as 0.29 g (100%) of a solid.

MS(ESI), m/z: 225 (M⁺+H⁺).

Step 9: 5-chloro-2-ethyl-N-(4-(4-(4-(trifluoromethoxy) phenyl) piperidine-1-yl) benzyl [1,5-a] pyridine-3-carboxamide (TJ170298)

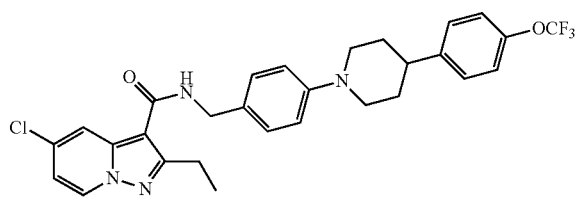 [SMILES: CCc1nn2ccc(Cl)cc2c1C(=O)NCc1ccc(N2CCC(c3ccc(OC(F)(F)F)cc3)CC2)cc1]

2-ethyl-5-chloro-pyrazolo [1,5-a] pyridine-3-carboxylic acid (B₄, 0.25 g, 1.1 mmol). EDCI.HCl (0.32 g, 1.65 mmol), HOBT (0.074 g, 0.55 mmol) were dissolved in DMF (20 mL), and triethylamine (0.66 g, 6.6 mmol) and the compound A₄ (0.55 g, 1.3 mmol) were added. The reaction was heated to 80° C. overnight. After the reaction was cooled, a large amount of water was added and extracted three times with ethyl acetate. The organic phase was collected and washed three times with brine and then TJ170298 as 0.46 g (74.7%) of a solid was isolated by the column chromatography.

¹H NMR (400 MHz, DMSO-d₆) δ8.72 (d, J=7.6 Hz, 1H), 8.17 (t, J=6.0 Hz, 1H), 7.90 (s, 1H), 7.41 (d, J=8.8 Hz, 1H), 7.28 (d, J=8.0 Hz, 2H), 7.22 (d, J=8.8 Hz, 2H), 7.02 (dd, J=7.2, 2.4 Hz, 1H), 6.95 (d, J=8.8 Hz, 2H), 4.39 (d, J=6.0 Hz, 2H), 3.78 (m, 2H), 3.00 (q, J=7.6 Hz, 2H), 2.73 (m, 3H), 1.86 (m, 2H), 1.74 (m, 2H), 1.24 (t, J=7.6 Hz, 2H).

MS(ESI), m/z: 557 (M⁺+H⁺).

Example 2: 5-chloro-2-ethyl-N-(4-(trifluoromethoxy) phenyl) pyrazolo [1,5-a] pyridine-3-carboxamide (TJ170322)

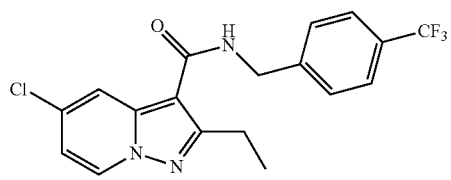 [SMILES: CCc1nn2ccc(Cl)cc2c1C(=O)NCc1ccc(C(F)(F)F)cc1]

The synthetic process was as described in steps 5 to 9 of Example 1.

¹H NMR (400 MHz, DMSO-d₆): δ8.74 (d, J=7.2 Hz, 1H), 8.32 (t, J=6.0 Hz, 1H), 7.96 (s, 1H), 7.71 (d, J=8.4 Hz, 2H), 7.57 (d, J=8.0 Hz, 2H), 7.04 (d, J=7.2 Hz, 1H), 4.57 (d, J=5.6 Hz, 2H), 3.02 (q, J=7.4 Hz, 2H), 1.25 (t, J=7.4 Hz, 2H).

MS(ESI), m/z: 382 (M⁺+H⁺).

Example 3: 5-chloro-N-(4-(4-(4-(trifluoromethoxy) phenyl) piperidine-1-yl) benzyl) pyrazolo [1,5-a] pyridine-3-carboxamide (TJ170371)

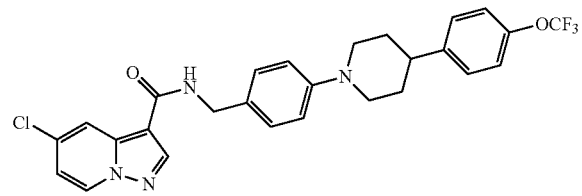 [SMILES: O=C(NCc1ccc(N2CCC(c3ccc(OC(F)(F)F)cc3)CC2)cc1)c1cnn2ccc(Cl)cc12]

The synthesis process was as described in Example 1.

¹H NMR (400 MHz, DMSO-d₆): δ8.82 (d, J=7.2 Hz, 1H), 8.72 (s 1H), 8.63 (s, 1H), 8.24 (s, 1H), 7.40 (d, J=8.4 Hz, 2H), 7.28 (d, J=8.0 Hz, 2H), 7.20 (d, J=8.0 Hz, 2H), 7.13 (d, J=7.2 Hz, 2H), 6.94 (d, J=8.0 Hz, 2H), 4.38 (d, J=5.2 Hz, 2H), 3.77 (m, 2H), 2.72 (m, 3H), 1.86 (m, 2H), 1.74 (m, 2H).

MS(ESI), m/z: 529 (M⁺+H⁺).

Example 4: 5-chloro-2-methyl-N-(4-(4-(4-(trifluoromethoxy) phenyl) piperidine-1-yl) benzyl) pyrazolo [1,5-a] pyridine-3-carboxamide (TJ170372)

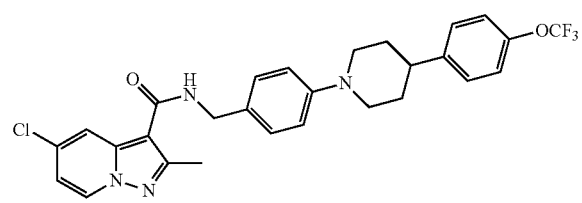 [SMILES: Cc1nn2ccc(Cl)cc2c1C(=O)NCc1ccc(N2CCC(c3ccc(OC(F)(F)F)cc3)CC2)cc1]

The synthesis process was as described in Example 1.

¹H NMR (400 MHz, DMSO-d₆): δ8.70 (d, J=6.0 Hz, 1H), 8.08 (t, J=4.4 Hz, 1H), 7.94 (s, 1H), 7.40 (d, J=6.8 Hz, 2H), 7.29 (d, J=6.8 Hz, 2H), 7.22 (d, J=6.8 Hz, 2H), 7.03 (d, J=6.0 Hz, 1H), 6.95 (d, J=6.8 Hz, 2H), 4.39 (d, J=4.4 Hz, 2H), 3.78 (m, 2H), 2.73 (m, 3H), 2.56 (s, 3H), 1.86 (m, 2H), 1.74 (m, 2H).

MS(ESI), m/z: 543 (M$^+$+H$^+$).

Example 5: 5-chloro-2-cyclopropyl-N-(4-(4-(4-(trifluoromethoxy) phenyl) piperidine-1-substituted) benzyl) pyrazolo [1,5-a] pyridine-3-carboxamide (TJ170375)

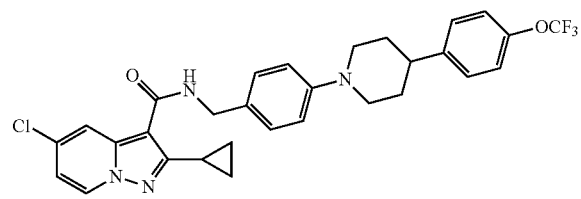 [SMILES: O=C(NCc1ccc(N2CCC(c3ccc(OC(F)(F)F)cc3)CC2)cc1)c1c(C2CC2)nn2ccc(Cl)cc12]

The synthesis process was as described in Example 1.

$^1$H NMR (500 MHz, DMSO-d$_6$): δ8.66 (d, J=7.0 Hz, 1H), 8.17 (s, 1H), 7.90 (s, 1H), 7.40 (d, J=8.0 Hz, 2H), 7.28 (d, J=8.0 Hz, 2H), 7.23 (d, J=8.0 Hz, 2H), 7.00 (d, J=6.5 Hz, 1H), 6.96 (d, J=8.0 Hz, 2H), 4.14 (d, J=5.5 Hz, 2H), 3.78 (m, 2H), 2.73 (m, 3H), 2.54 (m, 3H), 1.86 (m, 2H), 1.74 (m, 2H), 1.02 (m, 2H), =0.96 (s, 2H).

MS(ESI), m/z: 569 (M$^+$+H$^+$).

Example 6: 2-methyl-N-(4-(4-(4-(trifluoromethoxy) phenyl) piperidine-1-yl) benzyl) pyrazolo [1,5-a] pyridine-3-carboxamide (TJ170381)

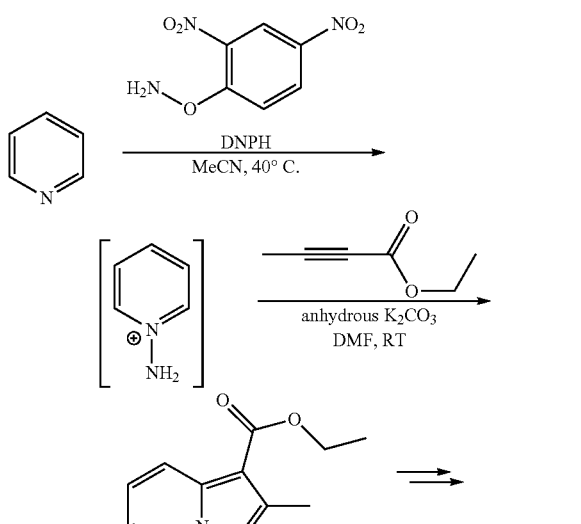

Step 1: 2-methylpyrazolo [1,5-a] pyridine-3-ethyl carbonate

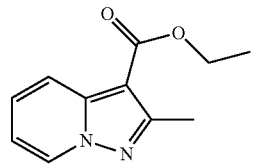

Pyridine (0.36 g, 4.5 mmol) and 2,4-dinitrohydroxylamine (DNPH, 1.0 g, 5 mmol) were dissolved in 25 mL of acetonitrile and heated to 40° C. After 18 h of reaction, the solution was rotary dried to remove the solvent. Then anhydrous DMF (25 mL), ethyl 2-butynoate (0.75 g, 6.75 mmol) and anhydrous K$_2$CO$_3$ (1.24 g, 9 mmol) were added to the reaction system. After stirring overnight at room temperature, the reaction was completed as detected by TLC. A large amount of water was added and extracted three times with ethyl acetate. The organic phase was collected and washed three times with brine and separated by column chromatography to give 0.53 g (57.27%) of a solid.

$^1$H NMR (400 MHz, CDCl$_3$): δ8.46 (d, J=6.8 Hz, 1H), 8.10 (d, J=8.8 Hz, 1H), 7.38 (t, J=7.8 Hz, 1H), 6.90 (t, J=6.6 Hz, 2H), 4.39 (q, J=6.8 Hz, 2H), 2.69 (s, 3H), 1.43 (t, J=7.0 Hz, 3H).

MS(ESI), m/z: 205 (M$^+$+H$^+$).

Step 2: 2-methyl-N-(4-(4-(4-(trifluoromethoxy) phenyl) piperidine-1-yl) benzyl) pyrazolo [1,5-a] pyridine-3-carboxamide (TJ170381)

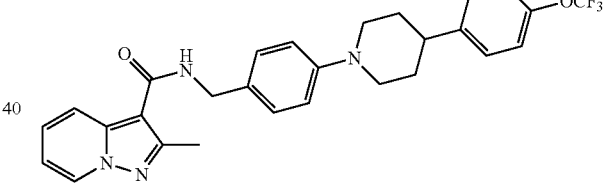

The synthesis process was as described in steps 8 and 9 of Example 1.

$^1$H NMR (400 MHz, DMSO-d$_6$): δ8.64 (d, J=6.8 Hz, 1H), 8.01 (s, 1H), 7.90 (d J=8.8 Hz, 1H), 7.40 (m, 3H), 7.28 (d, J=8.0 Hz, 2H), 7.23 (d, J=8.0 Hz, 2H), 6.95 (m, 3H), 4.40 (d, J=5.2 Hz, 2H), 3.78 (d, J=11.6 Hz, 2H), 2.73 (m, 3H), 2.56 (s, 3H), 1.86 (m, 2H), 1.74 (m, 2H).

MS(ESI), m/z: 509 (M$^+$+H$^+$).

Example 7: 2,5-dimethyl-N-(4-(4-(4-(trifluoromethoxy) phenyl) piperidine-1-yl) benzyl) pyrazolo [1,5-a] pyridine-3-carboxamide (TJ170385)

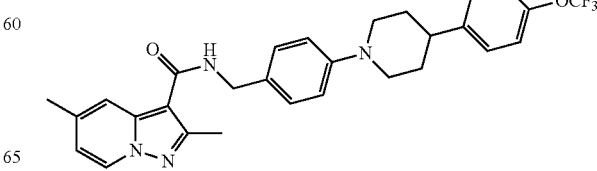

The synthesis process was as described in Example 6.

¹H NMR (400 MHz, DMSO-d₆): δ8.52 (d, J=7.2 Hz, 1H), 7.90 (t, J=6.0 Hz, 1H), 7.71 (s, 1H), 7.40 (d, J=8.4 Hz, 2H), 7.28 (d, J=8.0 Hz, 2H), 7.22 (d, J=8.4 Hz, 2H), 6.95 (d, J=8.4 Hz, 2H), 6.80 (d, J=6.8 Hz, 1H), 4.39 (d, J=5.6 Hz, 2H), 3.78 (m, 2H), 2.73 (m, 3H), 2.53 (s, 3H), 2.37 (s, 3H), 1.86 (m, 2H), 1.75 (m, 2H).

MS(ESI), m/z: 523 (M⁺+H⁺).

Example 8: 5-chloro-2-phenyl-N-(4-(4-(4-(trifluoromethoxy) phenyl)

piperidine-1-yl) benzyl) pyrazolo [1,5-a] pyridine-3-carboxamide (TJ170386)

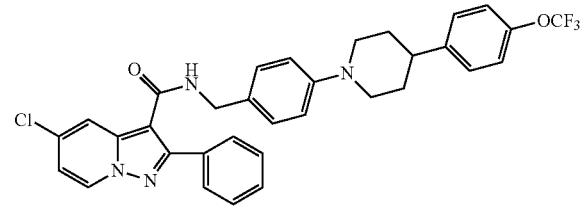 [SMILES: O=C(NCc1ccc(N2CCC(c3ccc(OC(F)(F)F)cc3)CC2)cc1)c1c(-c2ccccc2)nn2ccc(Cl)cc12]

The synthesis process was as described in Example 6.

¹H NMR (400 MHz, DMSO-d₆): δ8.32 (s, 1H), 7.42 (m, 3H), 7.41 (m, 5H), 7.29 (d, J=8.0 Hz, 2H), 7.18 (d, J=8.0 Hz, 1H), 7.10 (d, J=6.4 Hz, 1H), 6.96 (d, J=8.4 Hz, 2H), 4.35 (d, J=5.2 Hz, 2H), 3.80 (m, 2H), 2.75 (m, 3H), 1.87 (m, 2H), 1.76 (m, 2H).

MS(ESI), m/z: 605 (M⁺+H⁺).

Example 9: 4-((5-chloro-2-ethylpyrazolo [1,5-a] pyridine-3-carboxamide) methyl) methyl benzoate (TJ064814)

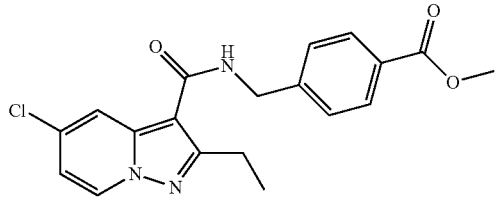 [SMILES: CCc1nn2ccc(Cl)cc2c1C(=O)NCc1ccc(C(=O)OC)cc1]

The synthesis process was as described in steps 5 to 9 of Example 1.

¹H NMR (400 MHz, DMSO-d₆): δ 8.75 (d, J=7.6 Hz, 1H), 8.33 (t, J=5.4 Hz, 1H), 7.94 (m, 3H), 7.48 (d, J=7.6 Hz, 2H), 7.03 (d, J=7.2 Hz, 1H), 4.56 (d, J=5.6 Hz, 2H), 3.84 (s, 3H), 3.01 (q, J=7.6 Hz, 2H), 1.24 (t, J=7.2 Hz, 2H).

MS(ESI), m/z: 372 (M⁺+H⁺).

Example 10: 5-chloro-2-ethyl-N-(4-(4-(4-(trifluoromethoxy) phenyl)

piperidine-1-yl) phenyl) pyrazolo [1,5-a] pyridine-3-carboxamide (TJ064819)

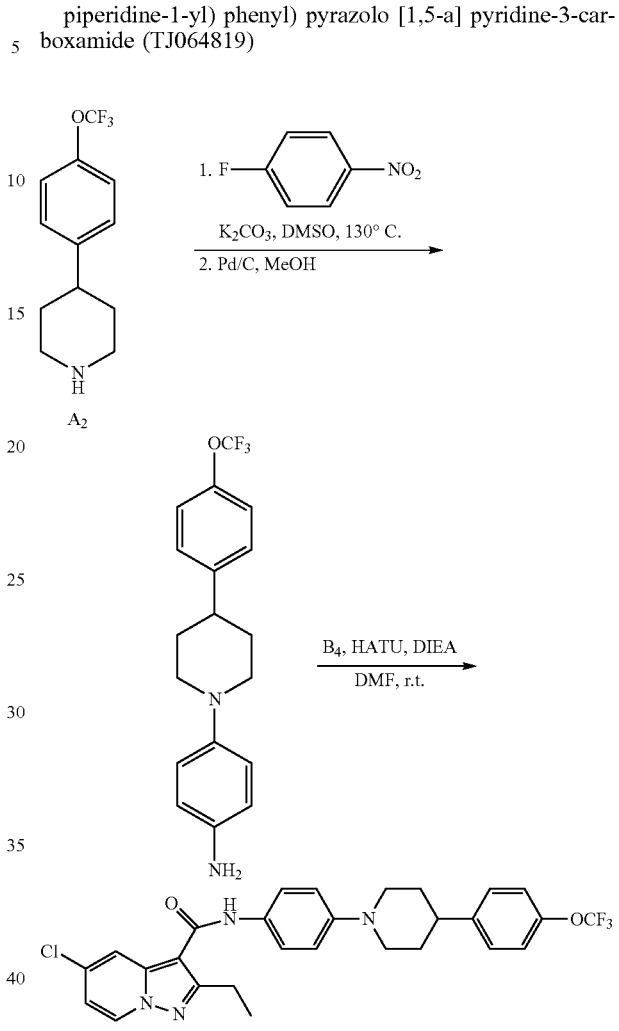

Step 1: 4-(4-(4-(trifluoromethoxy) phenyl) piperidine-1-yl) aniline

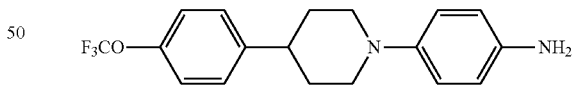

Intermediate A₂ (0.5 g, 2 mmol) was dissolved in DMSO (12 mL) and anhydrous K₂CO₃ (0.55 g, 4 mmol) and p-fluoronitrobenzene (0.56 g, 4 mmol) were added. The temperature was raised to 130° C. and the reaction was carried out overnight. Cool to room temperature, add a lot of water, the precipitated solid was filtered by suction with a Buchner funnel, and washed three times with water, and the residue was dissolved in ethyl acetate, then washed three times with water. The organic phase was dried over anhydrous sodium sulfate and purified by column chromatography to give 0.68 g (92.0%) of a intermediate 1-(4-nitrobenzene)-4-(4-(trifluoromethoxy) phenyl) piperidine.

The resulting intermediate, 1-(4-nitrobenzene)-4-(4-(trifluoromethoxy) phenyl) piperidine (0.68 g, 1.86 mmol) was dissolved in MeOH (30 mL), and a catalytic amount of Pd/C was added. After replaced three times with hydrogen, the mixture was stirred at room temperature for 7 h. After completion of the reaction, filtered through a 2 cm silica gel column, the residue was washed three times with ethyl acetate and the solution was rotary dried under reduced pressure to remove the solvent. 0.44 g (70.9%) of 4-(4-(4-(trifluoromethoxy) phenyl) 1-yl) aniline was isolated by column chromatography.

MS(ESI), m/z: 337 (M$^+$+H$^+$).

Step 2: 5-chloro-2-ethyl-N-(4-(4-(4-(trifluoromethoxy) phenyl) piperidine-1-yl) phenyl) pyrazolo[1,5-a] pyridine-3-carboxamide (TJ064819)

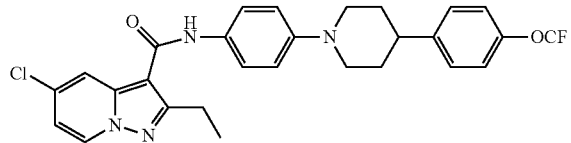

The intermediate B$_4$ (0.15 g, 0.67 mmol) was dissolved in DMF (10 mL), and HATU (0.38 g, 1.0 mmol) and DIEA (0.26 g, 2.0 mmol) were added. After stirring at room temperature for half an hour, the intermediate 4-(4-(4-(trifluoromethoxy) phenyl) piperidine-1-yl) aniline (0.27 g, 0.8 mmol) was added. After stirring overnight at room temperature, the reaction was completed as detected by TLC, then a lot of water was added. The precipitated solid was filtered by suction through a Buchner funnel, washed three times with water, and the residue was dissolved in ethyl acetate. After washing three times with brine, the solution was rotary dried under reduced pressure to remove the solvent and 94 mg (26.0%) of a product TJ064819 was isolated by column chromatography.

$^1$H NMR (400 MHz, DMSO-d$_6$): δ9.64 (s, 1H), 8.77 (d, J=7.2 Hz, 1H), 7.84 (s, 1H), 7.54 (d, J=8.8 Hz, 2H), 7.43 (d, J=8.4 Hz, 2H), 7.30 (d, J=8.0 Hz, 2H), 7.05 (d, J=7.2 Hz, 1H), 6.98 (d, J=8.8 Hz, 2H), 3.76 (m, 2H), 3.02 (q, J=7.6 Hz, 2H), 2.73 (m, 3H), 1.88 (m, 2H), 1.78 (m, 2H), 1.27 (t, J=7.6 Hz, 3H).

MS(ESI), m/z: 543 (M$^+$+H$^+$).

Example 11: 2,7-dimethyl-N-(4-(4-(4-(trifluoromethoxy) phenyl) piperidine-1-yl) benzyl) pyrazolo[1,5-a] pyridine-3-carboxamide (TJ064851)

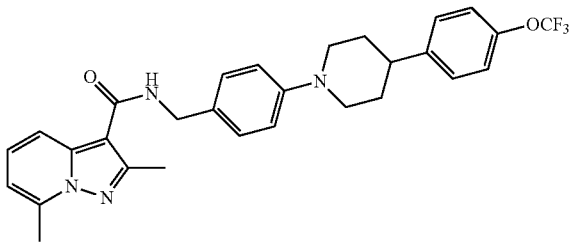 [SMILES: Cc1nn2c(C)cccc2c1C(=O)NCc1ccc(N2CCC(c3ccc(OC(F)(F)F)cc3)CC2)cc1]

The synthesis process was as described in Example 6.
$^1$H NMR (400 MHz, DMSO-d$_6$): δ7.98 (s, 1H), 7.82 (d, J=8.8 Hz, 1H) 7.40 (d, J=8.4 Hz, 2H), 7.31 (m, 3H), 7.23 (d, J=8.4 Hz, 2H), 6.95 (d, J=8.4 Hz, 2H), 6.88 (d, J=6.8 Hz, 1H), 4.40 (d, J=6.0 Hz, 2H), 3.78 (m, 2H), 2.73 (m, 3H), 2.66 (s, 3H), 2.60 (s, 3H), 1.86 (m, 2H), 1.73 (m, 2H).
MS(ESI), m/z: 523 (M$^+$+H$^+$).

Example 12: 2,6-dimethyl-N-(4-(4-(4-(trifluoromethoxy) phenyl) piperidine-1-yl) benzyl) pyrazolo[1,5-a] pyridine-3-carboxamide (TJ064854)

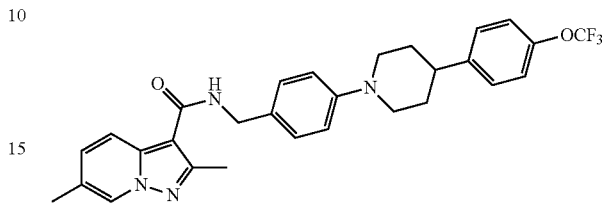

The synthesis process was as described in Example 6.
$^1$H NMR (400 MHz, DMSO-d$_6$): δ8.48 (s, 1H), 7.93 (s, 1H), 7.83 (d, J=8.8 Hz, 1H), 7.40 (d, J=8.0 Hz, 2H), 7.25 (m, 5H), 6.95 (d, J=8.0 Hz, 2H), 4.39 (d, J=4.8 Hz, 2H), 3.78 (d, J=11.2.0 Hz, 2H), 2.73 (m, 3H), 2.54 (s, 3H), 2.30 (s, 3H), 1.86 (m, 2H), 1.76 (m, 2H). MS(ESI), m/z: 523 (M$^+$+H$^+$).

Example 13: 2,4-dimethyl-N-(4-(4-(4-(trifluoromethoxy) phenyl) piperidine-1-yl) benzyl) pyrazolo[1,5-a] pyridine-3-carboxamide (TJ064872)

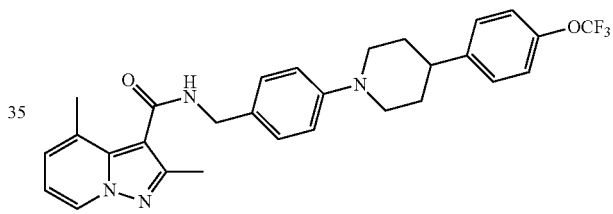

The synthesis process was as described in Example 6.
$^1$H NMR (400 MHz, DMSO-d$_6$): δ8.57 (s, 1H), 8.44 (d, J=7.2 Hz, 1H), 7.41 (d, J=8.4 Hz, 2H), 7.29 (d, J=8.4 Hz, 2H), 7.22 (d, J=8.4 Hz, 2H), 7.03 (d, J=6.8 Hz, 1H), 6.96 (d, J=8.4 Hz, 2H), 6.80 (t, J=7.0 Hz, 2H), 4.38 (d, J=6.0 Hz, 2H), 3.80 (m, 2H), 2.74 (m, 3H), 2.39 (s, 3H), 2.37 (s, 3H), 1.87 (m, 2H), 1.76 (m, 2H).
MS(ESI), m/z: 523 (M$^+$+H$^+$).

Example 14: 5-methoxy-2-ethyl-N-(4-(4-(4-(trifluoromethoxy) phenyl) piperidine-1-substituted) benzyl) pyrazolo[1,5-a] pyridine-3-carboxamide (TJ064889)

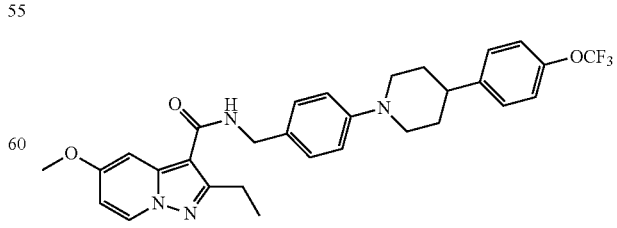

The synthesis process was as described in Example 6.
$^1$H NMR (400 MHz, DMSO-d$_6$): δ8.51 (d, J=7.6 Hz, 1H), 7.90 (t, J=6.0 Hz, 1H), 7.41 (d, J=8.8 Hz, 2H), 7.28 (d, J=8.4

Hz, 2H), 7.22 (d, J=8.8 Hz, 2H), 7.19 (d, J=2.8 Hz, 1H), 6.95 (d, J=8.8 Hz, 2H), 6.62 (dd, J=7.4, 2.6 Hz, 1H), 4.40 (d, J=5.6 Hz, 2H), 3.85 (s, 3H), 3.78 (m, 2H), 2.94 (q, J=7.6 Hz, 2H), 2.72 (m, 3H), 1.86 (m, 2H), 1.75 (m, 2H), 1.23 (t, J=7.6 Hz, 3H).

MS(ESI), m/z: 553 (M$^+$+H$^+$).

Example 15: 5-chloro-2-ethyl-N-((1-(4-(trifluoromethoxy) phenyl)-1H-1,2,3-triazolyl-4-yl) pyrazolo [1,5-a] pyridine-3-carboxamide (TJ064983)

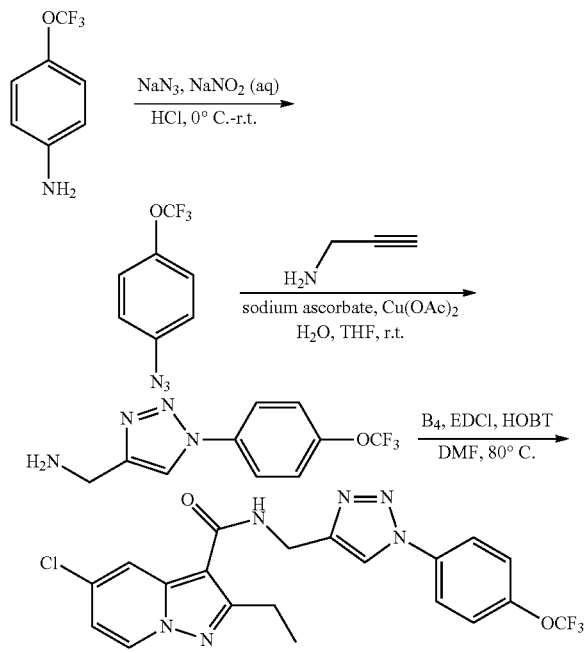

Step 1: (1-(4-(trifluoromethoxy) phenyl)-1H-1,2,3-triazole-4-yl) methylamine

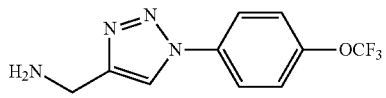

4-trifluoromethoxyaniline (1.3 g, 7.34 mmol) was dissolved in a mixed solution of water (32 mL) and concentrated hydrochloric acid (1.25 mL). Under ice bath, NaNO$_2$ aqueous solution (0.92 M, 7.36 mmol) was slowly added dropwisely to the system. After stirring for 10 min, NaN$_3$ aqueous solution (1.1 M, 8 mL) was slowly added dropwisely. After continuing stirring for 45 min, the temperature was raised to room temperature to continue stirring for 1 h. The extraction was carried out three times with ethyl acetate, after the reaction was completed as detected by TLC. The organic phase was collected and dried over anhydrous sodium sulfate and rotary dried under reduced pressure to give an oil which did not require further purification.

The oil was dissolved in tetrahydrofuran (27 mL), and propargylamine (0.44 g, 8.07 mmol) and water (13.5 mL) were added. An aqueous solution (13.5 mL) of sodium ascorbate (30 mg, 0.15 mmol) and Cu (OAc)$_2$.H$_2$O (14 mg, 0.075 mmol) was added to the reaction system. After stirring at room temperature for 12 h, a brine was added. After extracting three times with dichloromethane, the organic phase was isolated by column chromatography to give a product (1-(4-(trifluoromethoxy) phenyl)-1H-1,2, 3-triazole-4-yl) methylamine, 0.19 g (total yield of 10.1% in two steps).

MS(ESI), m/z: 259 (M$^+$+H$^+$).

Step 2: 5-chloro-2-ethyl-N-((1-(4-(trifluoromethoxy) phenyl)-1H-1,2,3-triazole-4-yl) pyrazolo [1,5-a] pyridine-3-carboxamide (TJ064983)

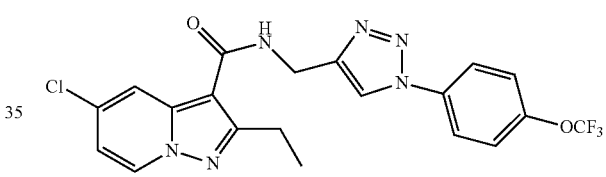

The synthesis process was as described in step 9 of Example 1 with a yield of 64.0%.

$^1$H NMR (400 MHz, DMSO-d$_6$): δ8.73 (m, 2H), 8.30 (s, 1H), 8.06 (d, J=9.2 Hz, 2H), 7.99 (s, 1H), 7.61 (d, J=8.4 Hz, 2H), 7.03 (dd, J=7.6, 2.0 Hz, 1H), 4.62 (d, J=5.2 Hz, 2H), 3.02 (q, J=7.6 Hz, 2H), 1.26 (t, J=7.4 Hz, 3H).

MS(ESI), m/z: 465 (M$^+$+H$^+$).

Example 16: 5-chloro-2-ethyl-N-methyl-N-(4-(4-(4-(trifluoromethoxy) phenyl) piperidine-1-yl) phenyl) pyrazolo [1,5-a] pyridine-3-carboxamide (TJ064985)

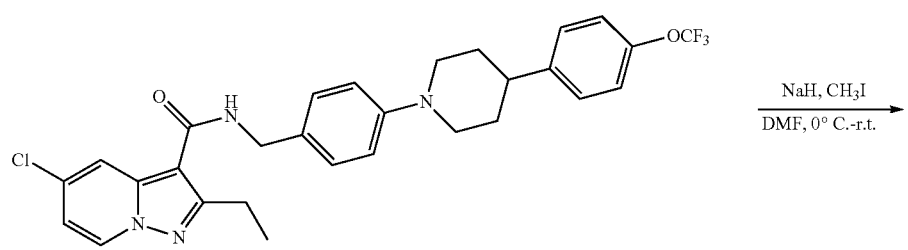

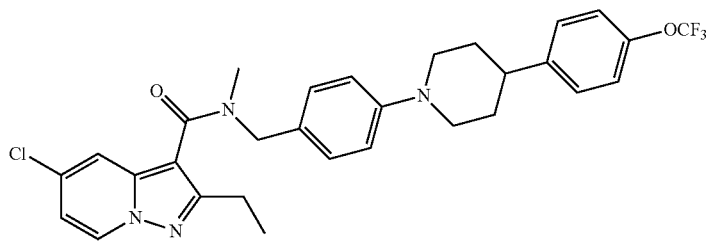

TJ170298 (0.2 g, 0.34 mmol) was dissolved in anhydrous DMF (7 mL), and 60% of NaH (0.02 g, 0.51 mmol) was added under ice bath, and after stirring for 0.5 h, CH$_3$I (0.063 g, 0.44 mmol) was added. The reaction was allowed to move to room temperature and stirring was continued for 1 h. Then water was slowing added to quench the reaction. After extraction with ethyl acetate three times, the organic phase was collected and the solution was rotary dried under reduced pressure to remove the solvent. 0.18 g (92.2%) of a product TJ064985 was isolated by column chromatography.

$^1$H NMR (400 MHz, DMSO-d$_6$): δ8.72 (d, J=7.2 Hz, 1H), 7.58 (s, 1H), 7.40 (d, J=8.8 Hz, 2H), 7.29 (d, J=8.4 Hz, 2H), 7.09 (m, 2H), 6.97 (m, 3H), 4.52 (s, 2H), 3.80 (m, 2H), 2.83 (s, 3H), 2.75 (m, 5H), 1.86 (m, 2H), 1.73 (m, 2H), 1.25 (t, J=7.6 Hz, 2H).

MS(ESI), m/z: 571 (M$^+$+H$^+$).

Example 17: 5-chloro-2-ethyl-N-(2-(4-(4-(4-(trifluoromethoxy) phenyl) piperidine-1-yl) phenyl) propane-2-substituted) pyrazolo [1,5-a] pyridine-3-carboxamide (TJ064987)

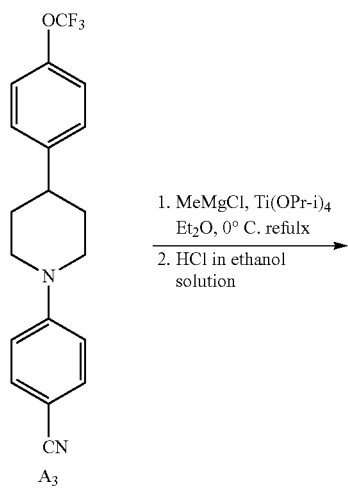

Step 1: 2-(4-(4-(4-(trifluoromethoxy) phenyl) piperidine-1-yl) phenyl) propan-2-amine hydrochloride

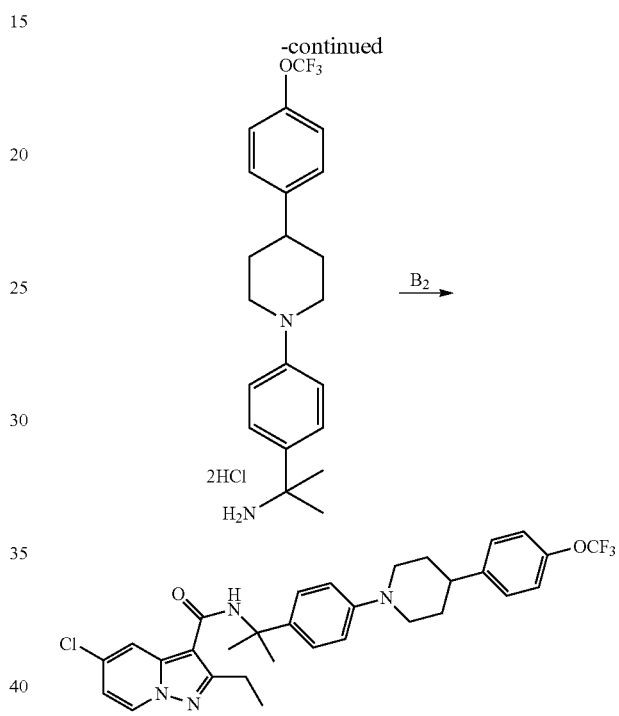

The intermediate A$_3$ (1.5 g, 4.33 mmol) was dissolved in dry ether (75 mL) pretreated by CaH$_2$. After replacing three times with Ar, MeMgCl (8.7 mL, 26 mmol, 3M in THF) was slowly added dropwisely under ice bath. After stirring for 0.5 h, Ti (OPr-i)$_4$ (1.23 g, 4.33 mmol) was added dropwisely at room temperature, after that the reaction system was heated to reflux overnight. After cooling, 10% NaOH (4.5 mmol, 18 mL) was added, and continued stirring at room temperature for 20 min and then filtered through a 2 cm silica gel column. The residue was washed three times with ethyl acetate and the solution was rotary dried under reduced pressure to remove the solvent. A product was isolated by column chromatography. The product was dissolved in ethanol and an excess of HCl in ethanol was added and the the solution was rotary dried to remove the solvent to give 2-(4-(4-(4-(trifluoromethoxy) phenyl) piperidine-1-yl) phenyl) propane-2-amine hydrochloride (0.87 g, 44.6%).

MS(ESI), m/z: 379 (M$^+$).

Step 2: 5-chloro-2-ethyl-N-(2-(4-(4-(4-(trifluoromethoxy) phenyl) piperidine-1-yl) phenyl) propane-2-substituted) pyrazolo [1,5-a] pyridine-3-carboxamide (TJ064987)

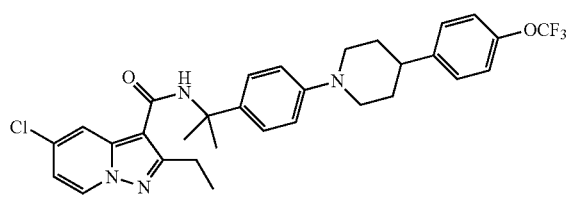 [SMILES: CCc1nn2ccc(Cl)cc2c1C(=O)NC(C)(C)c1ccc(N2CCC(c3ccc(OC(F)(F)F)cc3)CC2)cc1]

The synthesis process was as described in step 9 of Example 1 with a yield of 59.8%.

$^1$H NMR (400 MHz, DMSO-d$_6$): δ8.72 (d, J=7.2 Hz, 1H), 7.81 (s, 1H), 7.78 (d, J=2.0 Hz, 1H), 7.42 (d, J=8.8 Hz, 2H), 7.28 (m, 4H), 7.00 (dd, J=7.4, 2.2 Hz, 1H), 6.92 (d, J=8.8 Hz, 2H), 3.77 (m, 2H), 2.96 (q, J=7.6 Hz, 2H), 2.73 (m, 2H), 1.88 (m, 2H), 1 (m, 2H), 1.66 (s, 6H), 1 (t, J=7.6 Hz, 3H).

MS(ESI), m/z: 585 (M$^+$+H$^+$).

Example 18: 5-trifluoromethyl-2-methyl-N-(4-(4-(4-(trifluoromethoxy) phenyl) piperidine-1-yl) benzyl) pyrazolo [1,5-a] pyridine-3-carboxamide (TJ064995)

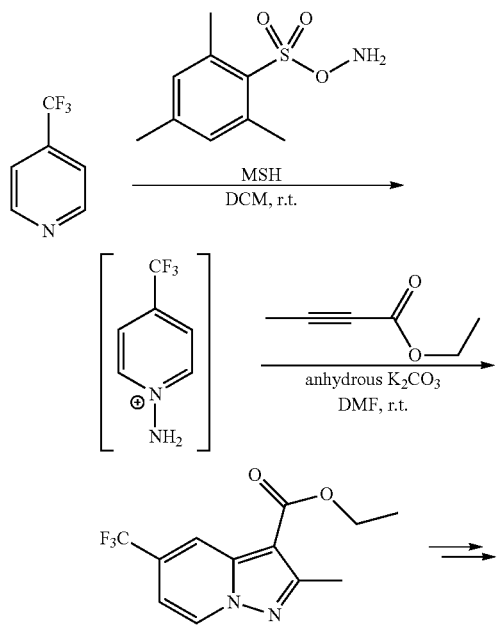

Step 1: 5-trifluoromethyl 2-methyl-pyrazolo [1,5-a] pyridine-3-ethyl carbonate

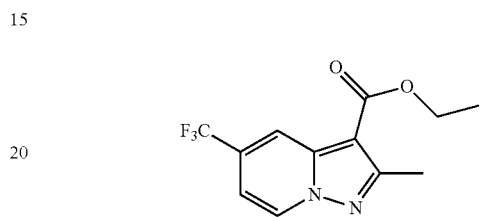

2-[(aminooxy) sulfonyl]-1,3,5-trimethylbenzene (1.63 g, 7.56 mmol) was dissolved in anhydrous DCM (25 mL), and added dropwisely under ice bath to a solution of 4-trifluoromethylpyridine (1.11 g, 7.56 mmol) in anhydrous DCM (25 mL). After stirring at room temperature for 2 h, the solution was rotary dried under reduced pressure to remove the solvent. 20 mL of anhydrous DMF (20 mL) was added and ethyl 2-butynoate (0.84 g, 7.56 mmol) and anhydrous K$_2$CO$_3$ (2.1 g, 15.12 mmol) were added. After stirring overnight at room temperature, the reaction was completed as detected by TLC. A large amount of water was added and extracted three times with ethyl acetate. The organic phase was collected and washed three times with brine and isolated by column chromatography to give 5-trifluoromethyl-2-methyl-pyrazolo [1,5-a] pyridine-3-ethyl carbonate as 0.94 g (45.44%) of a solid.

MS(ESI), m/z: 273 (M$^+$+H$^+$).

Step 2: 5-trifluoromethyl-2-methyl-N-(4-(4-(4-(trifluoromethoxy) phenyl) piperidine-1-yl) benzyl) pyrazolo [1,5-a] pyridine-3-carboxamide (TJ064995)

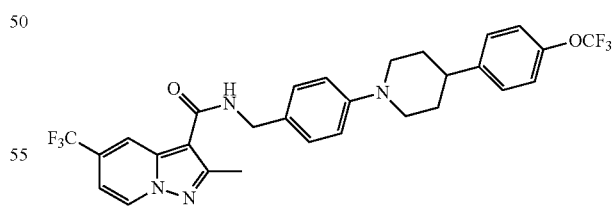

The synthesis process was as described in steps 8 and 9 in Example 1 with a total yield of 85.1% in two steps.

$^1$H NMR (400 MHz, DMSO-d$_6$): δ8.89 (d, J=6.8 Hz, 1H), 8.29 (t, J=5.8 Hz, 1H), 8.24 (s, 1H), 7.40 (d, J=8.4 Hz, 2H), 7.28 (d, J=8.4 Hz, 2H), 7.23 (m, 3H), 6.96 (d, J=8.4 Hz, 2H), 4.42 (d, J=5.6 Hz, 2H), 3.78 (m, 2H), 2.73 (m, 3H), 2.61 (s, 3H), 1.86 (m, 2H), 1.74 (m, 2H).

MS(ESI), m/z: 577 (M$^+$+H$^+$).

Example 19: 2,5-dimethyl-N-((1-(4-(trifluoromethoxy) phenyl)-1H-1,2,3-triazole-4-yl) pyrazolo [1,5-a] pyridine-3-carboxamide (TJ830003)

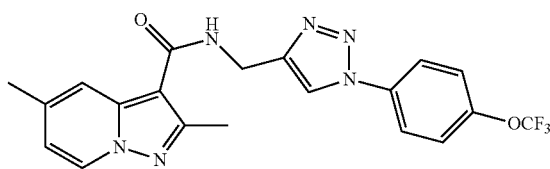 [SMILES: Cc1ccn2nc(C)c(C(=O)NCc3cn(-c4ccc(OC(F)(F)F)cc4)nn3)c2c1]

The synthesis process was as described in Example 15.
¹H NMR (400 MHz, DMSO-d₆): δ8.71 (s, 1H), 8.53 (d, J=6.8 Hz, 1H), 8.06 (d, J=9.2 Hz, 2H), 8.01 (t, J=5.6 Hz, 1H), 7.76 (s, 1H), 7.60 (d, J=8.4 Hz, 2H), 6.81 (d, J=6.8 Hz, 1H), 4.23 (d, J=5.6 Hz, 2H), 2.56 (s, 3H), 2.38 (s, 3H).
MS(ESI), m/z: 431 (M⁺+H⁺).

Example 20: 5-bromo-2-methyl-N-(4-(4-(4-(trifluoromethoxy) phenyl) piperidine-1-yl) benzyl) pyrazolo [1,5-a] pyridine-3-carboxamide (TJ830008)

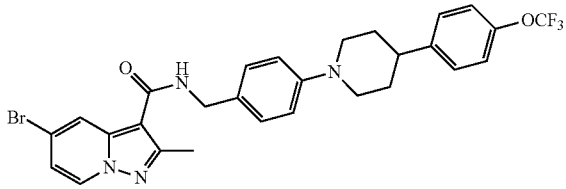

The synthesis process was as described in Example 1.
¹H NMR (400 MHz, DMSO-d₆): δ8.62 (d, J=7.2 Hz, 1H), 8.10 (s, 2H), 8.08 (t, J=6.2 Hz, 1H), 7.41 (d, J=8.8 Hz, 2H), 7.28 (d, J=8.4 Hz, 2H), 7.22 (d, J=8.4 Hz, 2H), 7.11 (dd, J=7.2, 2.0 Hz, 1H), 6.95 (d, J=8.8 Hz, 2H), 4.40 (d, J=5.6 Hz, 2H), 3.79 (m, 2H), 2.73 (m, 3H), 2.56 (s, 3H), 1.86 (m, 2H), 1.75 (m, 2H).
MS(ESI), m/z: 587 (M⁺+H⁺).

Example 21: 5-phenyl-2-methyl-N-(4-(4-(4-(trifluoromethoxy) phenyl) piperidine-1-yl) benzyl) pyrazolo [1,5-a] pyridine-3-carboxamide (TJ830012)

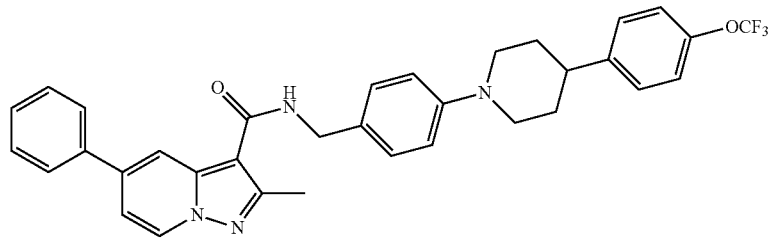 [SMILES: Cc1nn2ccc(-c3ccccc3)cc2c1C(=O)NCc1ccc(N2CCC(c3ccc(OC(F)(F)F)cc3)CC2)cc1]

The synthesis process was as described in Example 6.
¹H NMR (400 MHz, DMSO-d₆): δ8.72 (d, J=7.2 Hz, 1H), 8.13 (m, 2H), 7.80 (d, J=7.6 Hz, 2H), 7.53 (t, J=7.6 Hz, 2H), 7.45 (m, 1H), 7.40 (d, J=8.4 Hz, 2H), 7.28 (m, 5H), 6.96 (d, J=8.4 Hz, 2H), 4.43 (d, J=6.0 Hz, 2H), 3.78 (m, 2H), 2.73 (m, 3H), 2.58 (s, 3H), 1.86 (m, 2H), 1.74 (m, 2H).
MS(ESI), m/z: 585 (M⁺+H⁺).

Example 22: 5-chloro-2-ethyl-N-((6-(4-(trifluoromethoxy) phenyl) pyridine-3-yl) methyl) pyrazolo [1,5-a] pyridine-3-carboxamide (TJ830028)

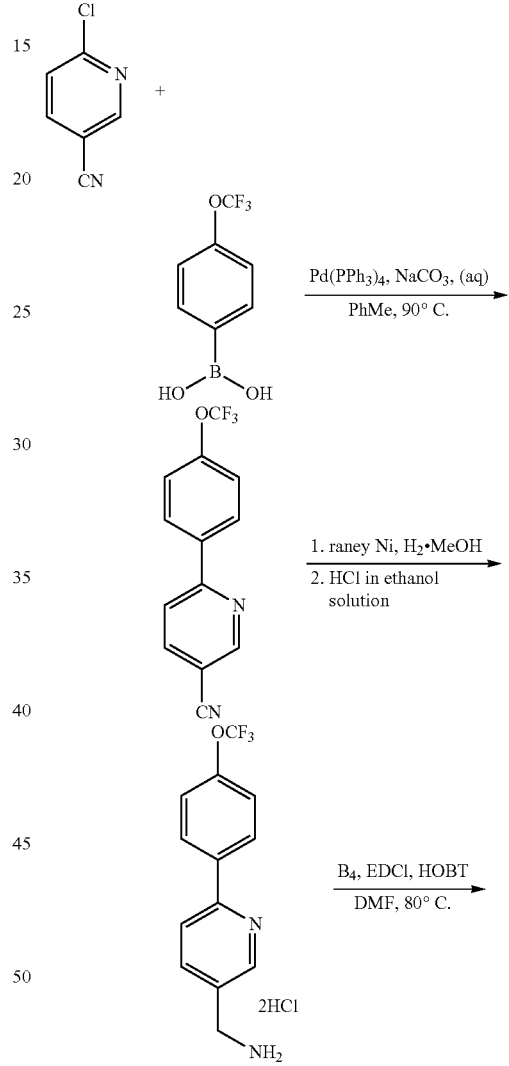

-continued

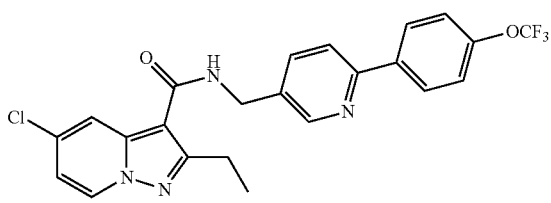 [SMILES: CCc1nn2ccc(Cl)cc2c1C(=O)NCc1ccc(-c2ccc(OC(F)(F)F)cc2)nc1]

Step 1: 6-(4-(trifluoromethoxy) phenyl)-3-cyanopyridine

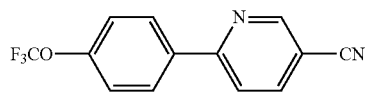

2-chloro-5-cyanopyridine (5.0 g, 36.1 mmol) and 4-trifluoromethoxybenzeneboronic acid (11.12 g, 54.0 mmol) were dissolved in toluene (100 mL), and palladium-tetrakis (triphenylphosphine) (0.5 g, 0.43 mmol) and $NaCO_3$ (2M, 36 mL) were added. After replacement with argon three times, the temperature was raised to 110° C., and after the reaction was carried out overnight, cooled to room temperature. Filtered through a 2 cm silica gel column, the residue was washed with ethyl acetate three times, and the solution was rotary dried under reduced pressure to remove the solvent. 7.62 g (79.9%) of a product 6-(4-(trifluoromethoxy) phenyl)-3-cyanopyridine was isolated by column chromatography.

MS(ESI), m/z: 265 ($M^++H^+$).

Step 2: (6-(4-(trifluoromethoxy) phenyl) pyridine-3 substituted) methylamine hydrochloride

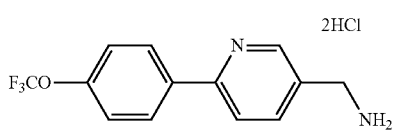

6-(4-(trifluoromethoxy) phenyl)-3-cyanopyridine (2.0 g, 7.57 mmol) was dissolved in methanol (100 mL), and a catalytic amount of raney nickel was added. A replacement with hydrogen balloon was repeated three times and stirred at room temperature for 3.5 h. After completion of the reaction, filtered through a 2 cm silica gel column, the residue was washed three times with ethyl acetate. The solution was rotary dried under reduced pressure to remove the solvent and a product was isolated by column chromatography. The product was dissolved in ethanol and an excess of HCl in ethanol solution was added to give salt, and the solution was rotary dried under reduced pressure to remove the solvent to give (6-(4-(trifluoromethoxy) phenyl) pyridine-3 substituted) methylamine hydrochloride as 1.5 g (58.1%) of a solid.

MS(ESI), m/z: 269 ($M^+$).

Step 3: 5-chloro-2-ethyl-N-((6-(4-(trifluoromethoxy) phenyl) pyridine-3-yl) methyl) pyrazolo [1,5-a] pyridine-3-carboxamide (TJ830028)

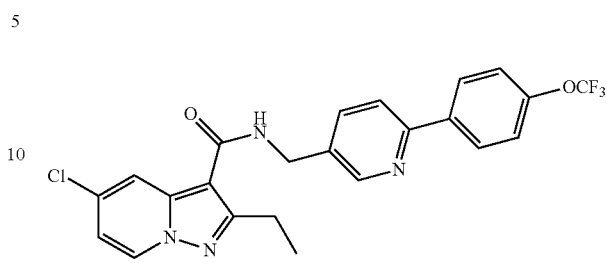

The synthesis process was as described in step 9 of Example 1 with a yield of 57.9%.

$^1$H NMR (400 MHz, DMSO-$d_6$): δ8.74 (d J=7.6 Hz, 1H), 8.68 (s, 1H), 8.32 (t, J=5.8 Hz, 1H), 8.20 (d, J=8.8 Hz, 2H), 7.98 (m, 2H), 7.88 (dd, J=8.2, 1.8 Hz, 1H), 7.47 (d, J=8.4 Hz, 2H), 7.04 (dd, J=7.2, 2.0 Hz, 1H), 4.55 (d, J=6.0 Hz, 2H), 3.02 (q, J=7.6 Hz, 2H), 1.25 (t, J=7.6 Hz, 3H).

MS(ESI), m/z: 475 ($M^++H+$).

Example 23: 2,5-dimethyl-N-((6-(4-(trifluoromethoxy) phenyl) pyridine-3-yl) methyl) pyrazolo [1,5-a] pyridine-3-carboxamide (TJ830025)

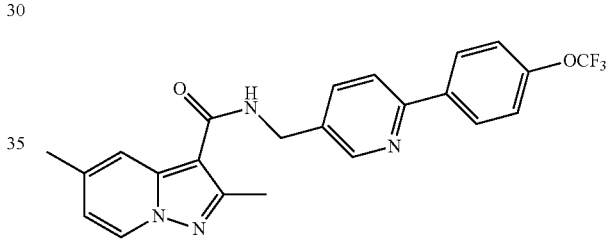

The synthesis process was as described in Example 22.

$^1$H NMR (400 MHz, DMSO-$d_6$): δ8.68 (s, 1H), 8.53 (d, J=6.8 Hz, 1H), 8.20 (d, J=8.8 Hz, 2H), 8.08 (t, J=5.8 Hz, 1H), 7.98 (d, J=8.4 Hz, 2H), 7.88 (dd, J=8.2, 2.2 Hz, 1H), 7.74 (s, 1H), 7.47 (d, J=8.0 Hz, 2H), 6.82 (dd, J=7.2, 1.6 Hz, 1H), 4.55 (d, J=5.6 Hz, 2H), 2.56 (s, 3H), 2.39 (s, 3H).

MS(ESI), m/z: 441 ($M^++H^+$).

Example 24: 5-methoxy-2-methyl-N-(4-(4-(4-(trifluoromethoxy) phenyl) piperidine-1-yl) benzyl) pyrazolo [1,5-a] pyridine-3-carboxamide (TJ830047)

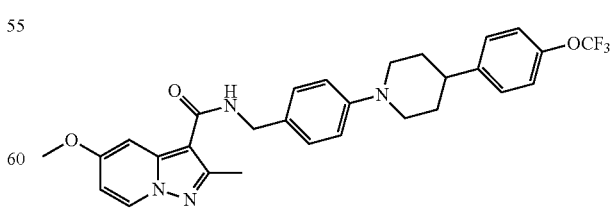

The synthesis process was as described in Example 6.

$^1$H NMR (400 MHz, DMSO-d6): δ8.49 (d, J=7.2 Hz, 1H), 7.82 (t, J=6.0 Hz, 1H), 7.41 (d, J=8.4 Hz, 1H), 7.29 (d, J=8.0 Hz, 2H), 7.24 (m, 3H), 6.95 (d, J=8.8 Hz, 2H), 6.64 (dd,

J=7.2, 2.4 Hz, 1H), 4.40 (d, J=6.0 Hz, 2H), 3.85 (s, 3H), 3.78 (m, 2H), 2.73 (m, 3H), 2.52 (s, 3H), 1.86 (m, 2H), 1.75 (m, 2H).

MS(ESI), m/z: 539 (M$^+$+H$^+$).

Example 25: 2-methyl-N-(4-(trifluoromethoxy) benzyl) pyrazolo [1,5-a] pyridine-3-carboxamide (TJ830069)

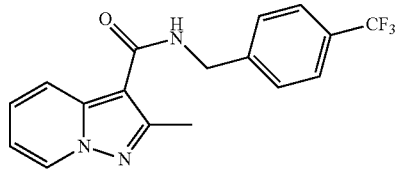 [SMILES: Cc1nn2ccccc2c1C(=O)NCc1ccc(C(F)(F)F)cc1]

The synthesis process was as described in Example 6.

$^1$H NMR (400 MHz, DMSO-d$_6$): δ8.66 (d, J=6.8 Hz, 1H), 8.18 (t, J=5.8 Hz, 1H), 7.94 (d, J=8.8 Hz, 1H), 7.70 (d, J=8.4 Hz, 2H), 7.58 (d, J=8.0 Hz, 2H), 7.40 (m, 1H), 6.97 (m, 1H), 4.57 (d, J=5.6 Hz, 2H), 2.58 (s, 3H).

MS(ESI), m/z: 334 (M$^+$+H$^+$).

Example 26: 5-chloro-2-ethyl-N-(1-(4-(4-(4-(trifluoromethoxy) phenyl) piperidine-1-yl) phenyl) ethanol) pyrazolo [1,5-a] pyridine-3-carboxamide (TJ830070)

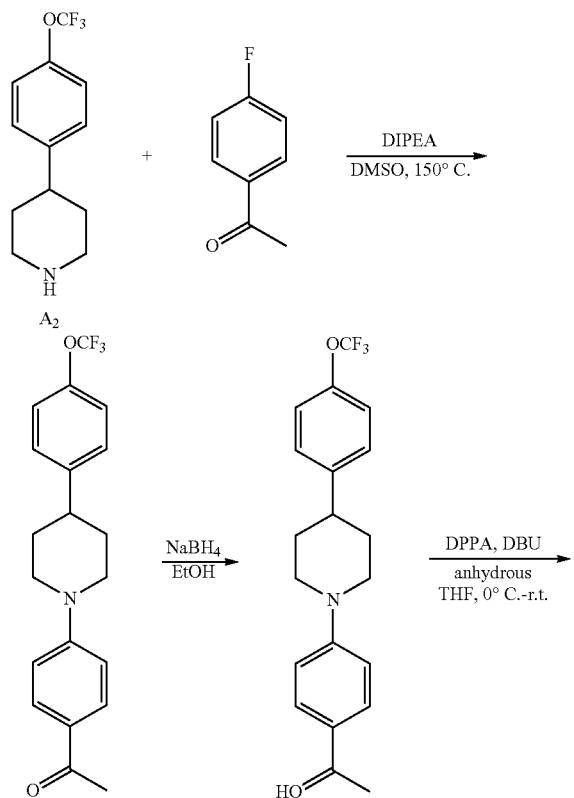

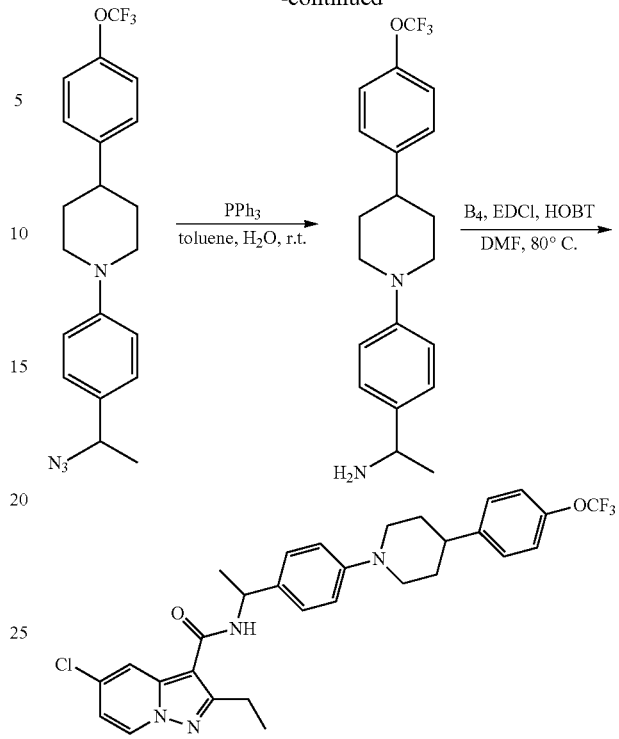

Step 1: 1-(4-(4-(4-(trifluoromethoxy) phenyl) piperidine-1-yl) phenyl) ethanone

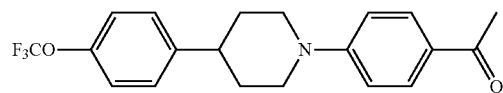

A$_2$ (1 g, 4.08 mmol) and 4-fluoroacetophenone (1.69 g, 12.23 mmol) were dissolved in DMSO (25 mL) at room temperature and DIPEA (1.56 g, 12.23 mmol) was added. The reaction system was heated to 150° C. overnight. The reaction was cooled to room temperature, and a large amount of water was added. After extraction with ethyl acetate three times, the organic phase was collected. 0.40 g (27%) of a product was obtained by column chromatography.

MS(ESI), m/z: 364 (M$^+$+H$^+$).

Step 2: 1-(4-(4-(4-(trifluoromethoxy) phenyl) piperidine-1-yl) phenyl) ethanol

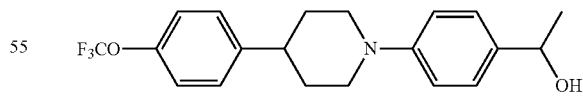

1-(4-(4-(4-(trifluoromethoxy) phenyl) piperidine-1-yl) phenyl) ethanone (0.4 g, 1.1 mmol) was dissolved in anhydrous ethanol (10 mL), and NaBH$_4$ (46 g, 1.21 mmol) was added slowly in portions. After stirring overnight at room temperature, ice water was added slowly to the reaction system. After stirring for 10 min, and after extraction with the ethyl acetate three times and the organic phase was collected. The solvent was rotary distilled under reduced pressure to give 0.40 g (99.2%) of a product.

MS(ESI), m/z: 366 (M$^+$+H$^+$).

Step 3: 1-(4-(1-azidoethyl) phenyl-4-(4-(trifluoromethoxy) phenyl) piperidine

1-(4-(4-(4-(trifluoromethoxy) phenyl) piperidine-1-yl) phenyl) ethanol (0.4 g, 1.1 mmol) was dissolved in anhydrous THF (10 mL), and was replaced with Argon three times. DPPA (0.6 g, 2.19 mmol) was added at 0° C., and after stirring for 5 min, DBU (0.33 g, 2.19 mmol) was added dropwisely slowly. After warming to room temperature overnight, a large amount of water was added. After extraction with the ethyl acetate three times, the organic phase was collected. 0.32 g (75.0%) of a product was obtained by column chromatography.
MS(ESI), m/z: 391 (M$^+$+H$^+$).

Step 4: 1-(4-(4-(4-(trifluoromethoxy) phenyl) piperidine-1-yl) phenyl) ethanamine

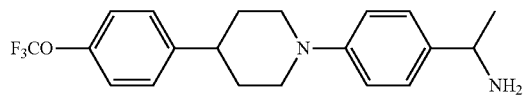

1-(4-(1-azidoethyl) phenyl-4-(4-(trifluoromethoxy) phenyl) piperidine (0.32 g, 0.82 mmol) was dissolved in a mixture system of toluene (8 mL) and H$_2$O (0.43 g, 1.64 mmol), and triphenylphosphine and (0.43 g, 1.64 mmol) was added. After 6 h of a reaction at room temperature, then ethyl acetate was added. After adding 1N aqueous hydrochloric acid to the organic phase, the aqueous phase was collected. pH was adjusted to 10 with aqueous NaOH. After extracted with DCM three times, the organic phase was collected. 0.22 g (72.9%) of a product was obtained by column chromatography
MS(ESI), m/z: 365 (M$^+$+H$^+$).

Step 5: 5-chloro-2-ethyl-N-(1-(4-(4-(4-(trifluoromethoxy) phenyl) piperidine-1-yl) phenyl) ethanol) pyrazolo [1,5-a] pyridine-3-carboxamide (TJ830070)

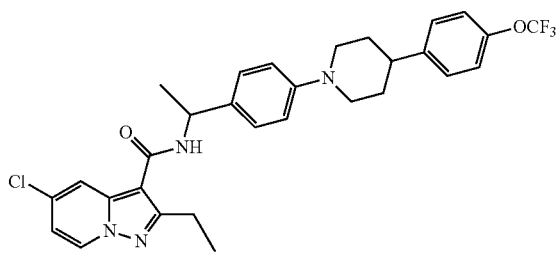 [SMILES: CCc1nn2ccc(Cl)cc2c1C(=O)NC(C)c1ccc(N2CCC(c3ccc(OC(F)(F)F)cc3)CC2)cc1]

The synthesis process was as described in step 9 of Example 1 with a yield of 51.1%.
$^1$H NMR (400 MHz, DMSO-d6): δ8.72 (d, J=7.2 Hz, 1H), 8.09 (d, J=8.0 Hz, 1H), 7.76 (d, J=2.0 Hz, 1H), 7.60 (d, J=8.4 Hz, 0.5H), 7.41 (m, 1.5H), 7.34 (d, J=8.0 Hz, 0.5H), 7.28 (m, 3.5H), 6.99 (m, 3H), 5.10 (m, 1H), 3.84 (m, 2H), 3.45 (m, 0.5H), 2.97 (q, J=7.6 Hz, 2H), 2.73 (m, 2H), 2.70 (m, 0.5H), 1.87 (m, 1.5H), 1.76 (m, 1.5H), 1.46 (d, J=7.2 Hz, 3H), 1.22 (d, J=7.6 Hz, 3H).
MS(ESI), m/z: 571 (M$^+$+H$^+$).

Example 27: 2,5-dimethyl-N-(4-(trifluoromethoxy) benzyl) pyrazolo [1,5-a] pyridine-3-carboxamide (TJ830072)

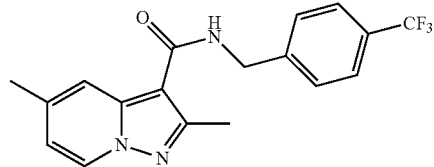 [SMILES: Cc1ccn2nc(C)c(C(=O)NCc3ccc(C(F)(F)F)cc3)c2c1]

The synthesis process was as described in Example 6.
$^1$H NMR (400 MHz, DMSO-d$_6$): δ8.54 (d, J=6.8 Hz, 1H), 8.07 (t, J=5.8 Hz, 1H), 7.74 (s, 1H), 7.70 (d, J=8.4 Hz, 2H), 7.57 (d, J=8.0 Hz, 2H), 4.57 (d, J=6.0 Hz, 2H), 2.56 (s, 3H), 2.38 (s, 3H).
MS(ESI), m/z: 348 (M$^+$+H$^+$).

Example 28: 5-isopropyl-2-methyl-N-(4-(4-(4-(trifluoromethoxy) phenyl) piperidine-1-yl) benzyl) pyrazolo [1,5-a] pyridine-3-carboxamide (TJ830073)

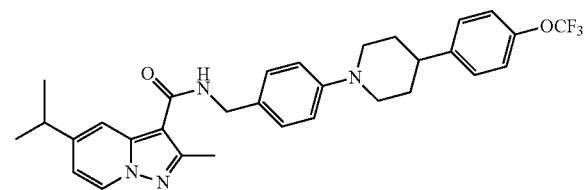 [SMILES: Cc1nn2ccc(C(C)C)cc2c1C(=O)NCc1ccc(N2CCC(c3ccc(OC(F)(F)F)cc3)CC2)cc1]

The synthesis process was as described in Example 6.
$^1$H NMR (400 MHz, DMSO-d$_6$): δ8.54 (d, J=7.2 Hz, 1H), 7.93 (t, J=6.0 Hz, 1H), 7.71 (s, 1H), 7.41 (d, J=8.8 Hz, 2H), 7.28 (d, J=8.4 Hz, 2H), 7.23 (d, J=8.4 Hz, 2H), 6.93 (d, J=8.4 Hz, 2H), 6.90 (d, J=7.2 Hz, 1H), 4.40 (d, J=6.0 Hz, 2H), 3.78 (m, 2H), 2.96 (m, 1H), 2.73 (m, 3H), 2.54 (s, 3H), 1.86 (m, 2H), 1.75 (m, 2H), 1.25 (s, 3H), 1.23 (s, 3H).
MS(ESI), m/z: 551 (M$^+$+H$^+$).

Example 29: 5-tert-Butyl-2-methyl-N-(4-(4-(4-(trifluoromethoxy) phenyl) piperidine-1-substituted) benzyl) pyrazolo [1,5-a] pyridine-3-carboxamide (TJ830075)

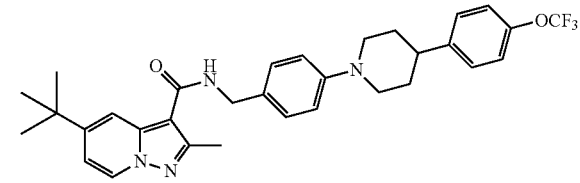 [SMILES: Cc1nn2ccc(C(C)(C)C)cc2c1C(=O)NCc1ccc(N2CCC(c3ccc(OC(F)(F)F)cc3)CC2)cc1]

The synthesis process was as described in Example 6.
¹H NMR (400 MHz, DMSO-d₆): δ8.53 (d, J=7.2 Hz, 1H), 7.99 (t, J=5.6 Hz, 1H), 7.76 (s, 1H), 7.41 (d, J=8.4 Hz, 2H), 7.28 (d, J=8.0 Hz, 2H), 7.23 (d, J=8.4 Hz, 2H), 7.04 (d, J=6.0 Hz, 1H), 6.95 (d, J=8.4 Hz, 2H), 4.40 (d, J=5.6 Hz, 2H), 3.78 (m, 2H), 2.73 (m, 3H), 2.54 (s, 3H), 1.86 (m, 2H), 1.75 (m, 2H), 1.31 (s, 9H).
MS(ESI), m/z: 565 (M⁺+H⁺).

Example 30: 5-ethyl-2-methyl-N-(4-(4-(4-(trifluoromethoxy) phenyl) piperidine-1-substituted) benzyl) pyrazolo [1,5-a] pyridine-3-carboxamide (TJ830082)

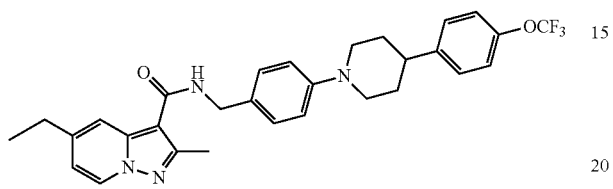

The synthesis process was as described in Example 6.
¹H NMR (400 MHz, DMSO-d₆): δ8.54 (d, J=7.2 Hz, 1H), 7.92 (t, J=5.8 Hz, 1H), 7.71 (s, 1H), 7.40 (d, J=8.8 Hz, 2H), 7.28 (d, J=8.4 Hz, 2H), 7.23 (d, J=8.8 Hz, 2H), 6.95 (d, J=8.4 Hz, 2H), 6.84 (dd, J=7.2, 1.6 Hz, 1H), 4.40 (d, J=5.6 Hz, 2H), 3.78 (m, 2H), 2.70 (m, 5H), 2.54 (s, 3H), 1.86 (m, 2H), 1.74 (m, 2H), 1. (t, J=7.6 Hz, 3H).
MS(ESI), m/z: 537 (M⁺+H⁺).

Example 31: 5-methyl-2-ethyl-N-(4-(4-(4-(trifluoromethoxy) phenyl) piperidine-1-substituted) benzyl) pyrazolo [1,5-a] pyridine-3-carboxamide (TJ830102)

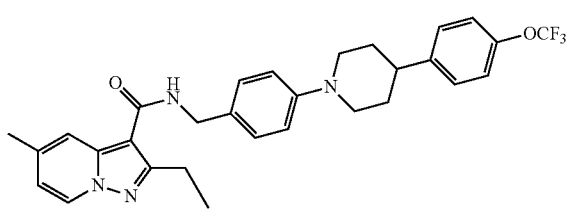 [SMILES: CCc1nn2ccc(C)cc2c1C(=O)NCc1ccc(N2CCC(c3ccc(OC(F)(F)F)cc3)CC2)cc1]

The synthesis process was as described in Example 6.
¹H NMR (400 MHz, DMSO-d₆): δ8.54 (d, J=7.2 Hz, 1H), 7.98 (t, J=5.8 Hz, 1H), 7.67 (s, 1H), 7.40 (d, J=8.4 Hz, 2H), 7.28 (d, J=8.4 Hz, 2H), 7.22 (d, J=8.8 Hz, 2H), 6.95 (d, J=8.8 Hz, 2H), 6.79 (dd, J=7.2, 2.0 Hz, 1H), 4.39 (d, J=5.6 Hz, 2H), 3.78 (m, 2H), 2.98 (q, J=7.6 Hz, 2H), 2.72 (m, 3H), 2.37 (s, 3H), 1.86 (m, 2H), 1.74 (m, 2H), 1.24 (t, J=7.6 Hz, 3H).
MS(ESI), m/z: 537 (M⁺+H⁺).

Example 32: 5-methyl-2-ethoxy-N-(4-(4-(4-(trifluoromethoxy) phenyl) piperidine-1-substituted) benzyl) pyrazolo [1,5-a] pyridine-3-carboxamide (TJ830108)

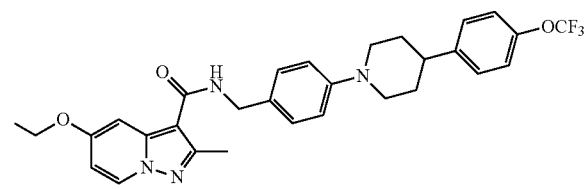 [SMILES: CCOc1ccn2nc(C)c(C(=O)NCc3ccc(N4CCC(c5ccc(OC(F)(F)F)cc5)CC4)cc3)c2c1]

The synthesis process was as described in Example 6.
¹H NMR (400 MHz, DMSO-d₆): δ8.48 (d, J=7.6 Hz, 1H), 7.80 (t, J=6.0 Hz, 1H), 7.40 (d, J=8.8 Hz, 2H), 7.28 (d, J=8.4 Hz, 2H), 7.23 (m, 3H), 6.95 (d, J=8.4 Hz, 2H), 6.61 (dd, J=7.6, 2.8 Hz, 1H), 4.39 (d, J=5.6 Hz, 2H), 4.10 (q, J=6.8 Hz, 2H), 3.78 (m, 2H), 2.72 (m, 3H), 2.51 (s, 3H), 1.86 (m, 2H), 1.74 (m, 2H), 1.37 (t, J=6.8 Hz, 3H).
MS(ESI), m/z: 553 (M⁺+H⁺).

Example 33: 5-chloro-2-ethyl-N-(4-(4-(4-(trifluoromethoxy) phenyl) piperidine-1-yl) phenethyl) pyrazolo [1,5-a] pyridine-3-carboxamide (TJ830128)

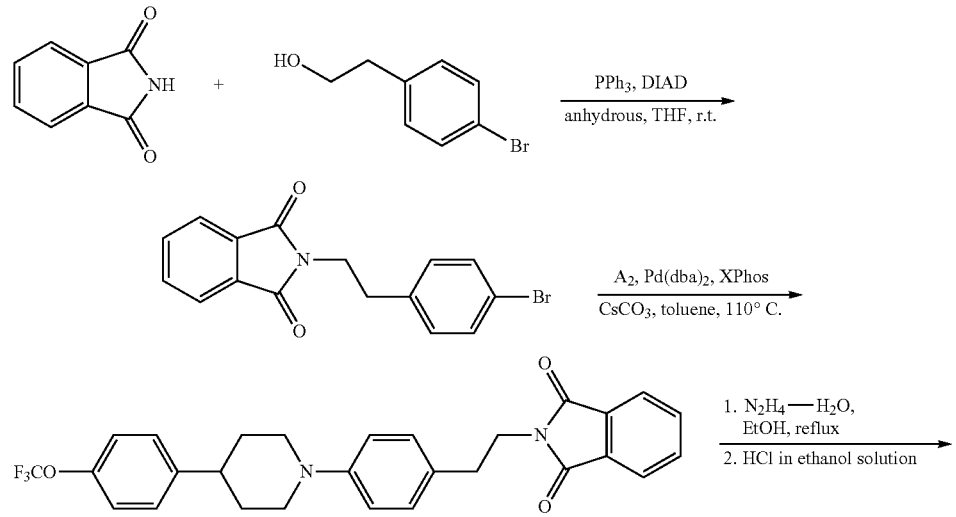

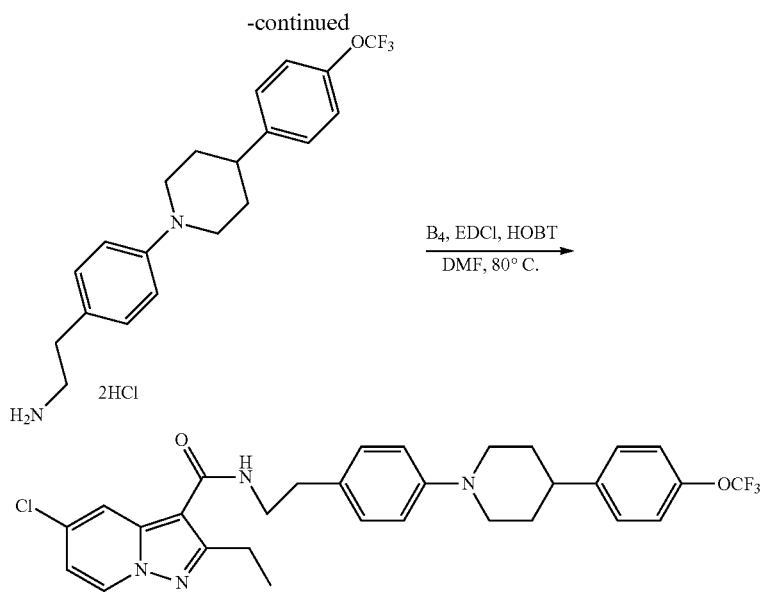

Step 1: 2-(4-bromophenethyl) isoindoline-1,3-dione

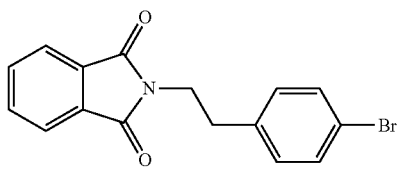 [SMILES: O=C1c2ccccc2C(=O)N1CCc1ccc(Br)cc1]

Isoindoline-1,3-dione (0.33 g, 2.27 mmol), 2-(4-bromophenyl) ethanol (0.46 g, 2.27 mmol) and triphenylphosphine (0.59 g, 2.27 mmol) were dissolved in anhydrous THF (7.5 mL), and DIAD (0.46 g, 2.27 mmol) was slowly added dropwisely. Stir at room temperature for 3 h, then rotary dried under reduced pressure, and 0.56 g (yield 75%) of a product was obtained by column chromatography.

MS(ESI), m/z: 330 (M$^+$+H$^+$).

Step 2: 2-(4-(4-(4-(trifluoromethoxy) phenyl) piperidine-1-yl) phenethyl) isoindoline-1,3-dione

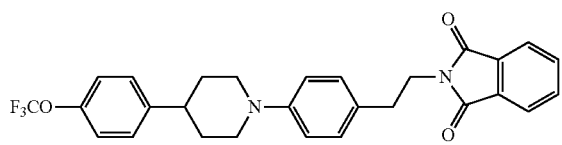 [SMILES: O=C1c2ccccc2C(=O)N1CCc1ccc(N2CCC(c3ccc(OC(F)(F)F)cc3)CC2)cc1]

2-(4-bromophenethyl) isoindoline-1,3-dione (0.56 g, 1.7 mmol) and A$_2$ (0.63 g, 2.55 mmol) were dissolved in toluene (15 mL), and then Pd(dba)$_2$ (59 mg, 0.1 mmol), XPhos (97 mg, 0.2 mmol) and cesium carbonate (2.21 g, 6.8 mmol) were added. The reaction system was replaced with argon three times and heated to 110° C. overnight.

The reaction was cooled to room temperature and filtered through a 2 cm silica gel column. The residue was washed three times with ethyl acetate and the solution was rotary dried under reduced pressure to remove the solvent. 0.19 g (26%) of a product was isolated by column chromatography.

MS(ESI), m/z: 495 (M$^+$+H$^+$).

Step 3: 2-(4-(4-(4-(trifluoromethoxy) phenyl) piperidine-1-yl) phenyl) ethylamine

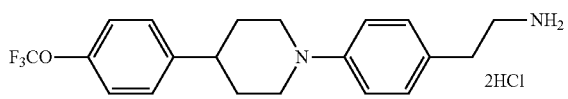 [SMILES: NCCc1ccc(N2CCC(c3ccc(OC(F)(F)F)cc3)CC2)cc1]

2-(4-(4-(4-(trifluoromethoxy) phenyl) piperidine-1-yl) phenethyl) isoindoline-1,3-dione (0.19 g, 0.38 mmol) was dissolved in ethanol (4 mL), and 80% hydrated hydrazine (0.072 mL) was added and heated to reflux (80° C.) for 1.5 h. After completion of the reaction, the solution was rotary dried under reduced pressure to remove the solvent, the solute left behind was dissolved with ethyl acetate and washed three times with brine. An excess of hydrochloric acid in ethanol solution was added to the organic phase and dried under reduced pressure to give 0.13 g (78.7%) of a product.

MS(ESI), m/z: 365 (M$^+$+H$^+$).

Step 4: 5-chloro-2-ethyl-N-(4-(4-(4-(trifluoromethoxy) phenyl) piperidine-1-yl) phenethyl) pyrazolo [1,5-a] pyridine-3-carboxamide (TJ830128)

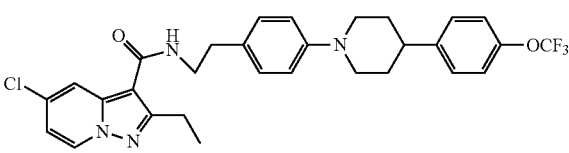 [SMILES: CCc1nn2ccc(Cl)cc2c1C(=O)NCCc1ccc(N2CCC(c3ccc(OC(F)(F)F)cc3)CC2)cc1]

The synthesis process was as described in step 9 of Example 1 with a yield of 63.8%.

¹H NMR (400 MHz, DMSO-d₆): δ8.70 (d, J=7.2 Hz, 1H), 7.75 (t, J=5.6 Hz, 1H), 7.70 (s, 1H), 7.41 (d, J=8.4 Hz, 2H), 7.29 (d, J=8.0 Hz, 2H), 7.12 (d, J=8.4 Hz, 2H), 6.61 (dd, J=7.2, 2.0 Hz, 1H), 6.94 (d, J=8.8 Hz, 2H), 3.76 (m, 2H), 3.46 (q, J=6.8 Hz, 2H), 2.93 (q, J=7.6 Hz, 2H), 2.74 (m, 5H), 1.87 (m, 2H), 1.75 (m, 2H), 1.21 (t, J=7.2 Hz, 3H).

MS(ESI), m/z: 571 (M⁺+H⁺).

Example 34: 2,5-dimethyl-N-((5-(4-(trifluoromethoxy) phenyl) thiophene-2-yl) methyl) pyrazolo [1,5-a] pyridine-3-carboxamide (TJ830132)

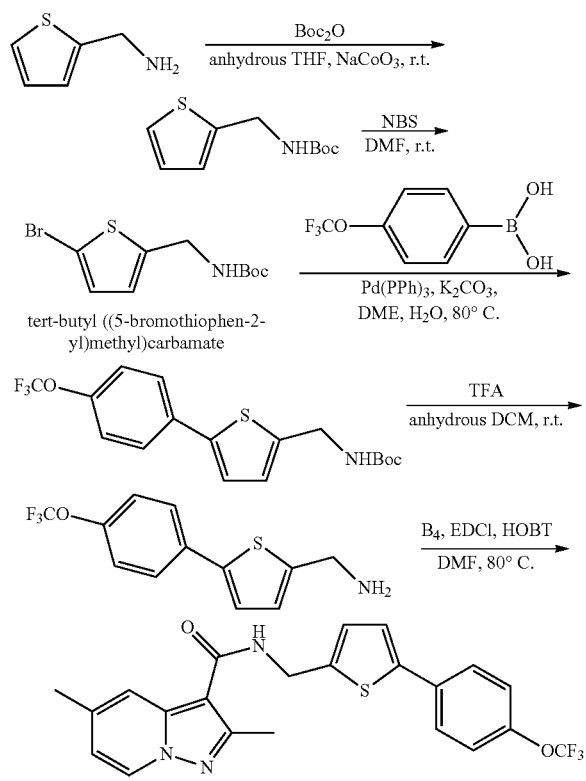

Step 1: tert-butyl (thiophen-2-yl methyl) carbamate

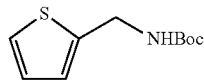 [SMILES: CC(C)(C)OC(=O)NCc1cccs1]

Thiophene-2-yl methylamine (1.4 g, 12.36 mmol) and sodium bicarbonate (1.04 g, 12.36 mmol) were dissolved in anhydrous THF (20 mL), and Boc₂O (2.76 g, 13.6 mmol) was slowly added dropwisely. After 3 h reaction at room temperature, the solution was rotary dried under reduced pressure to remove the solvent and ethyl acetate was added to extract. The organic phase was collected, and 2.61 g (99.1%) of a product was obtained by column chromatography.

MS(ESI), m/z: 214 (M⁺+H⁺).

Step 2: tert-butyl ((5-bromothiophen-2-yl) methyl) carbamate

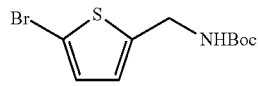

Tert-butyl (thiophen-2-yl methyl) carbamate (2.22 g, 10.41 mmol) was dissolved in DMF (11 mL), and then NBS (2.04 g, 11.45 mmol) was added. After 5 h reaction at room temperature, a large amount of water was added. After extraction with ethyl acetate, the organic phase was collected. 2.56 g (84.3%) of a product was obtained by column chromatography.

MS(ESI), m/z: 292 (M⁺+H⁺).

Step 3: tert-butyl ((5-(4-(trifluoromethoxy) phenyl) thiophene-2-yl) carbamate

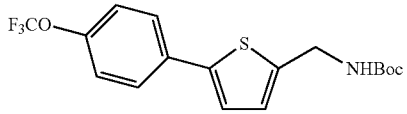 [SMILES: CC(C)(C)OC(=O)NCc1ccc(-c2ccc(OC(F)(F)F)cc2)s1]

Tert-butyl (5-bromothiophen-2-yl) methyl) carbamate (1.0 g, 3.42 mmol), 4-trifluoromethoxybenzeneboronic acid (0.84 g, 4.11 mmol), Pd (PPh₃)₄ (0.2 g, 0.17 mmol) and potassium carbonate (2.66 g, 12.5 mmol) were dissolved in H₂O (6.3 mL) and DME (8 mL), replaced with argon three times and reacted at 80° C. overnight. The reaction was cooled to room temperature and filtered through a 2 cm silica gel column. The residue was washed three times with ethyl acetate and the solution was rotary dried under reduced pressure to remove the solvent. 1.2 g (93.7%) of a product was isolated by column chromatography.

MS(ESI), m/z: 374 (M⁺+H⁺).

Step 4: (5-(4-(trifluoromethoxy) phenyl) thiophene-2-yl) methylamine

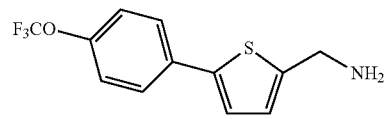 [SMILES: NCc1ccc(-c2ccc(OC(F)(F)F)cc2)s1]

Tert-butyl ((5-(4-(trifluoromethoxy) phenyl) thiophene-2-yl) carbamate (1.2 g, 3.2 mmol) was dissolved in anhydrous DCM (40 mL), and TFA (2.76 mL) was slowly added dropwisely. After the reaction was carried out for 3 h, the solution was rotary dried under reduced pressure to remove the solvent, dissolved in ethyl acetate, and then saturated solution of sodium hydrogencarbonate was added until pH of the aqueous phase was equal to 8.0. The organic phase was separated and the aqueous phase was extracted with ethyl acetate three times. The organic phase was combined and the solution was rotary dried under reduced pressure to remove the solvent to give 0.58 g (66.5%) of a product.

MS(ESI), m/z: 274 (M⁺+H⁺).

Step 5: 2,5-dimethyl-N-((5-(4-(trifluoromethoxy) phenyl) thiophene-2-yl) methyl) pyrazolo [1,5-a] pyridine-3-carboxamide (TJ830132)

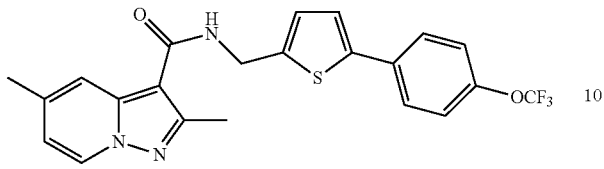

The synthesis process was as described in step 9 of Example 1 with a yield of 75.9%.

$^1$H NMR (400 MHz, DMSO-d$_6$): δ8.53 (d, J=6.8 Hz, 1H), 8.15 (t, J=6.0 Hz, 1H), 7.73 (m, 3H), 7.39 (m, 3H), 7.05 (d, J=3.6 Hz, 1H), 6.82 (d, J=7.2 Hz, 1H), 4.64 (d, J=5.6 Hz, 2H), 2.55 (s, 3H), 2.39 (s, 3H).

MS(ESI), m/z: 446 (M$^+$+H$^+$).

Example 35: 2,5-dimethyl-N-((5-(4-(trifluoromethoxy) phenyl) pyridine-2-yl) methyl) pyrazolo [1,5-a] pyridine-3-carboxamide (TJ830133)

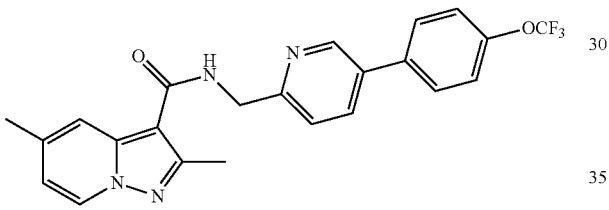

The synthesis process was as described in Example 22.

$^1$H NMR (400 MHz, DMSO-d$_6$): δ8.86 (s, 1H), 8.55 (d, J=7.2 Hz, 1H), 8.09 (m, 2H), 7.86 (d, J=8.8 Hz, 2H), 7.80 (s, 1H), 7.48 (m, 3H), 6.83 (dd, J=7.2, 1.6 Hz, 1H), 4.64 (d, J=6.0 Hz, 2H), 2.59 (s, 3H), 2.39 (s, 3H).

MS(ESI), m/z: 441 (M$^+$+H$^+$).

Example 36: 5-methyl-2-propyl-N-(4-(4-(4-(trifluoromethoxy) phenyl) piperidine-1-yl) benzyl) pyrazolo [1,5-a] pyridine-3-carboxamide (TJ830134)

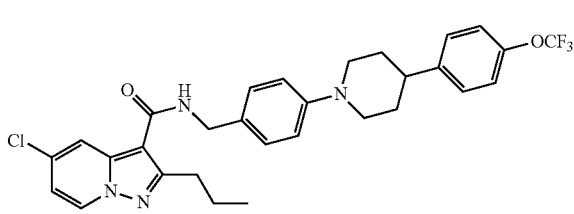 [SMILES: CCCc1nn2ccc(Cl)cc2c1C(=O)NCc1ccc(N2CCC(c3ccc(OC(F)(F)F)cc3)CC2)cc1]

The synthesis process was as described in Example 1.

$^1$H NMR (400 MHz, DMSO-d$_6$): δ8.72 (d, J=7.2 Hz, 1H), 8.20 (t, J=6.0 Hz, 1H), 7.88 (d, J=2.0 Hz, 1H), 7.40 (d, J=8.4 Hz, 2H), 7.28 (d, J=8.4 Hz, 2H), 7.21 (d, J=8.4 Hz, 2H), 7.01 (dd, J=7.6, 2.4 Hz, 1H), 6.95 (d, J=8.4 Hz, 2H), 4.39 (d, J=5.6 Hz, 2H), 3.78 (m, 2H), 2.95 (t, J=7.6 Hz, 2H), 2.73 (m, 3H), 1.86 (m, 2H), 1.72 (m, 5H), 0.90 (t, J=7.6 Hz, 3H).

MS(ESI), m/z: 571 (M$^+$+H$^+$).

Example 37: N-(4-(tert-butyl) benzyl)-2,5-dimethyl-pyrazolo [1,5-a] pyridine-3-carboxamide (TJ830135)

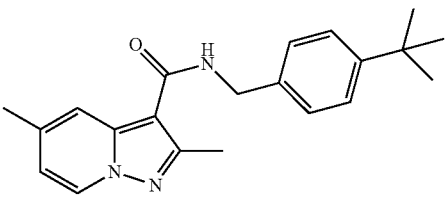 [SMILES: Cc1ccn2nc(C)c(C(=O)NCc3ccc(C(C)(C)C)cc3)c2c1]

The synthesis process was as described in Example 6.

$^1$H NMR (400 MHz, DMSO-d$_6$): δ8.52 (d, J=6.8 Hz, 1H), 7.96 (t, J=6.0 Hz, 1H), 7.72 (s, 1H), 7.35 (d, J=8.0 Hz, 2H), 7.28 (d, J=8.4 Hz, 2H), 6.80 (dd, J=6.8, 1.6 Hz, 1H), 4.45 (d, J=6.0 Hz, 2H), 2.54 (s, 3H), 2.38 (s, 3H), 1.27 (s, 9H).

MS(ESI), m/z: 336 (M$^+$+H$^+$).

Example 38: N-(4-(dimethylamino) benzyl)-2,5-dimethylpyrazolo [1,5-a] pyridine-3-carboxamide (TJ830136)

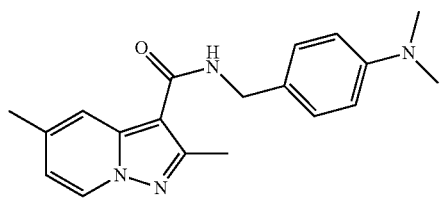

The synthesis process was as described in Example 6.

$^1$H NMR (400 MHz, DMSO-d$_6$): δ8.51 (d, J=7.2 Hz, 1H), 7.86 (t, J=5.6 Hz, 1H), 7.69 (s, 1H), 7.19 (d, J=8.4 Hz, 2H), 6.79 (d, J=6.0 Hz, 1H), 6.70 (d, J=8.4 Hz, 2H), 4.36 (d, J=6.0 Hz, 2H), 2.85 (s, 6H), 2.52 (s, 3H), 2.37 (s, 3H).

MS(ESI), m/z: 323 (M$^+$+H$^+$).

Example 39: N-(4-(4-(4-methoxyphenyl) piperidine-1-yl) benzyl)-2,5-dimethyl-pyrazolo [1,5-a] pyridine-3-carboxamide (TJ830140)

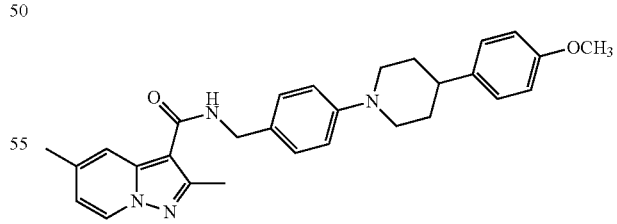

The synthesis process was as described in Example 6.

$^1$H NMR (400 MHz, DMSO-d$_6$): δ8.52 (d, J=6.8 Hz, 1H), 7.90 (t, J=6.0 Hz, 1H), 7.71 (s, 1H), 7.20 (m, 4H), 6.94 (d, J=8.4 Hz, 2H), 6.86 (d, J=8.8 Hz, 2H), 6.80 (dd, J=6.8, 1.2 Hz, 1H), 4.39 (d, J=5.6 Hz, 2H), 3.76 (m, 2H), 3.72 (s, 3H), 2.71 (m, 2H), 2.60 (m, 1H), 2.53 (s, 3H), 2.37 (s, 3H), 1.82 (m, 2H), 1.71 (m, 2H).

MS(ESI), m/z: 469 (M$^+$+H$^+$).

Example 40: N-(4-(4-(4-fluorophenyl) piperidine-1-yl) benzyl)-2,5-dimethyl-pyrazolo [1,5-a] pyridine-3-carboxamide (TJ830141)

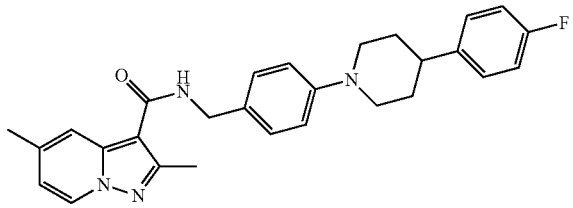 [SMILES: Cc1ccn2nc(C)c(C(=O)NCc3ccc(N4CCC(c5ccc(F)cc5)CC4)cc3)c2c1]

The synthesis process was as described in Example 6.

$^1$H NMR (400 MHz, DMSO-d$_6$): δ8.52 (d, J=7.2 Hz, 1H), 7.90 (t, J=6.0 Hz, 1H), 7.71 (s, 1H), 7.30 (m, 2H), 7.22 (d, J=8.4 Hz, 2H), 7.11 (m, 2H), 6.94 (d, J=8.8 Hz, 2H), 6.80 (d, J=7.2 Hz, 1H), 4.39 (d, J=5.6 Hz, 2H), 3.77 (m, 2H), 2.69 (m, 3H), 2.53 (s, 3H), 2.37 (s, 3H), 1.84 (m, 2H), 1.73 (m, 2H).

MS(ESI), m/z: 457 (M$^+$+H$^+$).

Example 41: 2,5-dimethyl-N-(4-(piperidine-1-yl) benzyl) pyrazolo [1,5-a] pyridine-3-carboxamide (TJ830146)

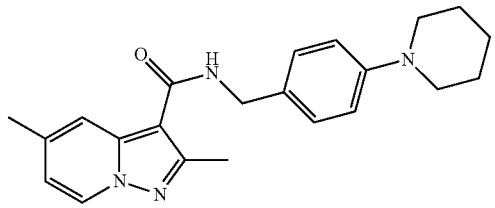 [SMILES: Cc1ccn2nc(C)c(C(=O)NCc3ccc(N4CCCCC4)cc3)c2c1]

The synthesis process was as described in Examples 1 and 6.

$^1$H NMR (400 MHz, DMSO-d$_6$): δ8.51 (d, J=7.6 Hz, 1H), 7.88 (t, J=5.6 Hz, 1H), 7.70 (s, 1H), 7.19 (d, J=8.4 Hz, 2H), 6.88 (d, J=8.8 Hz, 2H), 6.79 (dd, J=6.8, 1.6 Hz, 1H), 4.37 (d, J=6.0 Hz, 2H), 3.08 (m, 4H), 2.53 (s, 3H), 2.37 (s, 3H), 1.60 (m, 4H), 1.51 (m, 2H).

MS(ESI), m/z: 363 (M$^+$+H$^+$).

Example 42: N-(4-(4-fluorophenoxy) benzyl)-2,5-dimethylpyrazolo [1,5-a] pyridine-3-carboxamide (TJ830147)

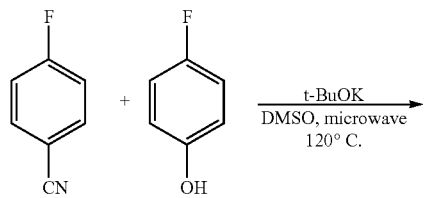

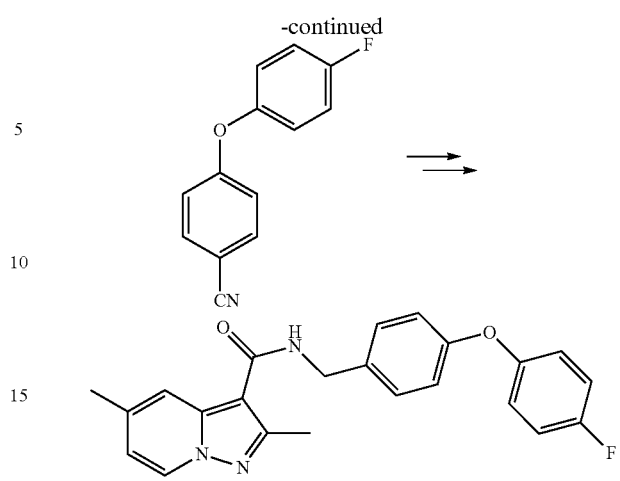

Step 1: 4-(4-fluorophenoxy) benzonitrile

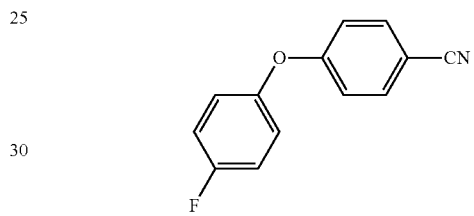

4-fluorobenzonitrile (0.6 g, 5 mmol), 4-fluorophenol (0.85 g, 7.5 mmol) and potassium tert-butoxide (1.1 g, 10 mmol) were dissolved in DMSO (10 mL) and heated in a microwave reactor to 120° C. After 15 min reaction, the mixture was cooled to room temperature, and a large amount of water was added. After extraction with ethyl acetate three times, the organic phase was collected. 0.42 g (39.3%) of product was obtained by column chromatography.

MS(ESI), m/z: 214 (M$^+$+H$^+$).

Step 2: N-(4-(4-fluorophenoxy) benzyl)-2,5-dimethylpyrazolo [1,5-a] pyridine-3-carboxamide (TJ830147)

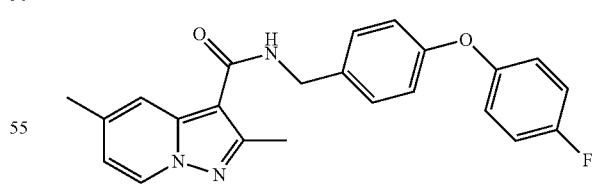

The synthesis process was as described in steps 4 and 9 of Example 1 with a yield of 80.6% in two steps.

$^1$H NMR (400 MHz, DMSO-d$_6$): δ8.52 (d, J=6.8 Hz, 1H), 7.99 (t, J=6.0 Hz, 1H), 7.72 (s, 1H), 7.37 (d, J=8.4 Hz, 2H), 7.20 (m, 2H), 7.03 (m, 2H), 6.97 (d, J=8.4 Hz, 2H), 6.80 (dd, J=7.2, 1.6 Hz, 1H), 4.46 (d, J=6.0 Hz, 2H), 2.54 (s, 3H), 2.38 (s, 3H).

MS(ESI), m/z: 390 (M$^+$+H$^+$).

Example 43: 2,5-dimethyl-N-(4-(4-(trifluoromethyl) piperidine-1-yl) benzyl) pyrazolo [1,5-a] pyridine-3-carboxamide (TJ830149)

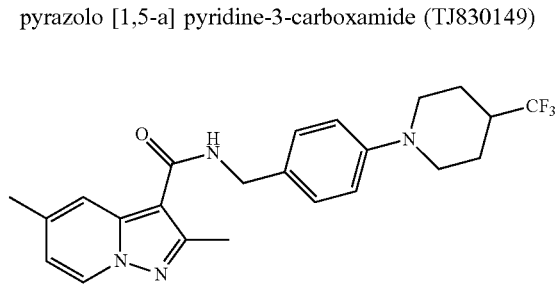

The synthesis process was as described in Examples 1 and 6.

¹H NMR (400 MHz, DMSO-d₆): δ8.52 (d, J=6.8 Hz, 1H), 7.90 (t, J=6.0 Hz, 1H), 7.70 (s, 1H), 7.21 (d, J=8.4 Hz, 2H), 6.92 (d, J=8.4 Hz, 2H), 6.79 (dd, J=6.8, 1.6 Hz, 1H), 4.38 (d, J=5.6 Hz, 2H), 3.74 (m, 2H), 2.68 (m, 2H), 2.53 (s, 3H), 2.44 (m, 1H), 2.37 (s, 3H), 1.86 (m, 2H), 1.54 (m, 2H).

MS(ESI), m/z: 431 (M⁺+H⁺).

Example 44: 2,5-Dimethyl-N-((2-(4-(trifluoromethoxy) phenyl) pyrimidine-5-yl) methyl) pyrazolo [1,5-a] pyridine-3-carboxamide (TJ830150)

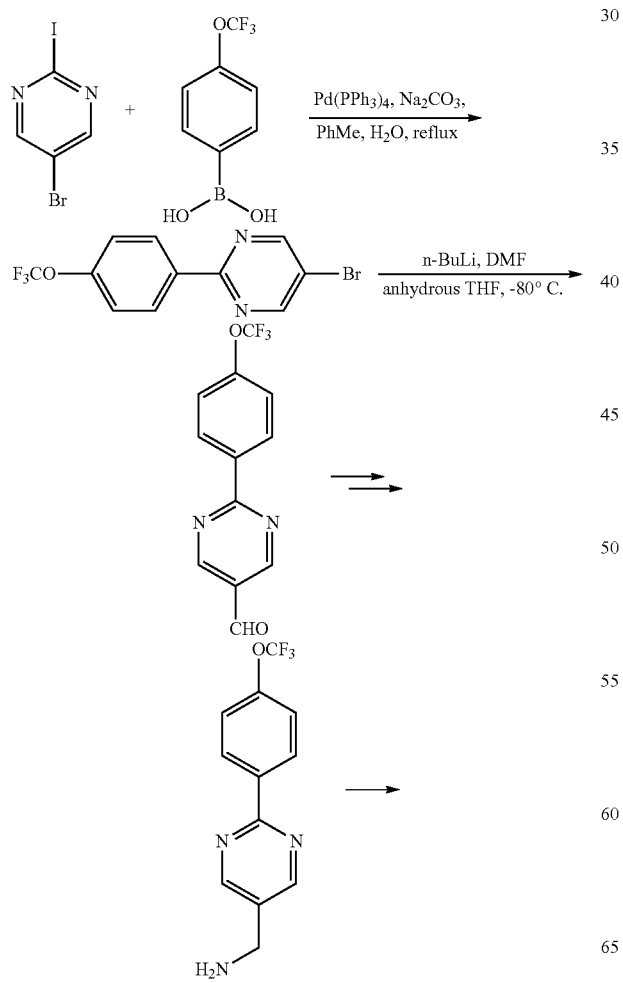

Step 1: 5-bromo-2-(4-(trifluoromethoxy) phenyl) pyrimidine

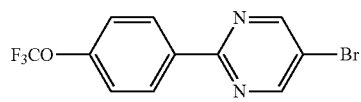

5-bromo-2-iodopyrimidine (6.0 g, 21.1 mmol), 4-trifluoromethoxybenzeneboronic acid (4.77 g, 23.2 mmol), Pd(PPh₃)₄ (0.24 g, 0.21 mmol) and sodium carbonate (4.46 g, 42.12 mmol) were dissolved in a mixed solvent of H₂O (60 mL) and toluene (480 mL) and heated to reflux overnight. The reaction was cooled to room temperature and filtered through a 2 cm silica gel column. The residue was washed three times with ethyl acetate and the solution was rotary dried under reduced pressure to remove the solvent. 5.6 g (83.6%) of a product was obtained by column chromatography.

MS(ESI), m/z: 319 (M⁺+H⁺).

Step 2: 2-(4-(Trifluoromethoxy) phenyl) pyrimidine-5-carbaldehyde

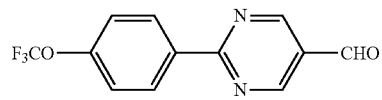 [SMILES: O=Cc1cnc(-c2ccc(OC(F)(F)F)cc2)nc1]

5-bromo-2-(4-(trifluoromethoxy) phenyl) pyrimidine (3.2 g, 9.72 mmol) was dissolved in anhydrous THF (100 mL), after replacement with argon three times, the temperature was decreased to −80° C. 2.4M n-butyllithium (4.86 mL, 11.66 mmol) was slowly added dropwisely to the reaction system. After stirring for 5 min, anhydrous DMF (12.4 mL) was slowly added dropwisely. After maintaining −80° C. for 20 min, the temperature was raised to room temperature. A large amount of water was slowly added to the reaction system, the solvent was rotary distilled under reduced pressure, and extracted with ethyl acetate. 0.38 g (14.8%) of the product was obtained by column chromatography.

MS(ESI), m/z: 269 (M⁺+H⁺).

Step 3: (2-(4-(trifluoromethoxy) phenyl) pyrimidine-5-yl) methylamine

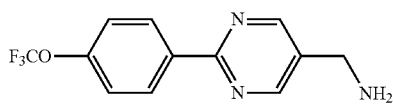

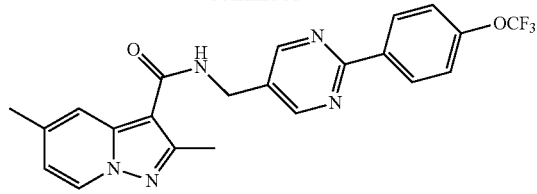

The synthesis process was as described in steps 2, 3 and 4 of Example 26.

MS(ESI), m/z: 270 (M⁺+H⁺).

Step: 4: 2,5-dimethyl-N-((2-(4-(trifluoromethoxy) phenyl) pyrimidine-5-yl) methyl) pyrazolo [1,5-a] pyridine-3-carboxamide (TJ830150)

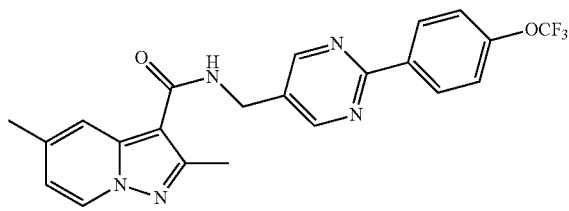 [SMILES: Cc1ccn2nc(C)c(C(=O)NCc3cnc(-c4ccc(OC(F)(F)F)cc4)nc3)c2c1]

The synthesis process was as described in step 9 of Example 1.

¹H NMR (400 MHz, DMSO-d₆): δ8.92 (s, 1H), 8.54 (d, J=7.2 Hz, 1H), 8.49 (d, J=8.8 Hz, 2H), 8.10 (t, J=5.6 Hz, 2H), 7.75 (s, 1H), 7.51 (d, J=8.4 Hz, 2H), 6.82 (dd, J=6.8, 1.2 Hz, 1H), 4.54 (d, J=6.0 Hz, 2H), 2.55 (s, 3H), 2.39 (s, 3H).

MS(ESI), m/z: 442 (M⁺+H⁺).

Example 45: 2,5-dimethyl-N-((4 (trifluoromethoxy)-[1,1'-biphenyl]-4-yl) methyl) pyrazolo [1,5-a] pyridine-3-carboxamide (TJ830151)

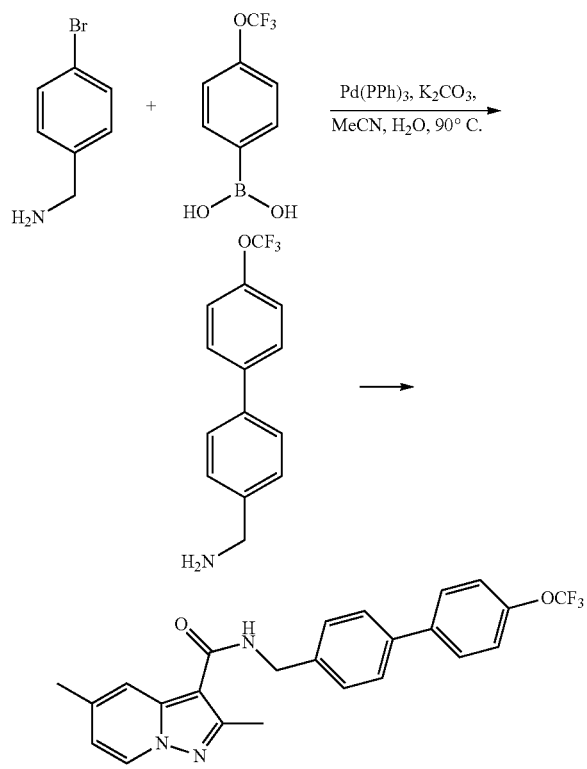

Step 1: (4'-(trifluoromethoxy)-[1,1'-biphenyl]-4-yl) methylamine

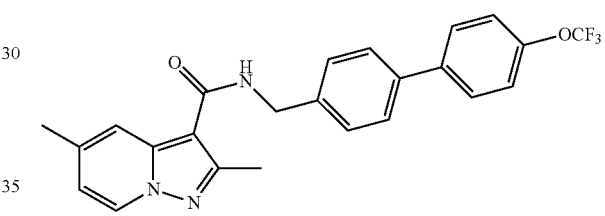

(4-bromophenyl) methylamine (0.56 g, 3.0 mmol), 4-trifluoromethoxybenzeneboronic acid (0.68 g, 3.3 mmol), Pd (PPh₃)₄ (0.17 g, 0.15 mmol) and potassium carbonate (1.66 g, 12 mmol) were dissolved in a mixed solvent of H₂O (6 mL) and acetonitrile (34 mL) and heated to 90° C. overnight. The reaction was cooled to room temperature and filtered through a 2 cm silica gel column. The residue was washed three times with ethyl acetate and the solution was rotary dried under reduced pressure to remove the solvent. 0.72 g (89.6%) of a product was obtained by column chromatography.

MS(ESI), m/z: 268 (M⁺+H⁺).

Step 2: 2,5-dimethyl-N-((4'-(trifluoromethoxy)-[1, 1'-biphenyl]-4-yl) methyl) pyrazolo [1,5-a] pyridine-3-carboxamide (TJ830151)

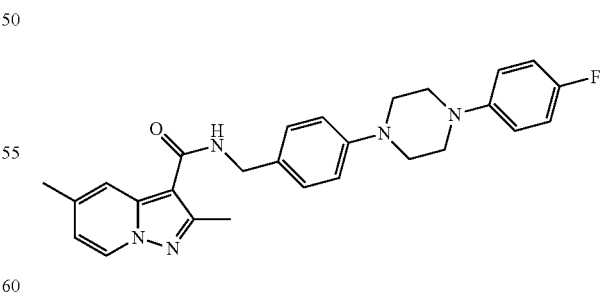

The synthesis process was as described in step 9 of Example 1 with a yield of 67.3%.

¹H NMR (400 MHz, DMSO-d₆): δ8.53 (d, J=7.2 Hz, 1H), 78.04 (t, J=5.6 Hz, 1H), 7.77 (m, 3H), 7.66 (d, J=8.0 Hz, 2H), 7.45 (m, 4H), 6.81 (d, J=7.2 Hz, 1H), 4.53 (d, J=6.0 Hz, 2H), 2.56 (s, 3H), 2.38 (s, 3H).

MS(ESI), m/z: 440 (M⁺+H⁺).

Example 46: N-(4-(4-(4-fluorophenyl) piperazine-1-yl) benzyl)-2,5-dimethyl-pyrazolo [1,5-a] pyridine-3-carboxamide (TJ830152)

The synthesis process was as described in Examples 1 and 6.

¹H NMR (400 MHz, DMSO-d₆): δ8.52 (d, J=6.8 Hz, 1H), 7.91 (t, J=5.6 Hz, 1H), 7.71 (s, 1H), 7.24 (d, J=8.4 Hz, 2H), 7.02 (m, 6H), 6.80 (d, J=6.8 Hz, 1H) 4.40 (d, J=5.6 Hz, 2H), 3.22 (m, 8H), 2.53 (s, 3H), 2.37 (s, 3H).

MS(ESI), m/z: 458 (M⁺+H⁺).

Example 47: 2,5-dimethyl-N-(4-(4-(trifluoromethoxy) phenyl) benzyl) pyrazolo [1,5-a] pyridine-3-carboxamide (TJ830153)

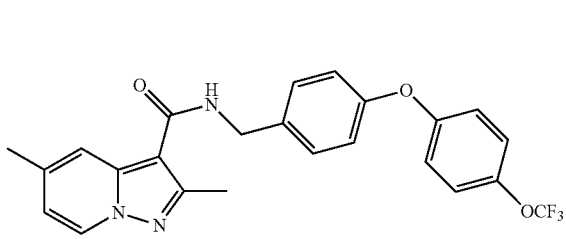 [SMILES: Cc1ccn2nc(C)c(C(=O)NCc3ccc(Oc4ccc(OC(F)(F)F)cc4)cc3)c2c1]

The synthesis process was as described in Example 42.

$^1$H NMR (400 MHz, DMSO-$d_6$): δ8.53 (d, J=7.2 Hz, 1H), 8.00 (s, 1H), 7.73 (s, 1H), 7.39 (m, 4H), 7.06 (m, 4H), 6.81 (d, J=6.8 Hz, 1H), 4.48 (d, J=5.6 Hz, 2H), 2.55 (s, 3H), 2.38 (s, 3H).

MS(ESI), m/z: 456 (M$^+$+H$^+$).

Example 48: 2,5-dimethyl-N-(4-(4-(4-(trifluoromethoxy) phenoxy) piperidine-1-yl) benzyl) pyrazolo [1,5-a] pyridine-3-carboxamide (TJ830161)

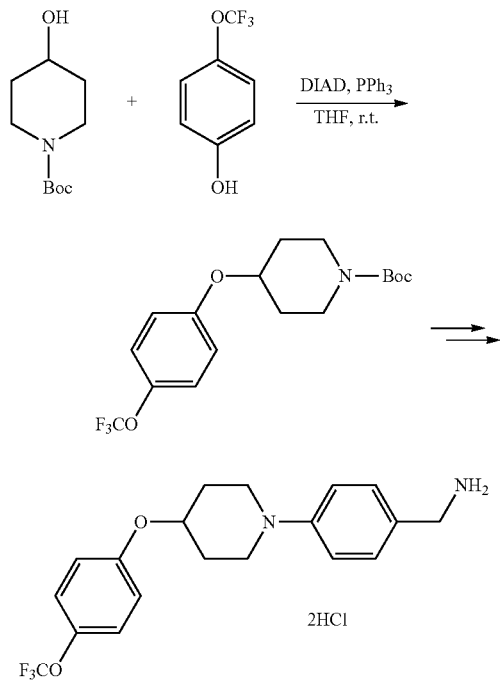

Step 1: tert-butyl 4-(4-(trifluoromethoxy) phenoxy) piperidine-1-carboxylate

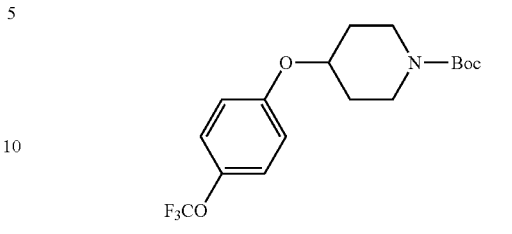

Tert-butyl 4-hydroxypiperidine-1-carboxylate (1.08 g, 5.37 mmol), 4-trifluoromethoxyphenol (1.05 g, 5.9 mmol) and PPh$_3$ (1.55 g, 5.9 mL) (50 mL) were dissolved in THF (50 mL), and DIAD (1.19 g, 5.9 mmol) was slowly added dropwisely to the reaction system. After 2 h reaction, the solvent was rotary distilled under reduced pressure, and a large amount of water was added. After extraction three times with The organic phase was extracted three times with ethyl acetate, the organic phase was combined, and 1.37 g (70.4%) of a product was obtained by column chromatography.

MS(ESI), m/z: 362 (M$^+$+H$^+$).

Step 2: (4-(4-(4-(trifluoromethoxy) phenoxy) piperidine-1-yl) phenyl) methanamine dihydrochloride

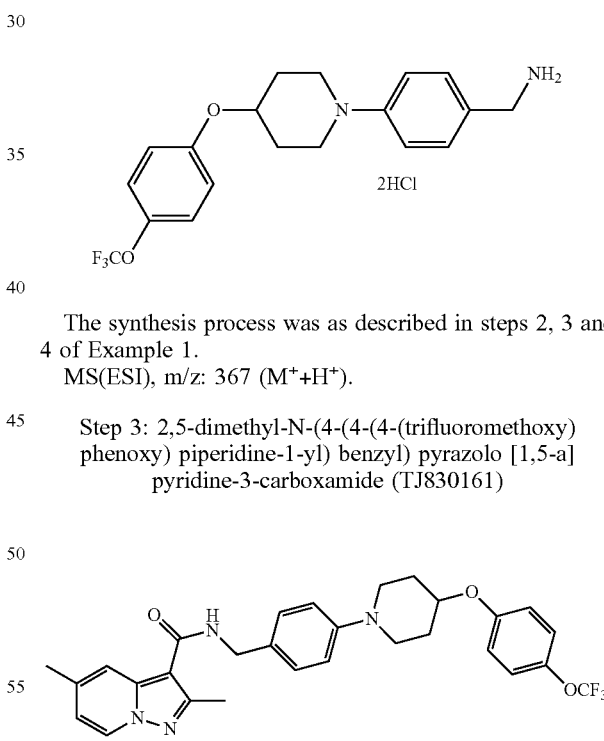

The synthesis process was as described in steps 2, 3 and 4 of Example 1.

MS(ESI), m/z: 367 (M$^+$+H$^+$).

Step 3: 2,5-dimethyl-N-(4-(4-(4-(trifluoromethoxy) phenoxy) piperidine-1-yl) benzyl) pyrazolo [1,5-a] pyridine-3-carboxamide (TJ830161)

The synthesis process was as described in step 9 of Example 1 with a yield of 68.0%.

$^1$H NMR (400 MHz, DMSO-$d_6$): δ8.51 (d, J=7.2 Hz, 1H), 7.90 (t, J=6.0 Hz, 1H), 7.70 (s, 1H), 7.27 (d, J=8.4 Hz, 2H), 7.21 (d, J=8.4 Hz, 2H), 7.08 (d, J=9.2 Hz, 2H), 6.93 (d, J=8.8 Hz, 2H), 6.79 (dd, J=7.2, 1.2 Hz, 1H), 4.57 (m, 1H), 4.38 (d, J=6.0 Hz, 2H), 3.48 (m, 2H), 3.02 (m, 2H), 2.53 (s, 3H), 2.37 (s, 3H), 2.03 (m, 2H), 1.71 (m, 2H).

MS(ESI), m/z: 539 (M$^+$+H$^+$).

Example 49: 5-chloro-2-ethyl-N-(4-fluorobenzyl) pyrazolo [1,5-a] pyridine-3-carboxamide (TJ4570004)

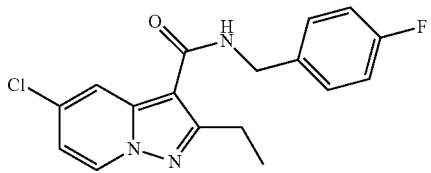 [SMILES: CCc1nn2ccc(Cl)cc2c1C(=O)NCc1ccc(F)cc1]

The synthesis process was as described in Example 1.
$^1$HNMR (400 MHz, DMSO-$d_6$): δ8.73 (d, J=7.2 Hz, 1H), 8.25 (s, 1H), 7.92 (s, 1H), 7.39 (m, 2H), 7.16 (m, 2H), 7.02 (dd, J=7.2, 1.6 Hz, 1H), 4.46 (d, J=6.0 Hz, 2H), 3.00 (q, J=7.2 Hz, 2H), 1.24 (t, J=7.6 Hz, 3H).
MS(ESI), m/z: 332 (M$^+$+H$^+$).

Example 50: N-(4-fluorobenzyl)-2,5-dimethylpyrazolo [1,5-a] pyridine-3-carboxamide (TJ4570006)

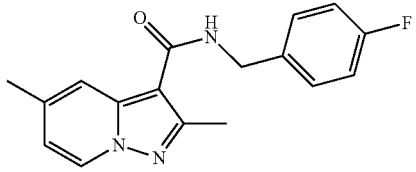 [SMILES: Cc1ccn2nc(C)c(C(=O)NCc3ccc(F)cc3)c2c1]

The synthesis process was as described in Example 6.
$^1$HNMR (400 MHz, DMSO-$d_6$): δ8.52 (d, J=6.8 Hz, 1H), 8.00 (t, J=6.0 Hz, 1H), 7.72 (s, 1H), 7.39 (m, 2H), 7.15 (m, 2H), 6.80 (d, J=6.8 Hz, 1H), 4.46 (d, J=6.0 Hz, 2H), 2.54 (s, 3H), 2.38 (s, 3H).
MS(ESI), m/z: 298 (M$^+$+H$^+$).

Example 51: Inhibitory Activity Against Self-Luminous Tuberculosis

1. Preparation of Self-Luminescent Tuberculosis:
1.1 Culture of Luminescent Bacteria A stable primary luminescent bacteria with a non-resistant screening marker, frozen at −80° C., was inoculated with 2 mL in a conical flask containing 50 mL of 7H9 (containing 0.1% Tween 80) medium and incubated to a solution having an OD value of between 0.3 and 1.0.

Note for check the OD600 value: after bacteria solution was added into the test cup, the mouth of the cup was sealed with a sealing film, and after upside down and gently shaking, detection was immediately began, and repeated three times then taking the average. In addition, in the 1.5 mL EP tube, fluorescence value was detected, and the fluorescence value of about 10-100 million/mL or more was appropriate.

1.2 Obtaining the Test Bacteria Solution and Placing in 384-Well Plate

The bacteria solution was diluted 1, 10, 100 and 1000 times (dilution method: a concentration of 100 μL was taken, and added to 900 μL 7H9 medium for the next concentration, after fully blowing and then dilution was continued). Take the diluted bacteria solution of fluorescence value of 2000-10000/25 μL as a test bacteria solution.

The diluted bacteria was added to a 384-well plate by a pipettor with 25 μL of each well, and the 384-well plate was incubated in a incubator at 37° C. for about 1 to 2 hours. The fluorescence value of each well was measured and the average value of the fluorescence values was recorded as Day 0 fluorescence value.

2. Preparation of Compound Solution and Placement of the Compound Solution in a 384 Well Plate to Save Each test sample was uniformly treated with DMSO to form a mother liquid of 10 mg/mL which was then diluted 3 times. Positive drug rifampicin (RIF) and isoniazid (INH) were treated with DMSO at the two concentrations, 2 mg/mL and 1 mg/mL.

The compound was added to a 384 well plate. In a 384 well plate, 504, of test sample in each well was stored at −20° C.

3. Dosing

A Echo520 Ultrasound Microfluid system was used for dosing, and 25 nL of the test sample was added to each well (in a total volume of 0.025 ml of 7H9 medium) to form a 3-fold dilution starting with a 10 μg/mL final concentration of the compound. The obtained concentrations were 10 mg/mL, 3 mg/mL, 1 mg/mL, 0.3 mg/mL, 0.1 mg/mL, 0.03 mg/mL, 0.01 mg/mL, 0.003 mg/mL, 0.001 mg/mL, 0.0003 mg/0.0001 mg/mL, 0.00003 mg/mL, 0.00001 mg/mL, 0.000003 mg/mL, and 0.000001 mg/mL. 125 nL and 12.5 nL of the positive drugs were respectively added to medium with a final volume of 0.025 nL from a well with 2 mg/mL of the mother liquid, and 2.5 nL of the positive drug was added to medium with a final volume of 0.025 nL from a well with 1 mg/mL of the mother liquid, and final concentration of the positive drug was respectively 10 μg/mL, 1 μg/mL, 0.1 μg/mL. DMSO was as a control. After shaking on the oscillator for 5 min, culture was continued.

4. Detection and Data Analysis

After incubation in a 37° C. incubator, the fluorescence value was detected at 24 hours, 48 hours, 72 hours with envision microplate reader respectively. The samples with fluorescence values decreasing over time are active, where RLU is a relative light unit of the fluorescence value. The results are shown in Table 1.

TABLE 1

MIC$_{lux}$ values of the compound against self-luminescent tuberculosis

| Compound number | MIC$_{lux}$ | Compound number | MIC$_{lux}$ |
|---|---|---|---|
| TJ170298 | A | TJ170322 | A |
| TJ170371 | B | TJ170372 | A |
| TJ170375 | A | TJ170381 | A |
| TJ170385 | A | TJ170386 | C |
| TJ064814 | B | TJ064819 | C |
| TJ064851 | B | TJ064854 | A |
| TJ064872 | C | TJ064889 | A |
| TJ064983 | C | TJ064985 | B |
| TJ064987 | C | TJ064995 | B |
| TJ830003 | C | TJ830008 | A |
| TJ830012 | C | TJ830028 | A |
| TJ830025 | A | TJ830047 | A |
| TJ830069 | B | TJ830070 | C |
| TJ830072 | A | TJ830073 | B |
| TJ830075 | C | TJ830082 | A |
| TJ830102 | A | TJ830108 | A |
| TJ830128 | B | TJ830132 | A |
| TJ830133 | A | TJ830134 | A |
| TJ830135 | A | TJ830136 | A |
| TJ830140 | A | TJ830141 | A |
| TJ830146 | A | TJ830147 | A |

TABLE 1-continued

MIC$_{lux}$ values of the compound against self-luminescent tuberculosis

| Compound number | MIC$_{lux}$ | Compound number | MIC$_{lux}$ |
|---|---|---|---|
| TJ830149 | A | TJ830150 | A |
| TJ830151 | A | TJ830152 | A |
| TJ830153 | A | TJ830161 | A |
| TJ4570004 | C | TJ4570006 | B |

The activity range: A indicates <1 μg/mL, B indicates 1-10 μg/mL and C indicates >10 μg/mL.

Example 52: Determination of the *Mycobacterium Tuberculosis* MIC (Minimal Inhibitory Concentration) of the Compound of the Present Disclosure by a Plate Method 1. Submerged culture of *Mycobacterium tuberculosis* standard strain H37Rv: it was cultured in 7H9 medium, and cultured in a shaker at 37° C. until absorbance of the bacteria solution at 600 nm (OD$_{600}$) was 0.3-0.7.

2. Preparation of 7H11 plates with different concentration of compound (the design of the compound concentration was as shown in Table 2): the compound was dissolved in DMSO at a concentration of 1:1000 in the medium and the control only used the same amount of DMSO adding to the plate without drug.

3. MIC test: *Mycobacterium tuberculosis* standard strain H37Rv medium was diluted with sterile water to 50 times to obtain a mother liquor, and then the mother liquor was diluted to 10$^{-3}$ and 10$^{-5}$ concentration, and then the two concentrations of bacteria solution were each taken 0.5 ML to put on the 7H11 plate, each of which was repeated twice. The one that added positive drug isoniazid 0.1 μg/mL was as control.

TABLE 2

Design of the compound concentration

| compound | Bacteria solution concentration 10$^{-3}$ Concentration (ng/mL) | | | | | Bacteria solution concentration 10$^{-5}$ Concentration (ng/mL) | | | | |
|---|---|---|---|---|---|---|---|---|---|---|
| TJ170322 | 6.25 | 12.5 | 25 | 50 | 100 | 6.25 | 12.5 | 25 | 50 | 100 |
| TJ170372 | 6.25 | 12.5 | 25 | 50 | 100 | 6.25 | 12.5 | 25 | 50 | 100 |
| TJ170381 | 6.25 | 12.5 | 25 | 50 | 100 | 6.25 | 12.5 | 25 | 50 | 100 |
| TJ170385 | 1.25 | 2.5 | 5 | 10 | — | 1.25 | 2.5 | 5 | 10 | — |
| TJ170375 | 6.25 | 12.5 | 25 | 50 | 100 | 6.25 | 12.5 | 25 | 50 | 100 |
| positive control isoniazid (μg/mL) | | 0.1 | | | | | 1 | | | |

4. Results and Analysis:

The cells were incubated at 37° C. for 4 weeks, and the number of colonies per plate was counted. The data were analyzed and the MIC values of the compounds were obtained. The results are shown in Table 3.

TABLE 3

MIC values for each compound

| compound | MIC (μg/mL) |
|---|---|
| TJ170322 | 0.1 |
| TJ170372 | 0.01 |
| TJ170381 | 0.1 |
| TJ170385 | 0.01 |

TABLE 3-continued

MIC values for each compound

| compound | MIC (μg/mL) |
|---|---|
| TJ170375 | 0.1 |
| positive control isoniazid | <=0.1 |
| negative control DMSO | — |

Example 53: Sensitivity Determination of the Compound to Clinically Selected Multi-Drug Resistant Tuberculosis (MDR-TB) Strains 1. Submerged culture of *mycobacterium tuberculosis* standard strain H37Rv and clinical sorted MDR-TB P91, P105 and P103: it was cultured in 7H9 medium, and cultured in a shaker at 37° C. until absorbance of the bacteria solution at 600 nm (OD$_{600}$) was above 0.7.

2. Preparation of 71-111 plates with different concentration of compound TJ170298 (the design of the compound concentration was as shown in Table 4): the compound was dissolved in DMSO at a concentration of 1:1000 in the medium.

3. MIC test: Each tuberculosis strain medium was diluted with sterile water to 50 times to obtain a mother liquor, and then the mother liquor was diluted to 10$^{-3}$ and 10$^{-5}$ concentration, and then the two concentrations of bacteria solution were each taken 0.5 ML to put on the 7H11 plate, each of which was repeated twice. The one that added positive drug RIF 10 μg/mL and 1 μg/mL was as control.

TABLE 4

Design of the compound concentration

| | strain | | | |
|---|---|---|---|---|
| | P91 | P105 | P103 | H37Rv |
| compound concentration (μg/mL) | 10 | 10 | 10 | 10 |
| | 5 | 5 | 5 | 5 |
| | 2.5 | 2.5 | 2.5 | 2.5 |
| | 1.25 | 1.25 | 1.25 | 1.25 |
| | 0.625 | 0.625 | 0.625 | 0.625 |
| | 0.3 | 0.3 | 0.3 | 0.3 |
| | 0.15 | 0.15 | 0.15 | 0.15 |
| | 0.075 | 0.075 | 0.075 | 0.075 |

4. Results and Analysis:

The MIC detection results of compound TJ170298 for clinical sorted MDR-TB and standard H37Rv was as shown in Table 5:

TABLE 5

MIC value of each compound for clinical sorted MDR-TB and standard H37Rv

| drug | strain | MIC (μg/mL) |
|---|---|---|
| TJ170298 | P91 | <0.075 |
| | P105 | 0.15 |
| | P103 | <0.075 |
| | H37Rv | 0.012 |
| RIF | P91 | 1-10 |
| | P105 | >10 |
| | P103 | >10 |
| | H37Rv | — |

Example 54: Determination of the Activity of the Compound of the Present Disclosure Against Tuberculosis In Vivo 1. Submerged culture of *mycobacterium tuberculosis* self-luminescent bacteria H37Ra: it was cultured in 7H9 medium, and cultured in a shaker at 37° C. until luminous value of the bacteria solution was above 22,000,000 RLU/mL.

2. Purchasing of 5-6 weeks old BALB/c male mice for infection experiments: each BALB/c male mouse was injected with tail vein using self-luminescent bacteria H37Ra. The luminous values of infected BALB/c male mice were measured after 1 day, and BALB/c male mice with luminous values greater than 700 RLU/were randomized grouped.

3. In vivo activity of the compound: different concentrations of different types of compounds were respectively intragastricly administered to BALB/c male mice 2 days after the infection, once a day, continuous intragastric administration of 6 days, and the specific treatment amount is as shown in Table 6:

TABLE 6

Treatment amount of the compound

| compound | solvent | amount of the compound used each time (μL) | concentration (μg/mL) | corresponding dose (mg/kg) |
|---|---|---|---|---|
| L298 | CMCNa | 200 | 10 | 100 |
| (TJ170298) | edible oil | 100 | 5 | 25 |
| | CMCNa | 200 | 2 | 20 |
| L372 | CMCNa | 200 | 10 | 100 |
| (TJ170372) | edible oil | 200 | 5 | 50 |
| | CMCNa | 200 | 2 | 20 |
| L385 | CMCNa | 200 | 10 | 100 |
| (TJ170385) | edible oil | 100 | 5 | 25 |
| | CMCNa | 200 | 2 | 20 |
| positive control Rifampicin | CMCNa | 200 | 4 | 40 |
| negative control CMCNa | CMCNa | 200 | — | — |

4. Real-time monitoring in vivo anti-tuberculosis activity of the compound: the luminous values within live mice were respectively measured day0, day2, day4, so that in vivo anti-tuberculosis activity of the compound was real-time detected.

Figure 2:
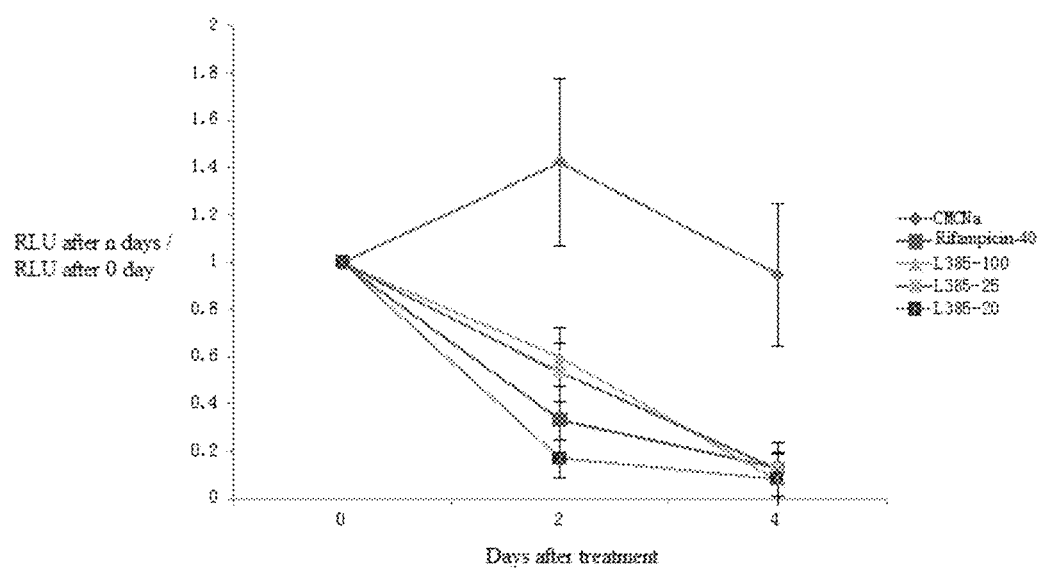
FIG. 2 shows the results of the real-time in vivo anti-tuberculosis activity assay of the compound L385.
Figure 3:
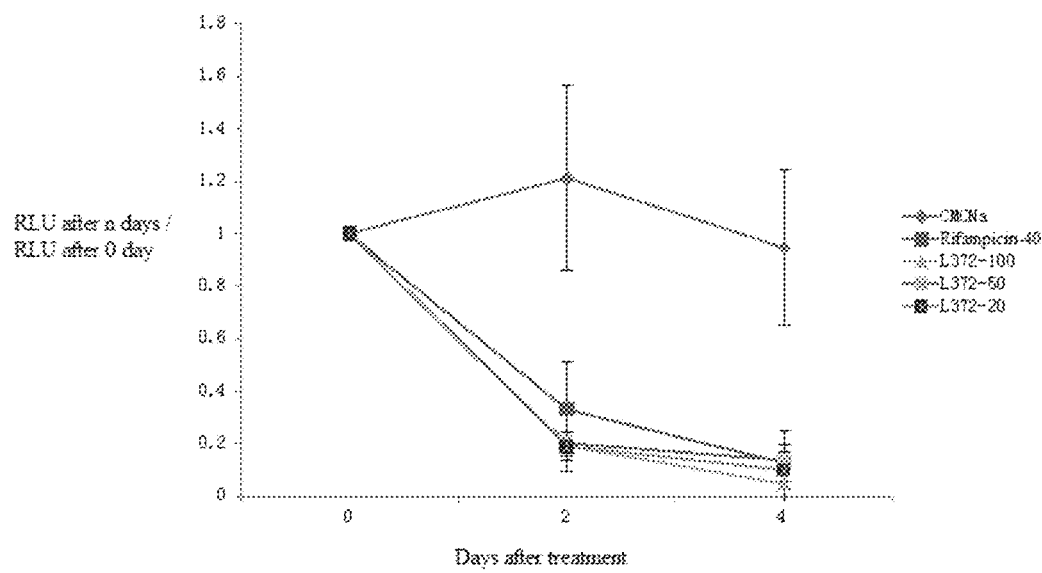
FIG. 3 shows the results of the real-time in vivo anti-tuberculosis activity assay of the compound L372.
Figure 4:
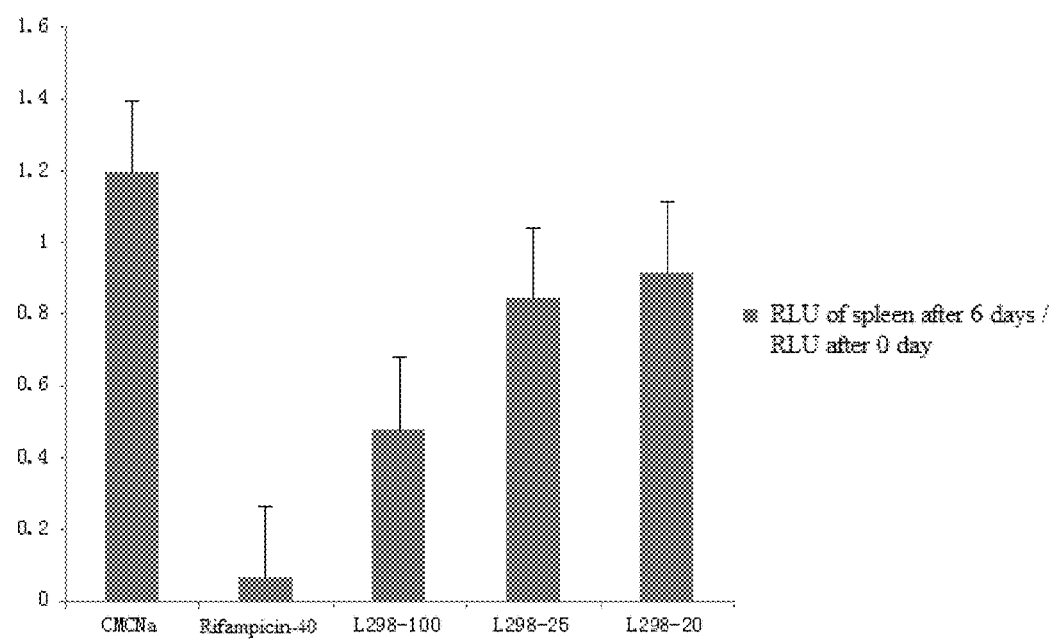
FIG. 4 shows the results of anti-tuberculosis activity assay of the compound L298 in the spleen.

The results of the experiment shown in FIGS. 1-4, compounds L298, L385, L372H37Ra have obvious in vivo anti-tuberculosis activity, and the activity is equal to or better than that of the positive control Rifampicin, but the spleen anti-tuberculosis activity thereof is bad than that of the positive control Rifampicin.

Example 55: Pharmacokinetic Studies of Compounds TJ170298 and TJ170385

1. Administration and Sample Collection a. Rat intravenous administration: SD rats 3, weight 180~220 g. Fasting 12 h before administration, a small amount of food was allowed during the experiment, and water was free. The compounds TJ170298 and TJ170385 were administered intravenously at a dose of 2 mg/kg. The rats were respectively taken 0.3 mL orbital blood at 2 min, 10 min, 30 min, 1.0 h, 2.0 h, 3.0 h, 4.0 h, 6.0 h, 8.0 h, 12.0 h, 21 h, 24.0 h, 30 h, 36 h, 48 h, 60 h, 72 h after administration, which was then placed in heparinized test tube, centrifuged 10 min at 6000 rpm, and plasma was separated, preserved at 4° C. to be measured.

b. Rat oral administration: SD rats 3, weight 180~220 g. Fasting for 12 h before administration, a small amount of food was allowed during the experiment, and water was free. The compounds TJ170298 and TJ170385 were orally administered at a dose of 10 mg/kg, respectively. The rats were respectively taken 0.3 mL orbital blood at 2 min, 10 min, 30 min, 1.0 h, 2.0 h, 3.0 h, 4.0 h, 6.0 h, 8.0 h, 12.0 h, 21 h, 24.0 h, 30 h, 36 h, 48 h, 60 h, 72 h after administration, which was then placed in heparinized test tube, centrifuged 10 min at 6000 rpm, and plasma was separated, preserved at 4° C. to be measured.

2. Determination of Plasma Samples a. Plasma Sample Treatment

150 μl of the internal standard solution (5 μl/mL, acetonitrile solution) was added to 50 μL of the above plasma sample, mixed well; after eddy mixing for 2 min, centrifuge for 30 min (13000 rpm, 4° C.), supernatant was taken to another centriguge tube, and 20 μL of which was taken for LC/MS/MS analysis.

b. Preparation of Standard Curve

50 μL of rat blank plasma was taken, to which 10 μL of compound standard series solution was added to prepare compound plasma samples equivalent to plasma concentration of 20, 50, 100, 500, 1000, 2000, 4000, 6000, 12000, 40000 ng/mL. According to "plasma sample treatment" item, the standard curve was established. The concentration (X) of an analyte is as the abscissa, the peak area ratio (y) of the analyte and the internal standard is as the ordinate, and the regression is performed by the weighted (W=1/x2) least squares method to obtain the linear regression Equation, that is, the standard curve.

C. Data Processing and Analysis

The pharmacokinetic parameters of rats after administration were calculated by DAS 2.0 software.

TABLE 7

Pharmacokinetic properties parameters of compounds in SD rats

| | TJ170298 (hydrochloride) | | TJ170385 | |
|---|---|---|---|---|
| | Oral administration | Intravenous administration | Oral administration | Intravenous administration |
| Number of animal | ♂3 | ♂3 | ♂3 | ♂3 |
| dose (mg/kg) | 10 | 2 | 10 | 2 |

TABLE 7-continued

Pharmacokinetic properties parameters of compounds in SD rats

| | TJ170298 (hydrochloride) | | TJ170385 | |
|---|---|---|---|---|
| | Oral administration | Intravenous administration | Oral administration | Intravenous administration |
| AUC (0-∞) (ug/L * h) | 4697.704 | 3897.612 | 9591.85 | 2028.972 |
| $T^{1/2}$ (h) | 19.699 | 19.975 | 27.374 | 10.933 |
| Tmax (h) | 2 | 0.033 | 2 | — |
| Cmax (ug/L) | 509 | 1548.333 | 644.333 | 1042.5 |
| BA (%) | 24.1% | | 94.5% | |

AUC (Area Under the Curve): plasma concentration—the time under the curve of the area, represents the bioavailability of drugs (the extent to which the drug is absorbed in the human body). AUC is large then bioavailability is high, and vice versa. AUC is full called area under concentration-time curve.

Cmax: Peak Concentration refers to the maximum plasma concentration on the plasma concentration-time curve, ie, the highest plasma concentration that can be achieved after administration. The peak concentration of the drug is closely related to the clinical application of the drug. Peak concentration achieves an effective concentration in order to be effective, and if it is higher than the safety range, the toxic response can be shown. In addition, the peak concentration is also an important measure of the absorption and safety of the preparation.

$T^{1/2}$ (half life time): half life. It refers to the time required for the concentration of the drug in the body to drop by half, reflecting the speed at which the drug is removed from the body by biotransformation or excretion.

Tmax: Peak Time refers to the time required to achieve the highest concentration (peak concentration) on the plasma concentration curve after administration. Peak time being short means that drug absorption is fast, and rapid onset, but also eliminate the fast; while drug peak being long means that the drug absorption is slow and slow onset, and the duration of drug effects are often extended. Peak time is an important indicator of the application of drugs and research preparations.

BA (bioavailability): bioavailability. It refers to the rate and extent of drug absorption into the large cycle. Bioavailability consists of absolute bioavailability and relative bioavailability. Absolute bioavailability refers to, given that 100% of a drug administered intravenously is abosorbed by the body, a percentage of absorbed by the body of the drug in other formulations when administered in the same dose as that of the drug administered intravenously. While the relative bioavailability is, given that 100% of a drug of any specified formulation (eg oral water preparation) is abosorbed by the body, a percentage of absorbed by the body of the drug in other formulations when administered under the same conditions.

It can be seen from Table 7 that compounds TJ170298 and TJ170385 have good pharmacokinetic properties.

The embodiments described above are merely illustrative of several embodiments of the present disclosure and are more specific and detailed, but are not to be construed as limiting the scope of the present disclosure. It should be noted that various modifications and improvements can be made by a person skilled in the art without departing from the spirit of the present disclosure, which are within the scope of the present disclosure. Accordingly, the scope of protection of the present disclosure should be determined by the appended claims.

The invention claimed is:

1. A pyrazolo[1,5-a]pyridine compound having a structure of formula (I) or a pharmaceutically acceptable salt thereof or a stereoisomer thereof or a prodrug molecule thereof:

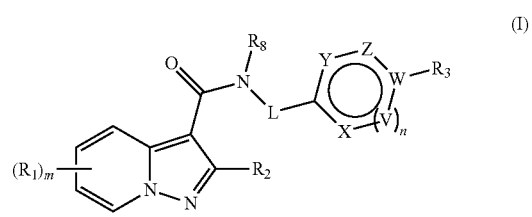

wherein, m is 0, 1, 2, 3 or 4;

n is 1;

V is CH;

W is CH;

X is CH;

Y is CH;

Z is CH;

L is $C_1$-$C_5$ straight or branched alkane;

$R_8$ is H or methyl;

$R_1$ is selected from the group consisting of
  H;
  halogen;
  $O_aC_1$-$C_5$ alkyl;
  $C_3$-$C_6$ cycloalkyl; and
  phenyl;

wherein the $O_aC_1$-$C_5$ alkyl, the $C_3$-$C_6$ cycloalkyl and the phenyl are optionally substituted with 0, 1, 2 or 3 substituents selected from $R_6$, respectively;

$R_2$ is
  $O_aC_1$-$C_5$ alkyl; or $C_3$-$C_6$ cycloalkyl;

wherein the $O_aC_1$-$C_5$ alkyl, or the $C_3$-$C_6$ cycloalkyl are optionally substituted with 0, 1, 2 or 3 substituents selected from $R_6$, respectively;

$R_3$ is selected from the group consisting of
  $O_aC_1$-$C_5$ alkyl;
  $C_3$-$C_6$ cycloalkyl;

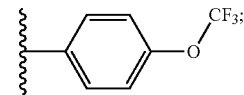

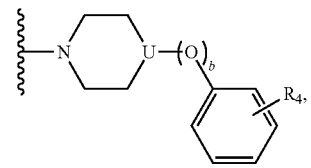

wherein b is 0 or 1, U is CH or N; $R_4$ is optionally selected from the group consisting of H; F, Cl, Br; $C_1$-$C_3$ alkyl; $C_1$-$C_3$ alkoxy; and phenoxy;

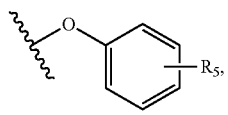

wherein R$_5$ is optionally selected from the group consisting of a) H; b) F, Cl, Br; and c) O$_a$C$_1$-C$_3$ alkyl;

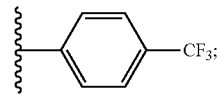

(C=O)$_c$O$_d$R$_7$, wherein c is 0 or 1; d is 0 or 1; R$_7$ is optionally selected from the group consisting of a) CF$_3$; and b) C$_1$-C$_5$ alkyl;

—N(CH$_3$)$_2$;

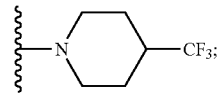

and

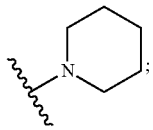 [SMILES: *N1CCCCC1]

wherein the alkyl, the aryl, the cycloalkyl, the heterocycloalkyl and the heteroaryl are optionally substituted with 0, 1, 2 or 3 substituents selected from R$_6$, wherein a is 0 or 1;

R$_6$ is optionally selected from the group consisting of H; C$_3$-C$_6$ cycloalkyl; heterocyclyl; C$_1$-C$_3$ alkyl; C$_1$-C$_3$ fluoroalkyl; C$_0$-C$_3$ alkylene-heterocyclyl; and halogen.

2. The pyrazolo[1,5-a]pyridine compound or a pharmaceutically acceptable salt thereof or a stereoisomer thereof or a prodrug molecule thereof of claim 1, wherein, R$_1$ is optionally selected from the group consisting of
1) H;
2) F, Cl, Br, I;
3) OH, OCH$_3$, OEt, OCF$_3$;
4) methyl, ethyl, isopropyl, t-butyl;
5) cyclopropyl;
6) CF$_3$; and
7) phenyl;

R$_2$ is optionally selected from the group consisting of
1) H;
2) methyl, ethyl, propyl, isopropyl, t-butyl;
3) cyclopropyl; and
4) phenyl;

R$_3$ is optionally selected from the group consisting of
1)

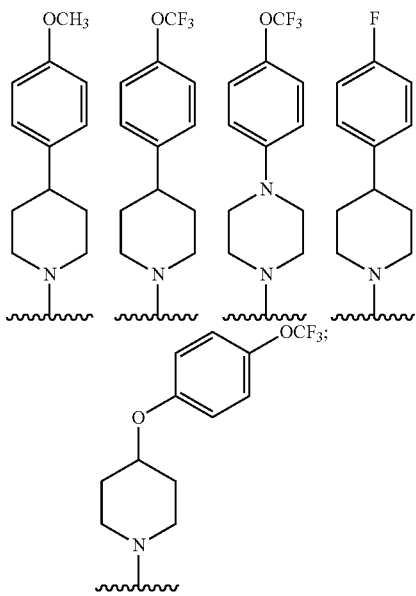

2)

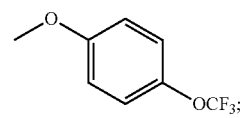

3)

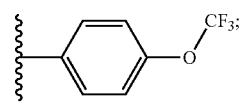

4)

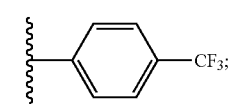

5) CF$_3$; and
6) (C=O)$_c$O$_d$R$_7$, wherein c is 0 or 1; d is 0 or 1; R$_7$ is optionally selected from the group consisting of a) CF$_3$; and b) C$_1$-C$_5$ alkyl.

3. The pyrazolo[1,5-a]pyridine compound or a pharmaceutically acceptable salt thereof or a stereoisomer thereof or a prodrug molecule thereof of claim 1, wherein, the

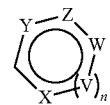

is

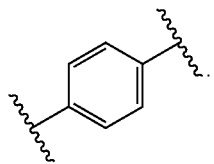 [SMILES: *c1ccc(*)cc1]

4. The pyrazolo[1,5-a]pyridine compound or a pharmaceutically acceptable salt thereof or a stereoisomer thereof or a prodrug molecule thereof of claim 1, wherein, the pyrazolo[1,5-a]pyridine compound has a structure of formula (II):

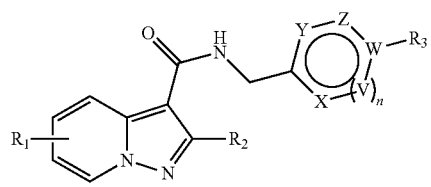

wherein $R_1$ is methyl;
$R_2$ is methyl;
$R_3$ is optionally selected from the group consisting of
1) —N(CH₃)₂;
2)

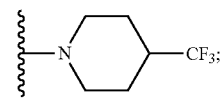

3) —C(CH₃)₃;
4)

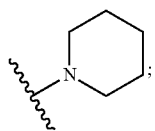

5) and

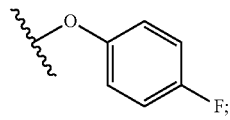 [SMILES: *Oc1ccc(F)cc1]

6)

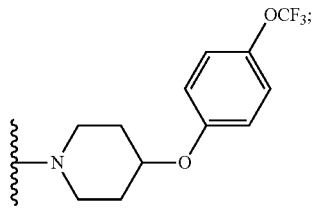 [SMILES: *N1CCC(Oc2ccc(OC(F)(F)F)cc2)CC1]

n=1.

5. The pyrazolo[1,5-a]pyridine compound or a pharmaceutically acceptable salt thereof or a stereoisomer thereof or a prodrug molecule thereof of claim 1, wherein, the pyrazolo[1,5-a]pyridine compound has the structure of formula (II):

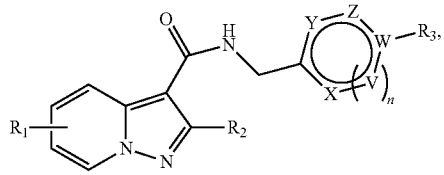

wherein
$R_1$ is optionally selected from the group consisting of
1) H;
2) F, Cl, Br, I;
3) OH, OCH₃, OEt, OCF₃;
4) methyl, ethyl, isopropyl, t-butyl;
5) cyclopropyl;
6) CF₃; and
7) phenyl;
$R_2$ is optionally selected from the group consisting of
1) H;
2) methyl, ethyl, propyl, isopropyl;
3) cyclopropyl; and
4) phenyl;
$R_3$ is optionally selected from the group consisting of
1)

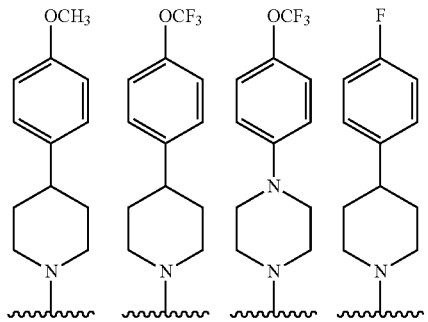

2)

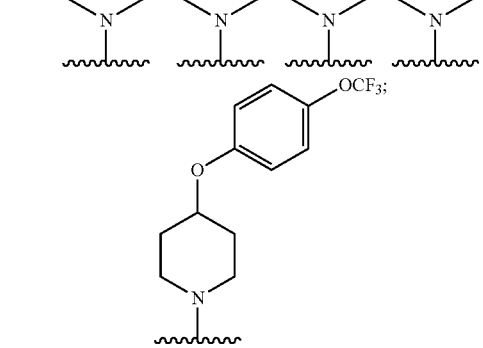

3)

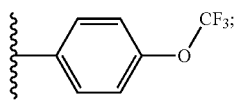 [SMILES: *c1ccc(OC(F)(F)F)cc1]

4)

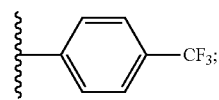

5) CF$_3$; and
6) (C=O) OMe;
wherein

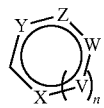

is

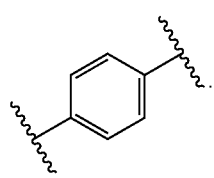 [SMILES: *c1ccc(*)cc1]

6. The pyrazolo[1,5-a]pyridine compound or a pharmaceutically acceptable salt thereof or a stereoisomer thereof or a prodrug molecule thereof of claim 1, wherein, the pyrazolo[1,5-a]pyridine compound has a structure of formula (III):

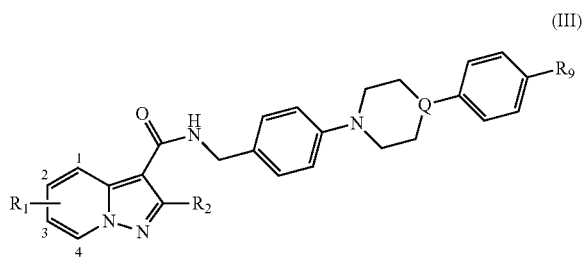

(III)

R$_1$ is optionally selected from the group consisting of
1) H;
2) F, Cl, Br;
3) OH, OCH$_3$, OEt;
4) methyl, ethyl, isopropyl, t-butyl;
5) CF$_3$; and
6) phenyl;
R$_2$ is optionally selected from the group consisting of
1) H;
2) methyl, ethyl, propyl;
3) cyclopropyl; and
4) phenyl;

R$_9$ is optionally selected from the group consisting of
1) F, Cl, Br; and
2) OCH$_3$, OCF$_3$;
Q is optionally selected from CH and N.

7. The pyrazolo[1,5-a]pyridine compound or a pharmaceutically acceptable salt thereof or a stereoisomer thereof or a prodrug molecule thereof of claim 6, wherein,
R$_1$ is optionally selected from the group consisting of
1) 2-Cl, 2-Br;
2) 2-OCH$_3$, 2-OEt;
3) 2-methyl, 2-ethyl, 3-methyl, 3-ethyl; and
4) H;
R$_2$ is optionally selected from the group consisting of
1) methyl, ethyl, propyl; and
2) cyclopropyl;
R$_9$ is optionally selected from the group consisting of
1) F, Cl; and
2) OCH$_3$, OCF$_3$;
Q is optionally selected from CH and N.

8. The pyrazolo[1,5-a]pyridine compound or a pharmaceutically acceptable salt thereof or a stereoisomer thereof or a prodrug molecule thereof of claim 5, wherein, the pyrazolo[1,5-a]pyridine compound has a structure of formula (IV):

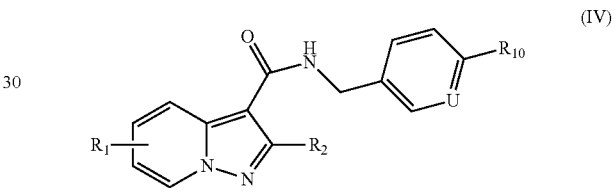

(IV)

wherein
R$_1$ is optionally selected from the group consisting of
1) H;
2) F, Cl, Br;
3) OH, OCH$_3$, OEt;
4) methyl, ethyl, isopropyl, t-butyl;
5) CF$_3$; and
6) phenyl;
R$_2$ is optionally selected from the group consisting of
1) H;
2) methyl, ethyl, propyl;
3) cyclopropyl; and
4) phenyl;
R$_{10}$ is optionally selected from the group consisting of
1) H;
2) F, Cl, Br;
3) CF$_3$; and
4)

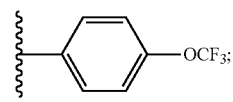

U is CH.

9. The pyrazolo[1,5-a]pyridine compound or a pharmaceutically acceptable salt thereof or a stereoisomer thereof or a prodrug molecule thereof of claim 5, wherein, the pyrazolo[1,5-a]pyridine compound has the structure of formula (II):

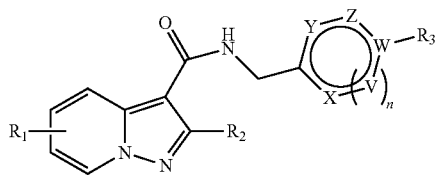

(II)

wherein
R₁ is methyl;
R₂ is methyl;
R₃ is optionally selected from the group consisting of
1) and

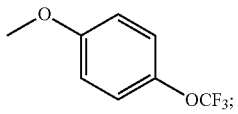

2)

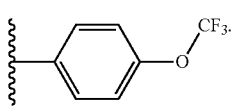

10. The pyrazolo[1,5-a]pyridine compound or a pharmaceutically acceptable salt thereof or a stereoisomer thereof or a prodrug molecule thereof of claim 1, wherein the compound is selected from the group consisting of:

5-chloro-2-ethyl-N-(4-(4-(4-(trifluoromethoxy)phenyl) piperidine-1-yl)benzyl)pyrazolo [1,5-a]pyridine-3-carboxamide;
5-chloro-N-(4-(4-(4-(trifluoromethoxy)phenyl)piperidine-1-yl)benzyl)pyrazolo[1,5-a]pyridine-3-carboxamide;
5-chloro-2-methyl-N-(4-(4-(4-(trifluoromethoxy) phenyl) piperidine-1-yl) benzyl) pyrazolo [1,5-a] pyridine-3-carboxamide;
5-chloro-2-cyclopropyl-N-(4-(4-(4-(trifluoromethoxy) phenyl) piperidine-1-yl) benzyl) pyrazolo [1,5-a] pyridine-3-carboxamide;
2-methyl-N-(4-(4-(4-(trifluoromethoxy) phenyl) piperidine-1-yl) benzyl) pyrazolo [1,5-a] pyridine-3-carboxamide;
2,5-dimethyl-N-(4-(4-(4-(trifluoromethoxy)phenyl) piperidine-1-yl) benzyl) pyrazolo[1,5-a] pyridine-3-carboxamide;
5-chloro-2-phenyl-N-(4-(4-(4-(trifluoromethoxy) phenyl) piperidine-1-yl) benzyl) pyrazolo [1,5-a] pyridine-3-carboxamide;
4-((5-chloro-2-ethylpyrazolo[1,5-a] pyridine-3-carboxamide) methyl) methyl benzoate;
2,7-dimethyl-N-(4-(4-(4-(trifluoromethoxy) phenyl) piperidine-1-yl) benzyl) pyrazolo [1,5-a] pyridine-3-carboxamide;
2,6-dimethyl-N-(4-(4-(4-(trifluoromethoxy) phenyl) piperidine-1-yl) benzyl) pyrazolo [1,5-a] pyridine-3-carboxamide;
2,4-dimethyl-N-(4-(4-(4-(trifluoromethoxy) phenyl) piperidine-1-yl) benzyl) pyrazolo [1,5-a] pyridine-3-carboxamide;
5-methoxy-2-ethyl-N-(4-(4-(4-(trifluoromethoxy) phenyl) piperidine-1-yl) benzyl) pyrazolo [1,5-a] pyridine-3-carboxamide;
5-chloro-2-ethyl-N-(2-(4-(4-(4-(trifluoromethoxy) phenyl) piperidine-1-yl) phenyl) propane-2-yl) pyrazolo [1,5-a] pyridine-3-carboxamide;
5-trifluoromethyl-2-methyl-N-(4-(4-(4-(trifluoromethoxy) phenyl) piperidine-1-yl) benzyl) pyrazolo [1,5-a] pyridine-3-carboxamide;
5-bromo-2-methyl-N-(4-(4-(4-(trifluoromethoxy) phenyl) piperidine-1-yl) benzyl) pyrazolo [1,5-a] pyridine-3-carboxamide;
5-phenyl-2-methyl-N-(4-(4-(4-(trifluoromethoxy) phenyl) piperidine-1-yl) benzyl) pyrazolo [1,5-a] pyridine-3-carboxamide;
5-methoxy-2-methyl-N-(4-(4-(4-(trifluoromethoxy) phenyl) piperidine-1-yl) benzyl) pyrazolo [1,5-a] pyridine-3-carboxamide;
2-methyl-N-(4-(trifluoromethoxy) benzyl) pyrazolo [1,5-a] pyridine-3-carboxamide;
5-chloro-2-ethyl-N-(1-(4-(4-(4-(trifluoromethoxy) phenyl) piperidine-1-yl) phenyl) ethanol) pyrazolo [1,5-a] pyridine-3-carboxamide;
2,5-dimethyl-N-(4-(trifluoromethoxy) benzyl) pyrazolo [1,5-a] pyridine-3-carboxamide;
5-isopropyl-2-methyl-N-(4-(4-(4-(trifluoromethoxy) phenyl) piperidine-1-yl) benzyl) pyrazolo [1,5-a] pyridine-3-carboxamide;
5-tert-butyl-2-methyl-N-(4-(4-(4-(trifluoromethoxy) phenyl) piperidine-1-yl) benzyl) pyrazolo [1,5-a] pyridine-3-carboxamide;
5-ethyl-2-methyl-N-(4-(4-(4-(trifluoromethoxy) phenyl) piperidine-1-yl) benzyl) pyrazolo [1,5-a] pyridine-3-carboxamide;
5-methyl-2-ethyl-N-(4-(4-(4-(trifluoromethoxy) phenyl) piperidine-1-yl) benzyl) pyrazolo[1,5-a] pyridine-3-carboxamide;
5-methyl-2-ethoxy-N-(4-(4-(4-(trifluoromethoxy) phenyl) piperidine-1-yl) benzyl) pyrazolo [1,5-a] pyridine-3-carboxamide;
5-chloro-2-ethyl-N-(4-(4-(4-(trifluoromethoxy) phenyl) piperidine-1-yl) phenethyl) pyrazolo [1,5-a] pyridine-3-carboxamide;
N-(4-(tert-butyl) benzyl)-2,5-dimethylpyrazolo [1,5-a] pyridine-3-carboxamide;
N-(4-(dimethylamino) benzyl)-2,5-dimethylpyrazolo [1,5-a] pyridine-3-carboxamide;
N-(4-(4-(4-methoxyphenyl) piperidine-1-yl) benzyl)-2,5-dimethyl-pyrazolo [1,5-a] pyridine-3-carboxamide;
N-(4-(4-(4-fluorophenyl)piperidine-1-yl) benzyl)-2,5-dimethyl-pyrazolo [1,5-a] pyridine-3-carboxamide;
2,5-dimethyl-N-(4-(piperidin-1-yl) benzyl) pyrazolo [1,5-a] pyridine-3-carboxamide;
N-(4-(4-fluorophenoxy) benzyl)-2,5-dimethylpyrazolo [1,5-a] pyridine-3-carboxamide;
2,5-dimethyl-N-(4-(4-(trifluoromethyl) piperidine-1-yl) benzyl) pyrazolo [1,5-a] pyridine-3-carboxamide;
2,5-dimethyl-N-((4'-(trifluoromethoxy)-[1,1'-biphenyl]-4-yl) methyl) pyrazolo [1,5-a] pyridine-3-carboxamide;
N-(4-(4-(4-fluorophenyl) piperazine-1-yl) benzyl)-2,5-dimethyl-pyrazolo [1,5-a] pyridine-3-carboxamide;
2,5-dimethyl-N-(4-(4-(trifluoromethoxy) phenyl) benzyl) pyrazolo [1,5-a] pyridine-3-carboxamide; and
2,5-dimethyl-N-(4-(4-(4-(trifluoromethoxy) phenoxy) piperidine-1-yl) benzyl) pyrazolo [1,5-a] pyridine-3-carboxamide.

11. An anti-tuberculosis pharmaceutical composition, comprising an active ingredient which includes the pyrazolo[1,5-a]pyridine compound or a pharmaceutically acceptable salt thereof or a stereoisomer thereof or a prodrug molecular thereof of claim 1.

\* \* \* \* \*